(12) United States Patent
Shuman

(10) Patent No.: US 6,232,070 B1
(45) Date of Patent: *May 15, 2001

(54) PHARMACOLOGICAL TARGETING OF MRNA CAP FORMATION

(76) Inventor: Stewart Shuman, 504 E. 63rd St., Apt. 9R, New York, NY (US) 10021

( * ) Notice: Subject to any disclaimer, the term of this patent is extended or adjusted under 35 U.S.C. 154(b) by 0 days.

This patent is subject to a terminal disclaimer.

(21) Appl. No.: 09/315,444

(22) Filed: May 20, 1999

Related U.S. Application Data

(63) Continuation-in-part of application No. 09/188,579, filed on Nov. 9, 1998.

(51) Int. Cl.⁷ ............................... C12Q 1/68; C12N 1/19; C12N 1/15
(52) U.S. Cl. ................. 435/6; 435/254.2; 435/254.11
(58) Field of Search .................................. 435/6, 254.11, 435/254.2

(56) References Cited
PUBLICATIONS

Ho et al., "Genetic, Physical, and Functional Interactions between the Triphosphatase and Guanylyltransferase Components of the yeast mRNA Capping Apparatus", Molecular ane Cellular Biology, vol. 18 (9), pp. 5189–5198, Sep. 1998.*

Yamada–Okabe et al., "Isolation and characterization of the *Candida albicans* gene for mRNA triphosphatase", FEBS Letters, 435(1), pp. 49–54, 1998.*

* cited by examiner

*Primary Examiner*—Jeffrey Fredman
*Assistant Examiner*—Arun K. Chakrabarti
(74) *Attorney, Agent, or Firm*—Benjamin Aaron Adler

(57) ABSTRACT

This invention provides methods for the discovery of molecules that target an essential aspect of eukaryotic gene expression—the formation of the mRNA 5' cap m7GpppN. An underlying principle of this invention is the use of a different strains of a test organism that differ only in the composition or source of the essential cap-forming enzymes. The invention provides isogenic yeast strains that derive all their capping activities from fungal sources versus mammalian sources. These strains form the basis of a differential growth inhibition assay to identify molecules that specifically target the fungal capping apparatus. This invention also provides a method to screen in vitro for molecules that inhibit fungal RNA triphosphatase, an essential enzyme that catalyzes the first of three steps in cap synthesis.

21 Claims, 31 Drawing Sheets

| | I * * * | | | III * * | | | IIIa * * | |
|---|---|---|---|---|---|---|---|---|
| Sce | KTDGLR | SEQ ID NO: 1 | 51 | TLLDGELV | SEQ ID NO: 2 | 12 | RYLMFDCLAING | SEQ ID NO: 3 | 66
| Spo | KSDGIR | SEQ ID NO: 7 | 48 | TLLDGELV | SEQ ID NO: 8 | 11 | RYLVFDCLACDG | SEQ ID NO: 9 | 67
| Cal | KTDGLR | SEQ ID NO: 13 | 48 | TLLDGELV | SEQ ID NO: 14 | 11 | RYVIFDALAIHG | SEQ ID NO: 15 | 68
| ChV | KTDGIR | SEQ ID NO: 19 | 38 | SIFDGELC | SEQ ID NO: 20 | 8 | AFVLFDAVVVSG | SEQ ID NO: 21 | 59
| Cel | KADGMR | SEQ ID NO: 25 | 37 | TLVDTEVI | SEQ ID NO: 26 | 14 | RMLIYDIMRFNS | SEQ ID NO: 27 | 68
| Mus | KADGTR | SEQ ID NO: 31 | 40 | TLLDGEMI | SEQ ID NO: 32 | 10 | RYLIYDIIKFNA | SEQ ID NO: 33 | 68
| ASF | KADGIR | SEQ ID NO: 37 | 30 | TILDGEFM | SEQ ID NO: 38 | 4 | EFYGFDVIMYEG | SEQ ID NO: 39 | 62
| Tbr | KADGLR | SEQ ID NO: 43 | 55 | FLLDTEVV | SEQ ID NO: 44 | 11 | DFIYFWGLDGRR | SEQ ID NO: 45 | 50
| Cfa | KVDGQR | SEQ ID NO: 49 | 51 | WMLDAELS | SEQ ID NO: 50 | 15 | DYVFFGGKQAKR | SEQ ID NO: 51 | 55
| Lef4 | KLDGMR | SEQ ID NO: 55 | 33 | VAFQCEVM | SEQ ID NO: 56 | 19 | NRTQYECGVNAS | SEQ ID NO: 57 | 53
| Vac | KTDGIP | SEQ ID NO: 61 | 32 | VVVFGEAV | SEQ ID NO: 62 | 3 | NWTVYLIKLIEP | SEQ ID NO: 63 | 54
| SFV | KTDGVG | SEQ ID NO: 67 | 32 | VTLYGEAV | SEQ ID NO: 68 | 4 | VWQIYLIKLITP | SEQ ID NO: 69 | 52
| MCV | KTDGVP | SEQ ID NO: 73 | 32 | VALFGEAV | SEQ ID NO: 74 | 6 | QLTVYLIKLMAP | SEQ ID NO: 75 | 52

Fig. 1A

|     | IV    |               |    | V           |               |     | VI       |               |
|-----|-------|---------------|----|-------------|---------------|-----|----------|---------------|
|     | **    |               |    | *  *        |               |     | *  * **  |               |
| Sce | DGLIF | SEQ ID NO: 4  | 15 | LLKWK--PEQENTVD | SEQ ID NO: 5  | 105 | WEMLRFRDDK | SEQ ID NO: 6  |
| Spo | DGLIF | SEQ ID NO: 10 | 14 | LLKWK--PKEMNTID | SEQ ID NO: 11 | 71  | WRFLRFRDDK | SEQ ID NO: 12 |
| Cal | DGLIY | SEQ ID NO: 16 | 14 | LLKWK--PAEENTVD | SEQ ID NO: 17 | 84  | WEMLRFRNDK | SEQ ID NO: 18 |
| ChV | DGLII | SEQ ID NO: 22 | 14 | LFKLK--PGTHHTID | SEQ ID NO: 23 | 44  | WKYIQGRSDK | SEQ ID NO: 24 |
| Cel | DGLIF | SEQ ID NO: 28 | 14 | VLKWL--PPSHNSVD | SEQ ID NO: 29 | 61  | WKFMRERTDK | SEQ ID NO: 30 |
| Mus | DGLIF | SEQ ID NO: 34 | 13 | ILKWK--PPSLNSVD | SEQ ID NO: 35 | 55  | WVFMRQRIDK | SEQ ID NO: 36 |
| ASF | DGIIL | SEQ ID NO: 40 | 11 | TFKWK--PTWDNTLD | SEQ ID NO: 41 | 104 | WEIVKIREDR | SEQ ID NO: 42 |
| Tbr | DGLIF | SEQ ID NO: 46 | 13 | LIKWK--PVHLCTVD | SEQ ID NO: 47 | 80  | WTFRNARNDK | SEQ ID NO: 48 |
| Cfa | DGLVF | SEQ ID NO: 52 | 13 | LLKWK--PLSLCTAD | SEQ ID NO: 53 | 85  | WRLHRLRSDK | SEQ ID NO: 54 |
| Lef4| DGYVV | SEQ ID NO: 58 | 6  | YVKYKWMPTTELEYD | SEQ ID NO: 59 | 39  | INVLKHRRDR | SEQ ID NO: 60 |
| Vac | EGVIL | SEQ ID NO: 64 | 10 | DFKIKK----ENTID | SEQ ID NO: 65 | 86  | GEILKPRIDK | SEQ ID NO: 66 |
| SFV | EGVVL | SEQ ID NO: 70 | 9  | DYKIKL----DNTTD | SEQ ID NO: 71 | 86  | GEILKPRIDK | SEQ ID NO: 72 |
| MCV | EGVVL | SEQ ID NO: 76 | 9  | DLKLKR----DNTVD | SEQ ID NO: 77 | 86  | GRLLRPRLAK | SEQ ID NO: 78 |

```
          Motif P           I
          * *               *  *
sce  FPGSQPVSFQHSDVEEKLLAHDYYVCEKTDGLRVLMFIVINPVTGEQ-GCFMIDRENNYYLV
cal  FPGSQPVSFERRHLEETLMQKDYVVCEKTDGLRCLLFLINDPDKGE--GVFLVTRENDYYFI
spo  FPGSQPVSFSKKHLQ-ALKEKNYFVCEKSDGIRCLLYMTEHPRYENRPSVYLFDRKMNFYHV
mus  FPGAQPVSMDKQNIRL-LEQKPYKVSWKADGTRVMMLIDG------TNEVFMIDRDNSVFH-
cel  FPGLQPVSLSRGNINL-LEQESYMVSWKADGMRYIIYIND------GDVYAFDRDNEVF-E
chv  LPGPNPVSIERKDF-EKLKQNKYVVSEKTDGIRFMFFTRVF--GF-KVCTIIDRAMTVYLL
                                                              ▲
                 III                              IIIa
                 *  *                             *  *
sce  NGFRFPRLPQKKEELLETLQDGTLLDGELVIQ----TNPMTKLQELRYLMFDCLAINGRCLT
cal  PNIHFP-LSVNETREKP-TYHHGTLLDGELVLE----NRNVSEPVLRYVIFDALAIHGKCII
spo  EKIFYPVEND----KSGKKYHVDTLLDGELVLD---IYPGGKKQ-LRYLVFDCLACDGIVYM
mus  VSNLEFPF-----RKDLRMHLSNTLLDGEMIIDKV--NGQAV--PRYLIYDIIKFNAQPVG
cel  IENLDFVT------KNG-APLMETLVDTEVIIDKVEINGAMCDQ-PRMLIYDIMRFNSVNVM
chv  PFKNIPR---------VLFQGSIFDGELCVDIVE----KK-FAFVLFDAVVVSGVTVS
                                   ▲                            ▲ sce  QSPTSSRLAHLGKEFFKPYFDLRAAYPNRCTT--FPFFKISMKHMDFSYQLVKVAKSL--DKLPH
cal  DRPLPKRLGYITENVMKPFDNFKKHNPDIVNSPEFPFKVGFKTMLTSYHADDVL-SKM-DKLFH
spo  SRLLDKRLGIFAKSIQKPLDEYTKTHMRETAI--FPFLTSLKKMELGHGILKLFN-EVIPRLRH
mus  DCDFNIRLQCIEREIISPRHEKMKTGLIDKTQEPFSVRPKQFFDINI--SRKLLEGNFAKEVSH
cel  KEPFYKRFEIIKTEIIDMRTAAFKTGRLKHENQIMSVRRKDFYDLEA--TAKLFGPKFVQHVGH
chv  QMDLASRFFAMKRSLKEFKNV-----PE--DPAILRYKEWI-PLEHPTIIKDHLK-K-ANAIYH
                                    ▲
              IV                       V
              * *                      *  *  *
sce  LSDGLIFTPVKAPYTAGGKDSLLLKWKPEQENTVDFKLILDIPMVEDPSLPKDDRNRWYNY
cal  ASDGLIYTCAETPYVFG-TDQTLLKWKPAEENTVDFQLEFVFNEVQDPDLDERDPTSTYLDY
spo  GNDGLIFTCTETPYVSG-TDQSLLKWKPKEMNTIDFMLKLEFAQPEEGDI--------DY
mus  EMDGIIFQPI-GKYKPG-RCDDILKWKPPSLNSVDFRLKITRMGG-EGLL-----------
cel  EIDGLIFQPKKTKYETG-RCDKVLKWKPPSHNSVDFLLKVEKKC-KEGML-----------
chv  -TDGLIIMSVDEPVIYG-RNFNLFKLKPGTHHTIDFIIMSE----DGTI------------
           ▲                ▲ ▲   ▲
```

```
sce  DVKPVFS-LYVWQGGADVNSRLKHFDQPFDRKEFEILERTYRKFAELSVSDEEWQNLKNLEQP
cal  DAKPNLIKLRVWQGS-NV---------HTD------------------FAKLDLSDDDWERLKALEQP
spo  SAMPEFQ-LGVWEG---------------------------------RNMYSFFAFMVDEKEWEKLLKSFNVP
mus  ---------PQNVG---------------------------------LLYVGGYERPFAQIKVTKELKQYDN-
cel  ---------PEWIG---------------------------------YLFVQNLSDPFGTMKATATLKKYHN-
chv  ---------GIFDP---------------------------------NLRKNVPVGKLDGYYN-
                                                                    *
                          VI    *  **           *
sce  LNGRIVECAK--NQET--GAWEMLRFRDDKLNGNHTSVVQKVLESINDSVSLEDLEE
cal  LQGRIAECR---QSTTKKGYWEMLRFRNDKSNGNHISVVEKILVSIKDGVKEKEVIE
spo  LSERIVECYL--DDEN--RWRFLRFRDDKRDANHISTVKSVLQSIEDGVSKEDLLK
mus  --KIIECKF--ENNS----WVFMRQRIDKSFPNAYNTAMAVCNSISNPVTKEMLFE
cel  --KIIECTLLVDNQGRPKEWKFMRERTDKSLPNGLRTAENVVETMVNPVTETYLIE
chv  -KGSIVECGF-AD-----GTWKYIQGRSDKNQAINDRLTYEKTLLNIEENITIDELLD Motif Vc sce  SEQ ID NO: 79
cal  SEQ ID NO: 80
spo  SEQ ID NO: 81
mus  SEQ ID NO: 82
cel  SEQ ID NO: 83
chv  SEQ ID NO: 84
```

Fig. 2B

```
Baculo    MFPARWHNYLQCGQVIKDSNLICFKTPLRPELFAYVTSEED-VWTAEQIVKQ----NPS
Mus CE    MAYNKIPPRWLNCPRRGQPVAGR-FLPLKTMLGPRYDSQV-AEEN-RFHPSMLSNYLKSLKVK
Cel CE    MGLPDRWLHCPKTGTLINNL-FFPFKTPLCKMYDNQI-AERRYQFHPAEVFSHPHLHGKK Baculo    IGAIIDLTNTSKYYDGVHFLRAGLLYKKIQVPGQTLPP-ESIVQEFIDTVKEFTEKC
Mus CE    MSLLVDLTNTSRFYDRNDIEKEGIKYIKLQCKGHGECPTTENTETFIRLCERFNERS
Cel CE    IGLWIDLTNTDRYYFREEVTEHECIYHKMKMAGRGVSPTQEDTDNFIKLVQEFHKKY Baculo    PGMLVGVHCTHGINRTGYMVCRYLMHTLGIAPQEAIDRFEKARGHKIERQNYVQDLLI
Mus CE    PPELIGVHCTHGFNRTGFLICAFLVEKMDWSIEAAVATFAQARPPGIYKGDYLKELFR
Cel CE    PDRVVGVHCTHGFNRTGFLIAAYLFQVEEYGLDAAIGEFAENRQKGIYKQDYIDDLFA
                ↑
           Active Site Baculo    SEQ ID NO: 85
Mus CE    SEQ ID NO: 86
Cel CE    SEQ ID NO: 87
```

Fig. 3A abd         MSTKPEKPIWMSQEDYDRQYGSITGDESSTV------------
hcm    MANSAKAEEYEKMSLEQAKASVNSET-ESSFNINENTTASGTGL abd    SKKDS---KVTANAPGDGNGSLPVLQSSSILTSKVS-----DLPI--------EAESGFKIQKRRHERYDQEERLRKQR
hcm    SEKTSVCRQVDIARKRKEFEDDLVKESSSCGKDTPSKKRKLDPEIVPEEKDCGDAEGNSKKRKRETEDVPKDKSSTGDG abd    AQKLREEQLKRH-EIEMTANRSINVDQIVREHYNERTIIANRAKRNLSPIIKLRNFNNAIKYMLI-DKYTKP-------
cel    MMKEVLDAFRKSGEAEGFG-HNKMSSSEVASHYNKVLQVGIEGRKE-SRIFFMRNMNMWVKSQLINDA----KQRVNDN
hcm    TQNKRKIALEDV--PEKQKNLEEGHSSTVAAHYNELQEVGLE-KRSQSRIFYLRNFNNWMKSVLIGEFLEKVRQKKKRD abd    ---GDVVLELGCCGKGGDLRKYGAAGISQFIGIDISNASIQEAHKRYRSMRNLDYQVVLITGD-CFGESLGVAVEPFPDC
cel    GVNNPRVLDLACGKGGDLKKWDIAGAKDVVMADVADVSIQQAEERYKQMFGYKKN-NIFTVQFIVADCTKENLEDRIEN
hcm    ----ITVLDLGCGKGGDLLRMKKGRINKLVCTDIADVSVKQCQQRYEDMKNRRDSEYIFSAEFITADSSKELLIDKF--

Fig. 5A

```
abd  RFP---CDIVSTQPCLHYAFETEEKARRALLNVAKSLKIGGHFFGTIPDSEFIRYKLNKFPKEVEKPSWGNSIYKVTFE
cel  RDP---EDDVSQQFALHLASFVDEASARFLKNAVGMEKPGGVFIGTIPDADRIVWSM----RNGENGQFANEVCKITYE
hcm  RDPQMCFDICSCQPVCHYSFESYEQADMLRNACERLSPGGYFIGTTPNSFELIRRL----EASETESFGNEIYTVKFQ abd  NNSYQKNDYEFTSP-YGQMYTWLEDAIDNVPEYVVPFETLRSLADEYGLELVSQMPFNKFFVQEIPKWIERF------
cel  N---VEELAEGKVPLFGAKFHFSLDE-QVNCPEFLAYFPLVKHLLEELDMELLFVHNF----AEAINKWLEPGRRLLES
hcm  K------KGDYPLFGCKYDENLEG-VVDVPEFLVYFPLLNEMAKKYNMKLVYKKTFLEFYEEKINNENKMLLKRMQA abd  ------SPKMREGLQRSDGRYGVEG------DEKEAA------SYF-----YTMFAFRKVKQYI-----EPESVKPN*
cel  MTGLETYPNEKLSGKSDDEYLEAKAKLDAFPEDERIKTMGTLSKSEWEAICMYLVFGFRKKKSEAEKTEEEPATTKPVA
hcm  LEPYPANESSKLVSEKVDDY-EHAAKY-MKNSQVRL-PLGTLSKSEWEATSIYLVFAFEKQQ* abd  SEQ ID NO: 112
cdl  SEQ ID NO: 113
hcm  SEQ ID NO: 114
```

Fig. 5B

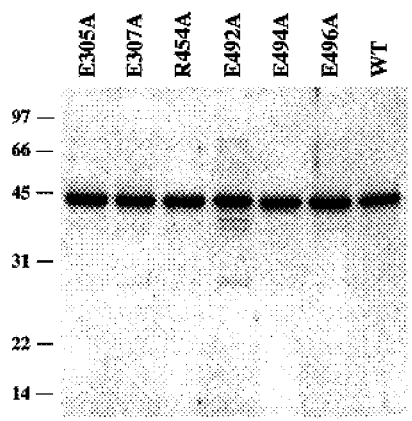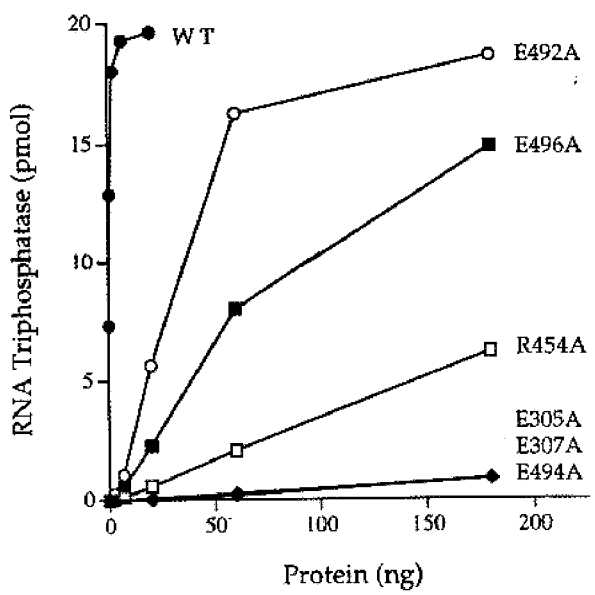
Fig. 6A
Fig. 6B

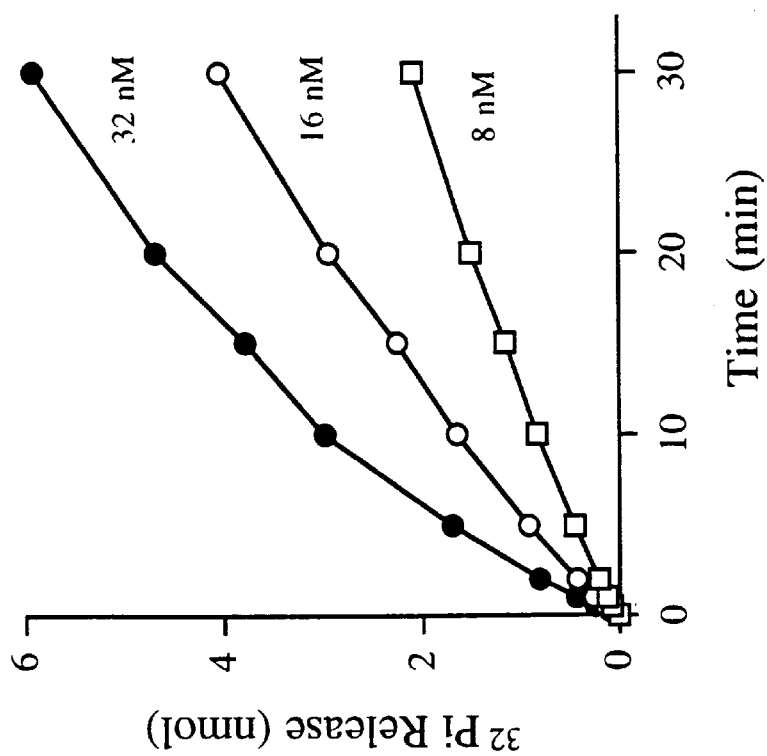
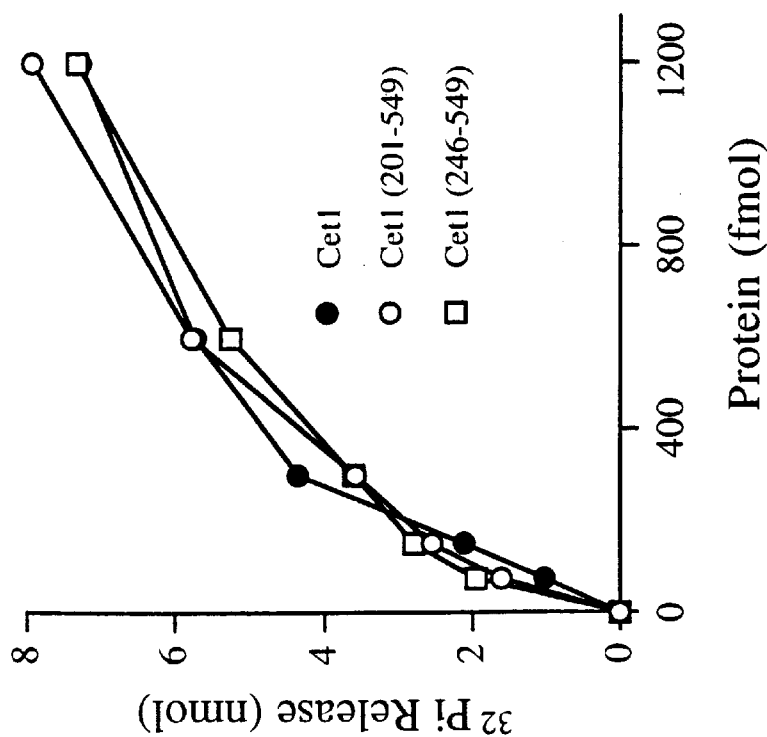
Fig. 8A
Fig. 8B

MSTDSYTPSQEPGSKRLKTGESVPARRGVSPSTGGVASAYGNESEKKPSWLQTNKSKIDG

KYDKYGERRNAHTTTRDSRLDRLKRVRQKLAEREDVGHEGDEGDEDEGILPYIHLQAANP

AIIHNEKQENYRKFQSRISNRENRDINSIVRAHYNQRTQQAKQQGSRVNSPIYKMRNFNN

AIKYILLGNWAKHNPEELDLFSFLDLCCGKGGDLNKCQFIGIDQYIGIDIADLSVKEAFE

RYTKQKARFRHSNQNSNRYTFEACFATGDCFTQFVPDILEPNGPGIIERAFPVDIVSAQF

SLHYSFESEEKVRTLLTNVTRSLRSGGTFIGTIPSSDFIKAKIVDKHLQRDEKGKAKFGN

SLYSVTFEKDPPEDGVFRPAFGNKYNYWLKDAVDNVPEYVVPFETLRSLCEEYDLVLKYK

KSFTDIFNQEIPKYFSKLNKNLIDGMKRSDGKYGAEGDEKEAVAFYIGFVFEKV

SEQ ID NO: 116

Fig. 14C

```
Sc  (225)  DLEVLNEISASSKPSKYRNVPIWAQKWKPTIKALQSINVKD  (265)
           ::   .  . :  ::  .:   :::::.:  :   .  .   ::  :
Ca  (186)  DLTKIKKLKQSKKPRRYETPPIWAQRWVPPNRQKEETNVDD  (226)
```

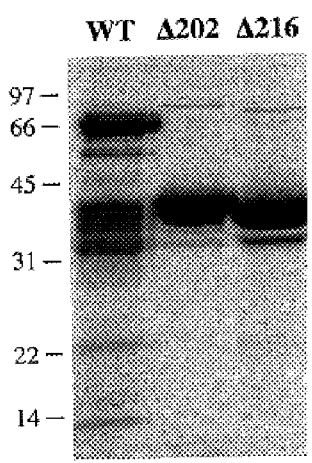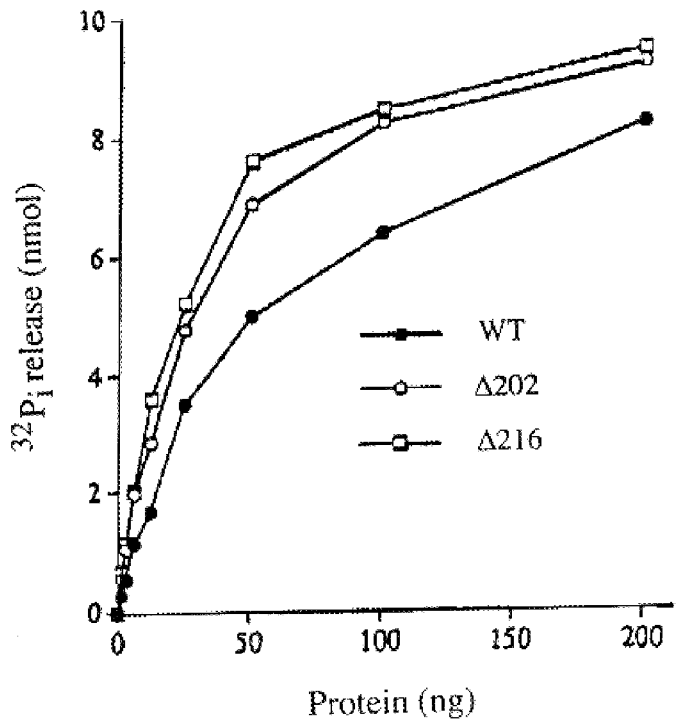
Fig. 21B
Fig. 21A

PHARMACOLOGICAL TARGETING OF MRNA CAP FORMATION

CROSS-REFERENCE TO RELATED APPLICATION

This application is a continuation-in-part of U.S. Ser. No. 09/188,579, filed Nov. 9, 1998.

FEDERAL FUNDING LEGEND

This invention was created using federal funds under Grant No. GM-52470 from the National Institutes of Health. Accordingly, the United States Government has certain rights in the invention.

BACKGROUND OF THE INVENTION

1. Field of the Invention

The present invention relates generally to the fields of gene biochemical pharmacology and drug discovery. More specifically, the present invention relates to method of screening for a compound that inhibits formation of an organism's 5' mRNA cap structure.

2. Description of the Related Art

Processing of eukaryotic mRNA in vivo is coordinated temporally and physically with transcription. The earliest event is the modification of the 5' terminus of the nascent transcript to form the cap structure m7GpppN. The cap is formed by three enzymatic reactions: (i) the 5' triphosphate end of the nascent RNA is hydrolyzed to a diphosphate by RNA 5' triphosphatase: (ii) the diphosphate end is capped with GMP by GTP:RNA guanylyltransferase; and (iii) the GpppN cap is methylated by AdoMet:RNA (guanine-N7) methyltransferase [1].

RNA capping is essential for cell growth. Mutations of the triphosphatase, guanylyltransferase, or methyltransferase components of the yeast capping apparatus that abrogate catalytic activity are lethal in vivo [2-12]. Genetic and biochemical experiments highlight roles for the cap in protecting mRNA from untimely degradation by cellular 5' exonucleases [13] and in recruiting the mRNA to the ribosome during translation initiation [14].

The physical and functional organizations of the capping apparatus differ in significant respects in fungi, metazoans, protozoa, and viruses. Hence, the cap-forming enzymes are potential targets for antifungal, antiviral, and antiprotozoal drugs that would interfere with capping of pathogen mRNAs, but spare the mammalian host capping enzymes. A plausible strategy for drug discovery is to identify compounds that block cell growth contingent on pathogen-encoded capping activities without affecting the growth of otherwise identical cells bearing the capping enzymes of the host organism. For this approach to be feasible, the capping systems of interest must be interchangeable in vivo.

The architecture of the capping apparatus differs between metazoans, fungi, protozoa, and DNA viruses. Metazoan species encode a two-component capping system consisting of a bifunctional triphosphatase-guanylyltransferase polypeptide (named Mce1p in the mouse and Hce1p in humans) and a separate methyltransferase polypeptide (Hcm1p in humans) [6, 9, 15-22]. The budding yeast *Saccharomyces cerevisiae* encodes a three component system consisting of separate triphosphatase (Cet1p), guanylyltransferase (Ceg1p), and methyltransferase (Abd1p) gene products [7, 10, 11, 23]. In yeast, the triphosphatase (Cet1p) and guanylyltransferase (Ceg1p) polypeptides interact to form a heteromeric complex [11], whereas in mammals, autonomous triphosphatase and guanylyltransferase domains are linked in cis within a single polypeptide (Mce1p) [18].

Vaccinia virus capping enzyme is a multifunctional protein that catalyzes all three reactions. The triphosphatase, guanylyltransferase, and methyltransferase active sites are arranged in a modular fashion within a single polypeptide—the Vaccinia D1 protein [24-30]. Other DNA viruses encode a subset of the capping activities; e.g., baculoviruses encode a bifunctional triphosphatase-guanylyltransferase (LEF-4) and Chlorella virus PBCV-1 encodes a monofunctional guanylyltransferase [31-33]. The guanylyltransferase and methyltransferase domains are conserved between DNA viruses, fungi, and metazoans. In contrast, the triphosphatase components are structurally and mechanistically divergent.

RNA Guanylyltransferase—Transfer of GMP from GTP to the 5' diphosphate terminus of RNA occurs in a two-step reaction involving a covalent enzyme-GMP intermediate [34]. Both steps require a divalent cation cofactor, either magenesium or manganese.

The GMP is covalently linked to the enzyme through a phosphoamide (P—N) bond to the epsilon-amino group of a lysine residue within a conserved KxDG element (motif I) found in all known cellular and DNA virus-encoded capping enzymes (FIG. 1). Five other sequence motifs (III, IIIa, IV, V, and VI) are conserved in the same order and with similar spacing in the capping enzymes from fungi, metazoans, DNA viruses, and trypanosomes (FIG. 1) [35].

Hakansson et al. [36] have determined the crystal structure of the Chlorella virus capping enzyme in the GTP-bound state and with GMP bound covalently. The protein consist of a larger N-terminal domain (domain 1, containing motifs I, III, IIIa, and IV) and a smaller C-terminal domain (domain 2, containing motif VI) with a deep cleft between them. Motif V bridges the two domains. Motifs I, III, IIIa, IV, and V form the nucleotide binding pocket. The crystal structure reveals a large conformational change in the GTP-bound enzyme, from an "open" to a "closed" state, that brings motif VI into contact with the beta and gamma phosphates of GTP and reorients the phosphates for in-line attack by the motif I lysine. When the crystal is soaked in manganese, guanylyltransferase reaction chemistry occurs in crystallo and the covalent enzyme-GMP intermediate is formed. However, only the enzyme in the closed conformation is reactive.

Identification of essential enzymic functional groups has been accomplished by site-directed mutagenesis of Ceg1p, the RNA guanylyltransferase of *Saccharomyces cerevisiae*. The guanylyltransferase activity of Ceg1p is essential for cell viability. Hence, mutational effects on Ceg1p function in vivo can be evaluated by simple exchange of mutant CEG1 alleles for the wild type gene. The effects of alanine substitutions for individual amino acids in motifs I, III, IIIa, IV, V, and VI [2, 5, 6] have been examined. Sixteen residues were defined as essential (denoted by asterisks in FIG. 1) and structure-activity relationships at these positions were subsequently determined by conservative replacements. Nine of the essential Ceg1p side chains correspond to moieties which, in the Chlorella virus capping enzyme crystal structure, make direct contact with GTP (arrowheads in FIG. 2). These include: the motif I lysine nucleophile which contacts the alpha-phosphate of GTP; the motif I arginine and motif III glutamate, which contact the 3' and 2' ribose hydroxyls, respectively; the motif III phenylalanine, which stacks on the guanine base; the two motif V lysines, which contact the alpha-phosphate; the motif V aspartate, which interacts with the beta-phosphate; the motif VI arginine that interacts with the beta-phosphate; and the motif VI lysine, which contacts the gamma-phosphate of GTP [6, 36].

On the basis of sequence conservation outside motifs I, III, IIIa, IV, V, and VI, the capping enzymes of fungi (*S. cerevisiae, S. pombe, C. albicans,*), metazoans (*C. elegans* and mammals) and Chlorella virus can be grouped into a discrete subfamily [6, 37]. The sequence alignment in FIG. 2 highlights two motifs that are present in these capping enzymes, but not in the poxvirus enzymes, which can be designated motif P and motif Vc. In the Chlorella virus capping enzyme, motif P forms one wall of the guanosine binding pocket of domain 1 [36]. Motif Vc—(K/R)I(I/V)EC—is situated between motifs V and VI in domain 2. The glutamate residue of motif Vc is essential for the activity of the fungal guanylyltransferase Ceg1p [37].

RNA Triphosphatase—There are at least two mechanistically and structurally distinct classes of RNA 5' triphosphatases: (i) the divalent cation-dependent RNA triphosphatase/NTPase family (exemplified by yeast Cet1p, baculovirus LEF-4, and vaccinia D1), which require three conserved collinear motifs (A, B, and C) for activity [12, 28, 31, 32], and (ii) the divalent cation-independent RNA triphosphatases, e.g., the metazoan cellular enzymes and the baculovirus enzyme BVP [15, 17, 38-40], which require the HCxAGxGR(S/T)G phosphate-binding motif. The existence of additional classes of RNA 5'-triphosphatases is likely, given that the candidate capping enzymes of several RNA viruses and trypanosomatid protozoa lack the defining motifs of the two known RNA triphosphatase families [41, 42]. Hence, the triphosphatase components of the capping apparatus provide attractive targets for the identification of specific antifungal, antiviral, and antiprotozoal drugs that will block capping of pathogen mRNAs, but spare the mammalian host enzyme.

Mammalian RNA Triphosphatase—Metazoan capping enzymes consist of an N-terminal RNA triphosphatase domain and a C-terminal guanylyltransferase domain. In the 496-amino acid mouse enzyme Mce1p, the two catalytic domains are autonomous and nonoverlapping [18]. The metazoan RNA triphosphatase domains contain a (I/V)HCx AGxGR(S/T)G signature motif initially described for the protein tyrosine phosphatase/dual-specificity protein phosphatase enzyme family. These enzymes catalyze phosphoryl transfer from a protein phosphomonoester substrate to the thiolate of the cysteine of the signature motif to form a covalent phosphocysteine intermediate, which is then hydrolyzed to liberate phosphate (FIG. 3). The metazoan capping enzymes hydrolyze the phosphoanhydride bond between the beta and gamma phosphates of triphosphate-terminated RNA; they are not active on nucleoside triphosphates. The conserved cysteine of the signature motif is essential for RNA triphosphatase function [11, 15, 38, 39]. A characteristic of the cysteine-phosphatases is their lack of a requirement for a divalent cation cofactor.

The N-terminal portion of Mce1p from residues 1-210 is an autonomous RNA triphosphatase domain [18]. Recombinant Mce1(1-210)p has been expressed in bacteria and purified to near-homogeneity. Mce1(1-210)p sediments in a glycerol gradient as a discrete peak of 2.5 S, indicating that the domain is monomeric in solution. The RNA triphosphatase activity of Mce1(1-210)p can be assayed by the release of $^3$Pi from $\gamma^{32}$P-labeled poly(A). A kinetic analysis showed that the initial rate of Pi release was proportional to enzyme concentration. Mce1(1-210)p hydrolyzed 1.2 to 2 molecules of Pi per enzyme per second at steady state. RNA triphosphatase activity was optimal in 50 mM Tris buffer at pH 7.0 to 7.5. Activity was optimal in the absence of a divalent cation and was unaffected by EDTA. Inclusion of divalent cations elicited a concentration dependent inhibition of RNA triphosphatase activity. 75% inhibition was observed at 0.5 mM $MgCl_2$ or $MnCl_2$. Mce1(1-210) did not catalyze release of $^{32}$Pi from $[\gamma^{32}P]ATP$.

Metal-dependent RNA Triphosphatases—The RNA triphosphatases of *S. cerevisiae* and DNA viruses are structurally and mechanistically unrelated to the metazoan RNA triphosphatases. The vaccinia virus RNA triphosphatase depends absolutely on a divalent cation cofactor. Vaccinia triphosphatase displays broad specificity in its ability to hydrolyze the gamma phosphate of ribonucleoside triphosphates, deoxynucleoside triphosphates, and triphosphate-terminated RNAs [43, 44]. The NTPase and RNA triphosphatase reactions occur at a single active site within an 545-amino acid N-terminal domain of vaccinia capping enzyme that is distinct from the guanylyltransferase active site [27-30]. The vaccinia RNA triphosphatase is optimal with magnesium, is 12% as active in manganese, and is inactive with cobalt [43]. In contrast, the vaccinia NTPase is fully active with cobalt, manganese, or magnesium [43, 44]. Baculovirus LEF-4 hydrolyzes the g phosphate of RNA and NTPs; the LEF-4 NTPase is activated by manganese or cobalt, but not by magnesium [31].

The yeast RNA 5'-triphosphatase Cet1p also hydrolyzes the gamma phosphate of nucleoside triphosphates [12]. The NTPase of Cet1p is activated by manganese and cobalt. This is a property shared with the triphosphatase components of the vaccinia D1 and baculovirus LEF-4 capping enzymes. Recent studies illuminate a common structural basis for metal-dependent catalysis by these enzymes. The metal-dependent RNA triphosphatases share 3 collinear sequence motifs, designated A, B, and C (FIG. 4). These are present in yeast Cet1p, in the Cet1p homolog from yeast *Candida albicans*, in the triphosphatase-guanylyltransferase domains of the vaccinia virus, Shope fibroma virus, molluscum contagiosum virus, and African swine fever virus capping enzymes, and in baculovirus LEF-4. Mutational analysis identified several residues within these motifs that are essential for the RNA triphosphatase and ATPase activities of vaccinia virus capping enzyme; the essential residues include two glutamates in motif A, an arginine in motif B, and two glutamates in motif C [28]. Alanine substitutions at any of these positions in the vaccinia capping enzyme reduced phosphohydrolase specific activity by 2 to 3 orders of magnitude. These 5 residues may comprise part of the triphosphatase active site. All five residues essential for vaccinia triphosphatase activity are conserved in LEF-4 and Cet1p. Mutations of the equivalent residues of Cet1p result in loss of triphosphatase activity [12].

Physical Association of the Triphosphatase and Guanylyltransferase Components of the Capping Apparatus—Yeast and mammals use different strategies to assemble a bifunctional enzyme with triphosphatase and guanylyltransferase activities. In yeast, separate triphosphatase (Cet1p) and guanylyltransferase (Ceg1p) enzymes interact to form a heteromeric complex, whereas in mammals, autonomous triphosphatase and guanylyltransferase domains are linked in cis within a single polypeptide (Mce1p).

Cet1p and Ceg1p Form a Heterodimeric Capping Enzyme Complex In Vitro.—The native size of purified recombinant yeast RNA triphosphatase Cet1p was gauged by glycerol gradient sedimentation. Cet1p sedimented as a single component of 4.3 S. The yeast guanylyltransferase Ceg1p sediments similarly in a glycerol gradient. Yet, when equal amounts of recombinant Cet1p and Ceg1p were mixed in buffer containing 0.1 M NaCl and the mixture was analyzed by glycerol gradient sedimentation, the two proteins, as well as the triphosphatase and guanylyltransferase activities, cosedimented as a single discrete peak of 7.5 S. Thus, Ceg1p and Cet1p interact in vitro to form a heteromeric complex [11]. Cet1p does not form a complex with the structurally homologous RNA guanylyltransferase domain of the mouse capping enzyme. Recombinant mouse guanylyltransferase, Mce1(211-597)p, was purified to homogeneity, mixed with Cet1p or with a buffer control, and then subjected to sedimentation analysis in parallel with the Cet1-Ceg1 mixtures. The 45 kDa Mce1(211-597) protein alone sedimented as a single monomeric peak [18]. Sedimentation of the Mce1(211-597)p plus Cet1p mixture revealed no shift in the distribution of the mouse guanylyltransferase or the yeast triphosphatase to a more rapidly sedimenting form [11]. Hence, yeast RNA triphosphatase forms a heteromeric complex in vitro with yeast guanylyltransferase, but not with the mammalian enzyme. Subsequent studies of the *Candida albicans* RNA triphosphatase (named CaCet1p) showed that it could interact with *S. cerevisiae* guanylyltransferase Ceg1p in vivo as gauged by a two-hybrid reporter assay [45].

Cet1p-Ceg1p Heterodimerization is Essential In Vivo—Truncated proteins Cet1(201-549)p and Cet1(246-549)p were expressed in bacteria and purified from soluble bacterial lysates by Ni-agarose and phosphocellulose column chromatography. Purified Cet1(201-549)p and Cet1(246-549)p catalyzed the release of $^{32}Pi$ from $\gamma^{32}P$-labeled triphosphate-terminated poly(A) or $[\gamma^{32}P]ATP$ with the same specific activity as full-length Cet1p [11]. The CET1 (201–259) gene in single copy was functional in vivo in supporting yeast cell growth [11]. The finding that the CET1(246-549) gene on a CEN plasmid could not support cell growth, even though the gene product has full RNA triphosphatase activity in vitro, suggests that the catalytic activity of Cet1p, though essential for cell growth (see below), may not suffice for Cet1p function in vivo. Glycerol gradient analysis showed that Cet1(201-549)p by itself sedimented as a discrete species of ~4.1 S. When Cet1(201-549)p was mixed with Ceg1p and the mixture was analyzed by glycerol gradient sedimentation, the two proteins cosedimented as a 6.8 S heteromeric complex [11]. The more extensively truncated Cet1(246-549)p did not sediment as a discrete species like full-sized Cet1p and Cet1(201–549)p. Rather, most of the Cet1(246-549)p sedimented as a high molecular weight oligomer (~13 S) that retained RNA triphosphatase activity. When a mixture of Cet1(246-549)p and Ceg1p was sedimented most of the Cet1(246-549)p remained aggregated; only a minor fraction of the input Ceg1p was shifted to the size expected for the heteromeric complex. Deletion from residues 201-245 (which results in loss of function in vivo despite retention of triphosphatase activity in vitro) affects the interaction of Cet1p with Ceg1p.

The implication of these data is that the interaction of Cet1p with Ceg1p is essential for yeast cell growth. Pharmacological interference with Ceg1p-Cet1p heterodimerization is a potential mechanism for blocking gene expression in fungi without impacting on mammalian cells.

Cap Methyltransferase—The enzyme RNA (guanine-N7-) methyltransferase (referred to hereafter as cap methyltransferase) catalyzes the transfer of a methyl group from AdoMet to the GpppN terminus of RNA to produce m7GpppN-terminated RNA and AdoHcy [1]. The *Saccharomyces cerevisiae* cap methyltransferase is the product of the ABD1 gene [7]. ABD1 encodes a 436-amino acid polypeptide. A catalytic domain of Abd1p from residues 110 to 426 suffices for yeast cell growth (8, 9); this segment of Abd1p is homologous to the methyltransferase catalytic domain of the vaccinia virus capping enzyme [7]. A key distinction between the yeast and vaccinia virus cap methyltransferases is their physical linkage, or lack thereof, to the other cap-forming enzymes. The vaccinia virus methyltransferase active site is encoded within the same polypeptide as the triphosphatase and guanylyltransferase, whereas the yeast methyltransferase is a monomeric protein that is not associated with the other capping activities during fractionation of yeast extracts [7]. Mutational analyses of the yeast and vaccinia cap methyltransferases have identified conserved residues that are critical for cap methylation [8, 9, 46]. In the case of Abd1p, mutations that abolished methyltransferase activity in vitro were lethal in vivo.

A putative cap methyltransferase from *C. elegans* was identified on phylogenetic grounds [9]. An alignment of the sequence of the predicted 402-amino acid *C. elegans* protein (Genbank accession Z81038) with the yeast cap methyltransferase Abd1p is shown in FIG. 5. Although it remains to be demonstrated that the nematode protein has cap methyltransferase activity, the extensive sequence conservation suggested that other metazoans might also encode homologues of Abd1p. A human cDNA that encodes a bona fide cap methyltransferase has been identified and a physical and biochemical characterization of the recombinant human cap methyltransferase (Hcm1p) produced in bacteria was conducted. A functional C-terminal catalytic domain of Hcm1p was defined by deletion analysis [22].

Interaction of the Cellular Capping Apparatus with the Phosphorylated CTD of RNA Polymerase II. Cap formation in eukaryotic cells in vivo is targeted to the nascent chains synthesized by RNA polymerase II (pol II). A solution to the problem of how pol II transcripts are specifically singled out for capping has been described whereby the cellular capping enzymes are targeted to pre-mRNA by binding to the phosphorylated carboxyl-terminal domain (CTD) of the largest subunit of pol II [16-18, 47, 48]. The CTD, which is unique to pol II, consists of a tandem array of a heptapeptide repeat with the consensus sequence Tyr-Ser-Pro-Thr-Ser-Pro-Ser. The mammalian pol II large subunit has 52 tandem repeats whereas the *S. cerevisiae* subunit has 27 copies. The pol II largest subunit exists in two forms, a nonphosphorylated IIA form and a phosphorylated IIO form, which are interconvertible and functionally distinct. In vivo, the pol IIO enzyme contains as many as 50 phosphorylated amino acids (primarily phosphoserine) within the CTD. During transcription initiation, pol IIA is recruited to the DNA template by the general transcription factors. The pol IIA CTD undergoes extensive phosphorylation and conversion to IIO during the transition from preinitiation complex to stable elongation complex. Several CTD kinase activities have been implicated in CTD hyperphosphorylation, each of which contains a cyclin and cyclin-dependent kinase subunit pair. The cdk7 and cyclin H subunits of the general transcription factor TFIIH catalyze phosphorylation of Ser-5 of the CTD heptapeptide. Other CTD kinases include the cdk8/cyclin C pair found in the pol II holoenzyme, CTDK-I, a heterotrimeric kinase with cdk-like and cyclin-like subunits, and P-TEFb, a regulator of polymerase elongation with a cdc2-like subunit.

The recombinant *S. cerevisiae* and *Sc. pombe* guanylyltransferases Ceg1p and Pce1p bind specifically to the phosphorylated form of the CTD [16]. Moreover, recombinant yeast cap methyltransferase Abd1p also binds specifically to CTD-PO4 [16]. Phosphorylation at Ser-5 of the heptad repeat was sufficient to confer guanylyltransferase and methyltransferase binding capacity to the CTD [16]. This analysis has been extended to mammalian capping enzyme where the key finding is that the guanylyltransferase domain Mce1 (211-597)p by itself binds to CTD-PO4, whereas the triphosphatase domain Mce1(1-210)p does not [18]. These findings suggest that the mammalian RNA triphosphatase is targeted to the nascent pre-mRNA by virtue of its connection in cis to the guanylyltransferase. The phosphorylation-dependent interaction between guanylyltransferase and the CTD is conserved from yeast to mammals. It is not clear if the structural elements on the yeast and mammalian enzymes that interact with CTD-PO4 are conserved or divergent. Nonetheless, pharmacological interference with the binding of guanylyltransferase or cap methyltransferase to the CTD is a potential mechanism for blocking gene expression in fungi or mammalian cells. Such interference can occur either by direct blocking of capping enzyme/CTD-PO4 binding or indirectly by affecting the phosphorylation state of the CTD.

The prior art is deficient in the lack of methods of screening for a compound that inhibits formation of an organism's 5' mRNA cap structure. The present invention fulfills this longstanding need in the art.

SUMMARY OF THE INVENTION

The present invention facilitates the discovery of drugs that target an essential aspect of eukaryotic gene expression—the formation of the mRNA 5' cap m7GpppN. The underlying principle of the invention is the use of a different strains of a test organism that differ only in the composition or source of the essential cap-forming enzymes. For example, the construction of isogenic yeast strains that derive all their capping activities from fungal sources versus mammalian sources provides the basis to identify molecules that specifically target the fungal capping apparatus.

The methods disclosed herein test a battery of candidate molecules for their ability to selectively impair the growth of a strain containing capping enzymes differing in composition or source. In a simple embodiment of the invention, this would entail the local application of an array of candidate molecules to agar culture plates that had been inoculated with an engineered yeast strain containing capping enzymes differing in composition or source. The plates are incubated to permit growth of the yeast cells to form a confluent lawn. Growth inhibition by the applied compound is detected as a "halo" of no-growth or slow-growth around the site of application. The methods will necessarily detect many compounds that inhibit the growth of all test strains; these are regarded as non-specific to capping and would likely not be pursued. The positive candidates are those that inhibit growth of one strain, but not of an otherwise identical strain containing a capping apparatus that differs in composition or source. For example, molecules that inhibit the growth of yeast cells containing an all-fungal capping apparatus, but have little or no effect on the growth of yeast cells containing the mammalian capping apparatus, would be regarded as promising leads for antifungal drugs. Conversely, molecules that inhibit the growth of cells containing an all-mammalian capping apparatus, but have little or no effect on the growth of cells containing the fungal capping apparatus merit further consideration as specific inhibitors of capping in mammalian cells, with the potential for development as an antineoplastic agent.

The methods of the present invention are also applicable to the identification of potential antiviral agents and antiparasitic agents that specifically target virus-encoded or parasite-encoded capping enzymes. In this embodiment of the invention, the growth inhibition screen would include testing the array of candidate molecules against a strain that contains one or more virus-encoded or parasite-encoded capping activities in lieu of the endogenous enzyme(s). Molecules that selectively inhibit growth of the strain bearing the viral or parasite capping enzyme component, but not both of the strain bearing the mammalian capping apparatus, would be regarded as promising leads for further evaluation of antiviral or antiparasitic activity.

The invention is not restricted to the use of fungi as the test organisms. Advances in gene targeting in mammalian cells make it feasible to construct mammalian cell lines in which one or more of the genes encoding cellular capping activities is deleted and replaced by a gene encoding the analogous enzyme from another source. Thus, candidate cap-targeting compounds could be identified by screening in parallel for selective growth inhibition of one of several cell lines differing only in the composition or source of the capping apparatus. Eukaryotic viruses that depend on virus-encoded capping activities can also be developed as the targets for testing of growth inhibition. In this embodiment, a viral gene encoding an essential capping activity would be deleted and replaced by a gene encoding the analogous enzyme from another source. Virus plaque formation on permissive host cells provides an easy visual screen (by plaque number and plaque size) for inhibition of virus replication by candidate agents added to the medium. Agents that selectively inhibit the replication of virus containing capping enzymes from one source, but not from another source, are presumed to do so by selective targeting of cap formation.

The invention is also not restricted to identifying exogenous molecules that target cap formation. Another embodiment facilitates the DNA-based identification of natural or synthetic gene products that inhibit cell growth via intracellular effects on the capping enzymes. In this application of the invention, candidate genes or gene libraries (either natural or synthetic) would be transformed into a test yeast strain, e.g., a strain bearing an all-fungal capping apparatus. The genes in the library are under the control of a regulated promoter (e.g. a GAL promoter) so that their expression can be repressed (in glucose medium) or induced (in galactose medium) by the experimenter. The initial screen selects for library-transformed cells that grow on glucose, but are inhibited on galactose. Plasmids recovered from such cells would be clonally amplified in bacteria and then re-transformed in parallel into yeast strains containing the fungal capping apparatus and strains containing one or both mammalian capping enzymes. Plasmids that elicit galactose-dependent growth inhibition of the strain with the fungal capping system, but do not inhibit the strains with mammalian capping components, are good candidates to encode specific antagonists of fungal cap formation. Sequencing the plasmid encoded gene product will reveal the identity of the presumptive inhibitor. Structure-activity relationships for the gene product can then be delineated by DNA-based mutagenesis.

The growth-inhibiting molecules or genes identified using the methods described in this invention could conceivably target cap formation via a number of distinct mechanisms, including: (i) direct inhibition of the catalytic activity of one of the cap-forming enzymes by the identified molecule or a metabolite thereof; (ii) interference with protein-protein interactions required for in vivo function of one of the cap-forming enzymes; (iii) alterations in the level of available substrates for cap formation (e.g., GTP and AdoMet) or the level of endogenous inhibitors of cap formation (e.g., AdoHcy); and (iv) the synthesis of abnormal cap structures in the presence of the growth-inhibiting molecule (or metabolites thereof) that effectively "poison" cellular transactions dependent on the RNA cap.

An advantage of the present invention is that it is geared to detect specific targeting of capping enzymes in vivo based on differences in their composition or origin, without bias with respect to the mechanism of inhibition. Once candidate molecules are identified, further testing of growth inhibition of isogenic strains differing in one component of the capping system can reveal which enzyme is targeted. Further mechanistic studies can ensue using purified capping enzymes from the relevant sources.

The invention also encompasses an in vitro screen to identify candidate inhibitors of the catalytic activity of the fungal RNA 5' triphosphatase. The method exploits the fact that the yeast RNA triphosphatase Cet1p has a vigorous ATPase activity that depends on either manganese or cobalt as the divalent cation cofactor [12]. The method is simple, quantitative, and adaptable to a colorimetric detection assay that is suited to high-throughput screening for inhibitors.

BRIEF DESCRIPTION OF THE DRAWINGS

FIGS. 1A and 1B show the guanylyltransferase signature motifs. Six collinear sequence elements, designated motifs I, III, IIIa IV, V, and VI, are present in cellular and viral capping enzymes. The amino acid sequences are aligned for the enzymes of *S. cerevisiae* (Sce), *S. pombe* (Spo), *C. albicans* (Cal), Chlorella virus PBCV-1 (ChV), mouse (Mus), African swine fever virus (ASF), *Trypanosoma brucei gambiense* (Tbr), *Crithidia fasciculata* (Cfa), AcNPV baculovirus (Lef4), vaccinia virus (Vac), Shope fibroma virus (SFV), and molluscum contagiosum virus (MCV). The numbers of amino acid residues separating the motifs are indicated. The amino acids of the yeast enzyme motifs that are essential for Ceg1p function in vivo are denoted by asterisks.

FIGS. 2A and 2B show the conserved sequence elements in fungal, metazoan, and Chlorella virus mRNA capping enzymes. The amino acid sequence of the *S. cerevisiae* (sce) guanylyltransferase Ceg1p from residues 43 to 399 is aligned with the homologous regions of the guanylyltransferases encoded by *Candida albicans* (cal), *Schizosaccharomyces pombe* (spo), mouse (mus), *Caenorhabditis elegans* (cel), and Chlorella virus PBCV-1. Eight conserved collinear sequence elements, designated motifs P, I, III, IIIa IV, V, Vc, and VI, are shown in shaded boxes. Gaps in the sequence are indicated by dashes (-). Ceg1p residues defined by mutational analysis as essential for enzyme function in vivo are denoted by asterisks. Residues in proximity to GTP in the Chlorella virus capping enzyme-GTP co-crystal are indicated by arrowheads below the aligned sequences.

FIGs. 5A and 5B show the amino acid sequence conservation in human and yeast cap methyltransferases. The complete amino acid sequence of the 476-amino acid Hcm1p protein (hcm) is aligned with the complete sequence of yeast Abd1p (abd) and with the predicted 402-amino acid *C. elegans* C25A1.f gene product (cel) from residue 1 to 373. Gaps in the sequences are indicated by dashes (-). The C-termini of Hcm1p and Abd1p are indicated by asterisks. Residues in Hcm1p that are identical or similar in Abd1p or the *C. elegans* protein are shown in shaded boxes. Amino acids essential for Abd1p function are denoted by dots.

FIG. 6 shows the mutational effects on the RNA triphosphatase activity of Cet1(201-549)p. (FIG. 6A) Protein purification. Aliquots (3 μg) of the Ni-agarose preparations of recombinant wild type (WT) Cet1(201-549)p and the indicated Cet1(201-549)p-Ala mutants were electrophoresed through a 12% polyacrylamide gel containing 0.1% SDS. Polypeptides were visualized by staining with Coomassie blue dye. The positions and sizes (in kDa) of marker proteins are indicated on the left. (FIG. 6B) RNA triphosphatase activity. Reaction mixtures (10 μl) containing 50 mM Tris HCl (pH 7.5), 5 mM DTT, 1 mM $MgCl_2$, 20 pmol (of triphosphate termini) of $[\gamma^{32}P]$-poly(A), and either WT or mutant proteins as specified were a incubated for 15 min at 30° C. Aliquots of the mixtures were applied to a polyethyleneimine-cellulose TLC plate, which was developed with 0.75 M potassium phosphate (pH 4.3). $^{32}Pi$ release is plotted as a function of input protein.

FIG. 8 shows a kinetic analysis of ATP hydrolysis by Cet1p. (FIG. 8A) Protein titration. Reaction mixtures (10 μl) containing 50 mM Tris HCl (pH 7.0), 5 mM DTT, 2 mM $MnCl_2$, 1 mM $[\gamma^{32}P]ATP$, and either Cet1p, Cet1(201-549)p, or Cet1(246-549)p were incubated for 15 min at 30° C. Pi release is plotted as a function of input protein. (FIG. 8B) Kinetics. Reaction mixtures (100 μl) containing 50 mM Tris HCl (pH 7.0), 5 mM DTT, 2 mM MnCl$_2$, 1 mM [γ$^{32}$P]ATP, and either 8, 16, or 32 nM Cet1p were incubated at 30° C. Aliquots (10 μl) were withdrawn at the times indicated and quenched immediately by the addition of 2.5 ml of 5 M formic acid. Pi release is plotted as a function of time.

FIG. 11 shows Cap methylation by N-terminal deletion mutants of Hcm1p.

FIG. 13 shows replacement of the yeast capping apparatus with mammalian capping enzymes.

FIG. 14 shows the cloning of the C. albicans cap methyltransferase gene by genetic complementation in S. cerevisiae. (FIG. 14C) The sequence of the 474-amino acid Ccm1p protein is shown. The Ccm1p residues corresponding to the 8 amino acids found by alanine scanning to be essential for Hcm1p function are denoted by dots.

FIG. 21 shows the manganese-dependent ATPase activity of CaCet1p and N-terminal deletion mutants of CaCet1p. (FIG. 21A) Polypeptide composition. Aliquots (4 μg) of the phosphocellulose preparations of recombinant CaCet1p, CaCet1(203–520)p (Δ202), and CaCet1(217-520)p (Δ216) were electrophoresed through a 12.5% polyacrylamide gel containing 0.1% SDS. Polypeptides were visualized by staining with Coomassie blue dye. The positions and sizes (in kDa) of marker proteins are indicated on the left. (FIG. 21B) ATPase activity. Reaction mixtures (10 μl) containing 50 mM Tris-HCl (pH 7.5), 5 mM DTT, 2 mM MnCl$_2$, 1 mM [γ$^{32}$ P]ATP, and CaCet1p, Δ202, or Δ216 as specified were incubated for 15 min at 30° C. The reactions were quenched by adding 2.5 μl of 5 M formic acid. An aliquot (2.5 μl) of each mixture was applied to a polyethyleneimine-cellulose TLC plate, which was developed with 0.5 M LiCl$_2$, 1 M formic acid. The release of $^{32}$Pi from [γ$^{32}$P]ATP was quantitated by scanning the TLC plate with a FUJIX BAS2000 Bio-Imaging Analyzer.

FIG. 22 shows that ATP hydrolysis by the Candida albicans RNA triphosphatase is specifically activated by manganese and cobalt.

DETAILED DESCRIPTION OF THE INVENTION

Figure 3B:
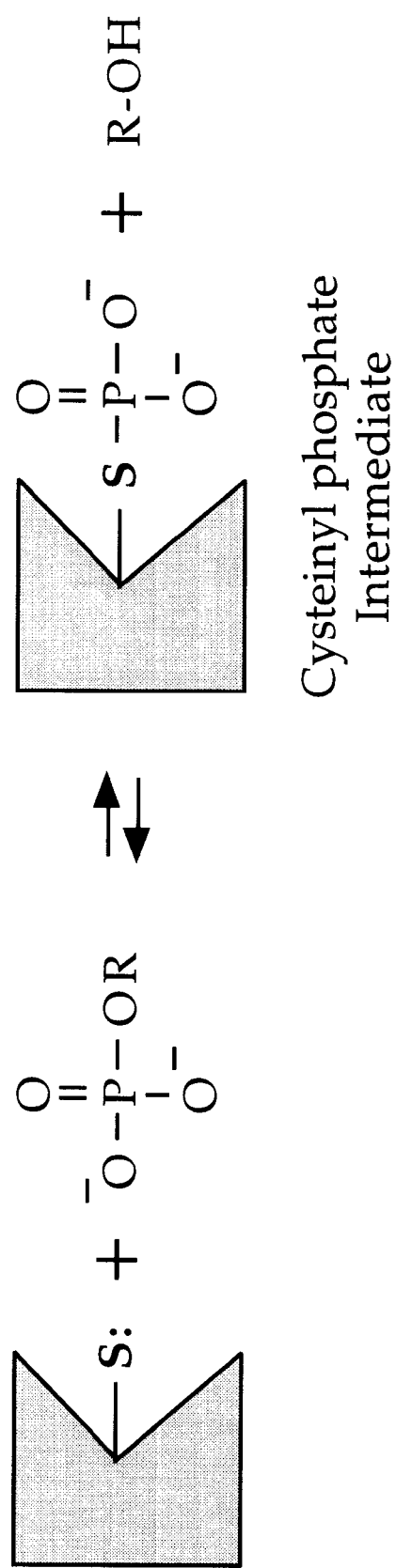
FIG. 3 shows the RNA triphosphatase domains of metazoan capping enzymes and baculovirus phosphatase BVP. The amino acid sequence of the 168-amino acid baculovirus phosphatase BVP (Baculo) is aligned with the N-terminal RNA triphosphatase domains of mouse capping enzyme (Mus CE) and *C. elegans* capping enzyme (Cel CE). Gaps in the sequences are indicated by dashes (-). Amino acids conserved in all three proteins are denoted by asterisks. The protein phosphatase signature motif is highlighted in the shaded box. The active site cysteine is in bold face (FIG. 3A). The presumptive reaction pathway involving formation of a cysteinyl phosphate intermediate is shown (FIG. 3B).

The present invention describes isogenic yeast strains containing fungal versus mammalian capping enzymes. These strains provide an attractive means of drug discovery aimed at blocking cap formation in, for example, pathogenic fungi. Any compound that is selectively cytotoxic to the "fungal capping" strain, but not to the "mammalian capping" strain, is a strong candidate for a specific inhibitor of the fungus. Secondary screens for cytotoxicity by comparing strains in which only a subset of the genes encoding the host organism's capping enzymes are replaced by a corresponding subset of genes encoding fungal or mammalian capping enzyme's can pinpoint which of the capping enzyme(s) is targeted by such a compound.

The invention described herein further elaborates on an in vivo strategy to identify antifungal compounds that block cell growth via their effects on the fungal capping apparatus. An underlying principle of this invention is the use of different strains of a test organism, such as Saccharomyces cerevisiae, that differ only in the composition or source of the essential cap-forming enzymes. The invention further provides isogenic yeast strains that derive all their capping activities from a pathogenic fungal source or a mammalian source.

The present invention describes the construction of a yeast strain in which the entire 3-component Saccharomyces cerevisiae capping apparatus is replaced by the 3-component capping apparatus of the pathogenic fungus Candida albicans. Construction of this strain was contingent upon the cloning and characterization of the Candida albicans gene encoding cap methyltransferase, which is also described herein.

This invention also provides a method to screen in vitro for molecules that inhibit fungal RNA triphosphatase, an essential enzyme that catalyzes the first of three steps in cap synthesis. This screening method exploits the intrinsic capacity of a fungal RNA triphosphatase, exemplified by the *S. cerevisiae* enzyme, Cet1p, to hydrolyze nucleoside triphosphates in the presence of a divalent cation cofactor such as manganese or cobalt. The present invention additionally includes demonstration of an intrinsic manganese- or cobalt-dependent nucleoside triphosphatase activity of the RNA triphosphatase encoded by the pathogenic fungus *Candida albicans*.

The present invention is directed to a method of screening for a compound that inhibits formation of an organism's 5' mRNA cap structure, comprising the steps of: a) replacing a host organism's genes encoding 5' mRNA capping functions with genes encoding 5' mRNA capping functions from a first organism, thereby producing a host organism expressing the first organism's capping apparatus; b) replacing a host organism's genes encoding 5' mRNA capping functions with genes encoding the 5' mRNA capping functions from a second organism, thereby producing a host organism expressing the second organism's capping apparatus, wherein said first organism and said second organism are not the same; c) treating the host organism expressing the first organism's capping apparatus and the host organism expressing the second organism's capping apparatus with a test compound; and d) comparing growth inhibition of the host organism expressing the first organism's capping apparatus with growth inhibition of the host organism expressing the second organism's capping apparatus. Growth inhibition of only the host organism expressing the first organism's capping apparatus relative to the host organism expressing the second organism's capping apparatus indicates that the test compound inhibits the 5' mRNA capping functions of the first organism, whereas growth inhibition of only the host organism expressing the second organism's capping apparatus relative to the host organism expressing the first organism's capping apparatus indicates that the test compound inhibits the 5' mRNA capping functions of the second organism. Representative host organisms are selected from the group consisting of viruses, fungal cells, insect cells, plant cells, and mammalian cells. When the host organism is a virus, comparison of growth inhibition of the virus expressing the first organism's capping apparatus with the virus expressing the second organism's capping apparatus is determined by the number of viral plaques formed on viral-permissive host cells and the viral plaque size formed on viral-permissive host cells. A preferred fungal host organism is *Saccharomyces cerevisiae*. Preferably, the first organism and second organism are selected from the group consisting of viruses, fungi, protozoa, plants, insects and mammals. Generally, the test compound will be either a chemical, a drug or protein. Preferably, the protein is encoded by DNA that can be expressed in the host organism, wherein the DNA is operably linked to an inducible promoter. Preferably, the 5' mRNA capping function inhibited by this method is RNA triphosphatase, RNA guanylyltransferase, or RNA (guanine-N7)-methyltransferase.

The present invention is directed to a method of screening for a compound that inhibits formation of an organism's 5' mRNA cap structure, comprising the steps of: a) replacing *Saccharomyces cerevisiae's* genes encoding 5' mRNA capping functions with genes encoding 5' mRNA capping functions from a first organism, thereby producing *S. cerevisiae* cells expressing the first organism's capping apparatus; b) replacing *S. cerevisiae's* genes encoding 5' mRNA capping functions with genes encoding the 5' mRNA capping functions from a second organism, thereby producing *S. cerevisiae* cells expressing the second organism's capping apparatus, wherein said first organism and said second organism are not the same; c) treating *S. cerevisiae* cells expressing the first organism's capping apparatus and *S. cerevisiae* cells expressing the second organism's capping apparatus with a test compound; and d) comparing growth inhibition of the *S. cerevisiae* cells expressing the first organism's capping apparatus with growth inhibition of the *S. cerevisiae* cells expressing the second organism's capping apparatus. Growth inhibition of only *S. cerevisiae* cells expressing the first organism's capping apparatus relative to *S. cerevisiae* cells expressing the second organism's capping apparatus indicates that the test compound inhibits the 5' mRNA capping functions of the first organism, whereas growth inhibition of only *S. cerevisiae* cells expressing the second organism's capping apparatus relative to *S. cerevisiae* cells expressing the first organism's capping apparatus indicates that the test compound inhibits the 5' mRNA capping functions of the second organism. Preferably, the first organism and second organism are selected from the group consisting of viruses, fungi, protozoa, plants, insects and mammals. Generally, the test compound will be either a chemical, a drug or protein. Preferably, the protein is encoded by a DNA expressed in the *S. cerevisiae* cells, wherein the DNA is operably linked to an inducible promoter. Preferably, the 5' mRNA capping function inhibited by this method is RNA triphosphatase, RNA guanylyltransferase, or RNA (guanine-N7)-methyltransferase.

The present invention is directed to a method of screening for a compound that inhibits formation of an organism's 5' mRNA cap structure, comprising the steps of: a) replacing *Saccharomyces cerevisiae's* genes encoding 5' mRNA capping functions with genes encoding 5' mRNA capping functions from a fungal organism, thereby producing *S. cerevisiae* cells expressing the fungal organism's capping apparatus; b) replacing *S. cerevisiae's* genes encoding 5' mRNA capping functions with genes encoding the 5' mRNA capping functions from a mammalian organism, thereby producing *S. cerevisiae* cells expressing the mammalian organism's capping apparatus; c) treating *S. cerevisiae* cells expressing the fungal organism's capping apparatus and *S. cerevisiae* cells expressing the mammalian organism's capping apparatus with a test compound; and d) comparing growth inhibition of the *S. cerevisiae* cells expressing the fungal organism's capping apparatus with growth inhibition of the *S. cerevisiae* cells expressing the mammalian organism's capping apparatus. Growth inhibition of only *S. cerevisiae* cells expressing the fungal organism's capping apparatus relative to *S. cerevisiae* cells expressing the mammalian organism's capping apparatus indicates that the test compound inhibits the 5' mRNA capping functions of the fungal organism, whereas growth inhibition of only *S. cerevisiae* cells expressing the mammalian organism's capping apparatus relative to *S. cerevisiae* cells expressing the fungal organism's capping apparatus indicates that the test compound inhibits the 5' mRNA capping functions of the mammalian organism. Generally, the test compound will be either a chemical, a drug or protein. Preferably, the protein is encoded by a DNA expressed in the *S. cerevisiae* cells, wherein the DNA is operably linked to an inducible promoter. Preferably, the 5' mRNA capping function inhibited by this method is RNA triphosphatase, RNA guanylyltransferase, or RNA (guanine-N7)-methyltransferase. A representative fungal organism from which the replacement genes are derived is *Candida albicans*.

The present invention is directed to a method of screening for a compound that inhibits the catalytic activity of fungal RNA 5' triphosphatase, comprising the steps of: a) contacting said fungal RNA 5' triphosphatase with a nucleoside triphosphate and a divalent cation cofactor in the presence and absence of a test compound; and detecting hydrolysis of said nucleoside triphosphate. A lack of hydrolysis of said nucleoside triphosphate or a reduction in the hydrolysis of said nucleoside triphosphate indicates inhibition of said fungal RNA 5' triphosphatase by said test compound. Preferably, the divalent cation cofactor is selected from the group consisting of manganese and cobalt. Although detection of hydrolysis may be by any method readily known to those having ordinary skill in this art, preferable methods include radioisotope assay and a colorimetric assay. Representative fungal RNA triphosphatases are RNA triphosphatases from Saccharomyces cerevisiae and Candida albicans.

The present invention is also directed to a transformed host organism, wherein said host organism's genes encoding 5' mRNA capping functions are replaced with replacement genes encoding 5' mRNA capping functions. Representative host organisms which can be transformed as described below include viruses, fungal cells, insect cells, plant cells, and mammalian cells. Preferably, replacement genes are from an organism selected from the group consisting of viruses, fungi, protozoa, plants, insects and mammals. A preferred host organism is Saccharomyces cerevisiae, and a preferred strain of Saccharomyces cerevisiae is YBS52 (Δcet1 Δceg1 Δabd1). Even more preferably, the replacement genes are from an organism selected from the group consisting of a fungus and a mammal, wherein replacement genes from the fungus are ABD1, CET1 and CEG1, and the resultant genotype is MATa leu2 ade2 trp1 his3 ura3 can1 ceg1::hisG cet1::LEU2 abd1::KAN p360-CET1/CEG1/ABD1, or wherein the replacement genes from said mammal are HCM1 and MCE1. A preferable organism from which the replacement genes are derived is Candida albicans; those replacement genes comprise CaCET1, CGT1 and CCM1. For example, the ABD1 gene from S. cerevisiae may be replaced with the CCM1 gene from Candida albicans, or the CET1 and CEG1 genes from S. cerevisiae may be replaced with the CaCET1 and CGT1 genes from Candida albicans.

The present invention is also directed to a transformed host S. cerevisiae, wherein said host organism's ABD1 gene is replaced with the Candida albicans CCM1 gene. The present invention is also directed to a transformed host S. cerevisiae, wherein said host organism's CET1 and CEG1 genes are replaced the Candida albicans CaCET1 and CGT1 genes.

Also provided in the present invention is an isolated CCM1 gene encoding an mRNA cap methylating enzyme AdoMet:RNA(guanine-N7)-methyltransferase from Candida albicans.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host organism" is meant to include not only prokaryotes but also eukaryotes such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells, insect cells, and plant cells, such as *Arabidopsis thaliana* and *Tobaccum nicotiana*.

The following examples are given for the purpose of illustrating various embodiments of the invention and are not meant to limit the present invention in any fashion:

EXAMPLE 1
Expression and purification of yeast RNA triphosphatase

Induced expression of the His-tagged Cet1p, Cet1(201-549)p, and Cet1(246-549)p in *Escherichia coli* BL21(DE3) cells was performed as described by Ho et al. [11]. The recombinant proteins were purified from soluble bacterial lysate by Ni-agarose and phosphocellulose column chromatography [11].

EXAMPLE 2
Mutational analysis of yeast RNA triphosphatase

Alanine substitution mutations were introduced into the CET1(201-549) gene by PCR using the two-stage overlap extension method. Residues targeted for amino acid substitutions were Glu-305, Glu-307, Arg-454, Glu-492, Glu-494, and Glu-496. Plasmid p358-CES5(201-549) was the template for the first stage amplifications. The DNA products of the second stage amplification were digested with NdeI and BamH1 and inserted into pET-16b. The presence of the desired mutations was confirmed by DNA sequencing; the inserted restriction fragment was sequenced completely in order to exclude acquisition of unwanted mutations during amplification and cloning. The His-tagged mutant proteins and the wild type protein were purified from soluble bacterial lysates by Ni-agarose chromatography as described by Ho et al. [11]. The 0.2 M imidazole eluate fractions containing Cet1(201-549)p were dialyzed against buffer C (50 mM Tris HCl [pH 8.0], 50 mM NaCl, 2 mM DTT, 10% glycerol, 0.05% Triton X-100). Protein concentration was determined by using the Bio-Rad dye reagent with bovine serum albumin as the standard.

EXAMPLE 3
HCM1 expression vectors

A DNA fragment containing the 476-amino acid HCM1 open reading frame was amplified by polymerase chain reaction from the pHG0376 template (Genbank AB007858) using Pfu DNA polymerase and oligonucleotide primers designed to introduce an NdeI restriction site at the translation start codon and a BamHI site 3' of the stop codon. The PCR product was digested with NdeI and BamHI and inserted into the T7 RNA polymerase-based expression plasmid pET16b to generate plasmid pET-His-Hcm1. N-terminal deletion mutants of HCM1 were constructed by PCR amplification with mutagenic sense-strand primers that introduced an NdeI restriction site and a methionine codon in lieu of the codons for Gly-120 and Ala-151 or an NdeI restriction site at the Met-179 codon. The PCR products were digested with NdeI and BamHI, then inserted into pET16b to yield plasmids pET-His-Hcm1(121-476), pET-His-Hcm1(152-476), and pET-His-Hcm1(179-476). The inserts of each plasmid were sequenced to verify that no unwanted coding changes were introduced during amplification and cloning.

EXAMPLE 4
Hcm1p expression and purification pET-His-Hcm1 was transformed into *Escherichia coli* BL21(DE3). A 1-liter culture of *E. coli* BL21(DE3)/pET-His-Hcm1 was grown at 37° C. in Luria-Bertani medium containing 0.1 mg/ml ampicillin until the $A_{600}$ reached 0.5. The culture was adjusted to 0.4 mM isopropyl-β-D-thiogalactopyranoside (IPTG) and incubation was continued at 30° C. for 4 h. Cells were harvested by centrifugation and the pellet was stored at −80° C. All subsequent procedures were performed at 4° C. Thawed bacteria were resuspended in 50 ml of lysis buffer (50 mM Tris HCl [pH 7.5], 0.15 M NaCl, 10% sucrose). Cell lysis was achieved by addition of lysozyme and Triton X-100 was to a final concentrations of 50 μg/ml and 0.1%, respectively. The lysate was sonicated to reduce viscosity and insoluble material was removed by centrifugation. The soluble extract was mixed for 1 h with 2-ml of Ni-NTA-agarose resin that had been equilibrated with lysis buffer. The suspension was poured into a column and washed with lysis buffer. The column was eluted stepwise with IMAC buffer (20 mM Tris HCl [pH 7.9], 0.5 M NaCl, 1 mM phenylmethylsulfonyl fluoride, 10% glycerol) containing 25, 50, 200, and 500 mM imidazole. The polypeptide composition of the column fractions was monitored by sodium dodecyl sulfate polyacrylamide gel electrophoresis (SDS-PAGE). The recombinant Hcm1p protein was retained on the column and recovered in the 200 mM imidazole eluate. An aliquot of this fraction (100 μg of protein) was applied to a 4.8-ml 15–30% glycerol gradients containing 0.5 M NaCl in buffer A (50 mM Tris-HCl [pH 8.0], 1 mM EDTA, 2 mM DTT, and 0.1% Triton X-100). The gradient were centrifuged at 50,000 rpm for 15 h at 4° C. in a Beckman SW50 rotor. Fractions (~0.2 ml) were collected from the bottom of the tube. Protein concentration was determined using the BioRad dye reagent with bovine serum albumin as the standard.

EXAMPLE 5
Expression and purification of N-terminal deletion mutants of Hcm1p A modified strategy was employed to optimize the expression of the Hcm1(121-476)p and Hcm1(152-476)p proteins in soluble form in bacteria. Cultures (1-liter) of *E. coli* BL21(DE3) bearing the pET-based plasmids were grown at 37° C. until the $A_{600}$ reached 0.5. The cultures were adjusted to 2% ethanol and incubation was continued at 17° C. for 24 h. The recombinant Hcm1(121-476)p and Hcm1(152-476)p proteins were purified from soluble lysates by Ni-agarose chromatography and glycerol gradient sedimentation as described above for wild type Hcm1p. Hcm1(179–476)p was expressed in bacteria, but was recovered exclusively in the insoluble pellet fraction of the cell lysate.

EXAMPLE 6
Yeast HCM1 expression plasmids

NdeI-BamHI restriction fragments containing the wild type HCM1 gene and the N-terminal deletion mutants were excised from the respective pET16b-based plasmids and inserted into a customized yeast expression vector pYX1-His, a derivative of pYX132 (CEN TRP1) in which six consecutive histidine codons and a unique Nde1 site are inserted between the Nco1 and BamHI sites of pYX132. (pYX132 was purchased from Novagen). The single copy expression plasmids were named pYX-Hcm1, pYX-Hcm1 (121-476), pYX-Hcm1(152-476), and pYX-Hcm1(179-476). NcoI-XhoI fragments containing the wild type HCM1 gene and the N-terminal deletion mutants were excised from the respective pYX-based CEN plasmids and inserted into the yeast expression vector pYX232 (2 m TRP1). In these vectors, expression of the human methyltransferase is under the control of the yeast TPI1 promoter.

EXAMPLE 7
Expression plasmids for yeast capping enzymes

Plasmids p360-CEG1/CET1 (CEN URA3 CET1 CEG1) and p358-CET1/CEG1 (CEN TRP1 CET1 CEG1) contain the yeast RNA triphosphatase and guanylyltransferase genes under the control of their natural promoters; the CET1 and CEG1 genes are arrayed head-to-head and transcribed divergently. Plasmids p360-CET1/CEG1/ABD1 (CEN URA3 CET1 CEG1 ABD1) and p358-CET1/CEG1/ABD1 (CEN TRP1 CET1 CEG1 ABD1) were constructed by insertion of ABD1 (under the control of its natural promoter) into p360-CEG1/CET1 and p358-CET1/CEG1, respectively; the ABD1 gene was placed next to CEG1 in a tail-to-tail orientation.

EXAMPLE 8
Yeast strains

Yeast strain YBS50 (MATa leu2 ade2 trp1 his3 ura3 can1 ceg1::hisG cet1::LEU2 p360-CET1/CEG1) is deleted at the chromosomal loci encoding RNA triphosphatase and guanylyltransferase. YBS40 (MATa leu2 ade2 trp1 his3 ura3 can1 abd1::hisG p360-ABD1) is deleted at the chromosomal locus encoding cap methyltransferase YBS52 (MATa leu2 ade2 trp1 his3 ura3 can1 ceg1::hisG cet1::LEU2 abd1::KAN p360-CET1/CEG1/ABD1) is deleted at the chromosomal loci encoding all three components of the yeast capping apparatus. YBS50, YBS40, and YBS52 were derived by targeted gene disruptions in the diploid strain W303, followed by tetrad dissection and genotyping of haploid progeny. Gene disruptions were confirmed by Southern blotting.

Figure 4:
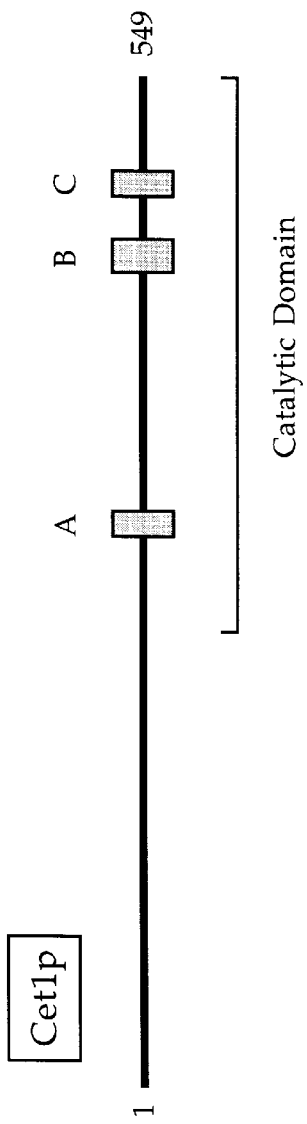
FIG. 4 shows the conserved sequence elements of the metal-dependent RNA triphosphatases. Three conserved motifs, designated A, B, and C, in the RNA triphosphatases of *S. cerevisiae* (Cet1), vaccinia virus (vvD1), Shope fibroma virus (SFV), molluscum contagiosum virus (MCV), African swine fever virus (ASF), baculovirus (Lef4), and *Candida albicans* (Cal) are aligned in the figure. Also included in the alignment is the predicted translation product of the *S. cerevisiae* YMR180c open reading frame (180c). Cet1p residues conserved in at least two other family members are shaded. The numbers of amino acids separating the motifs are indicated. The five amino acids in the vaccinia virus capping enzyme that are essential for triphosphatase activity are underlined. Cet1p residues Glu-305, Glu-307, Arg-454, Glu-492, Glu-494, and Glu-496 that are essential for CET1 function in vivo and for Cet1p RNA triphosphate activity in vitro are denoted by arrowheads. The locations of motifs A, B, and C within the yeast 456-amino acid RNA triphosphatase Cet1p is diagrammed above the aligned sequences. The margins of the C-terminal catalytic domain sufficient for g-phosphate hydrolysis are indicated by brackets.

EXAMPLE 9
RNA Triphosphatase Activity of Cet1p is Essential for Yeast Cell Growth The fungal RNA triphosphatase Cet1p is a promising drug target because it executes the first step of RNA cap formation via a reaction mechanism that is completely different from that used by the mammalian RNA triphosphatase. Before attempting to exploit the distinctions in catalytic mechanism to design approaches to antifungal drug discovery, one needs to ascertain that the RNA triphosphatase activity of Cet1p is essential for yeast cell growth. This was shown to be the case by characterizing the effects of single amino acid mutations on Cet1p function in vitro and in vivo. Mutations were targeted to conserved residues within motifs A, B, and C of the metal-dependent RNA triphosphatase/NTPase family (FIG. 4).

Cet1p residues Glu-305 and Glu-307 (motif A), Arg-454 (motif B), and Glu-492, Glu-494, and Glu-496 (motif C) were replaced individually by alanine. The Ala mutations were introduced into Cet1(201-549)p, which is fully active in vitro and in vivo [11]. The six mutated proteins were expressed as His-tagged fusions and purified from soluble lysates by Ni-agarose column chromatography in parallel with wild type Cet1(201-549)p (FIG. 6A). The RNA triphosphatase activities of the wild type and six mutant Cet1 (201–549)p proteins were assayed by the release of $^{32}Pi$ from 2 μM [γ$^{32}$P]-labeled poly(A). Specific enzyme activity was determined from the slopes of the protein titration curves in the linear range of enzyme-dependence (FIG. 6B). The specific activity of the wild type enzyme (16.5 nmol Pi released per microgram of protein in 15 min) corresponds to turnover number of ~0.8 $s^{-1}$. Analysis of RNA triphosphate cleavage by wild type Cet1(201-549)p as a function of RNA substrate concentration revealed a Km of 1 μM for poly(A) triphosphate termini and Vmax of 1 $s^{-1}$. The specific activities of the alanine mutants, calculated from the data in FIG. 6B and expressed as the percent of the wild type value, were: E305A (0.03%); E307A (0.03%); R454A (0.2%); E492A (1.7%); E494A (0.03%); E496A (0.8%).

Mutant alleles of CET1(201-549) encoding triphosphatase-defective enzymes were tested for their function in vivo using the plasmid shuffle assay described by Ho et al. [11]. The wild type and mutants coding sequences were cloned into a CEN TRP1 vector so as to place the CET1 (201-549) gene under the control of the natural CET1 promoter. The plasmids were transformed into the Δcet1 strain YBS20, in which the chromosomal CET1 locus has been deleted and replaced by LEU2. Growth of YBS20 is contingent of the maintenance of a wild type CET1 allele on a CEN URA3 plasmid. Hence, YBS20 is unable to grow on agar medium containing 0.75 mg/ml of 5-fluoroorotic acid (5-FOA), which selects against the URA3 plasmid, unless it is transformed with a biologically active CET1 allele or a functional homologue from another organism. Growth on 5-FOA was complemented by CET1 (201-549), but not by mutant alleles E305A, E307A, R454A, E492A, E494A, or E496A [12]. The correlation of in vitro and in vivo mutational effects indicates that the RNA triphosphatase activity of Cet1p is essential for yeast cell growth.

EXAMPLE 10
Manganese- and Cobalt-dependent NTPase Activity of Ceg1p

Figure 7:
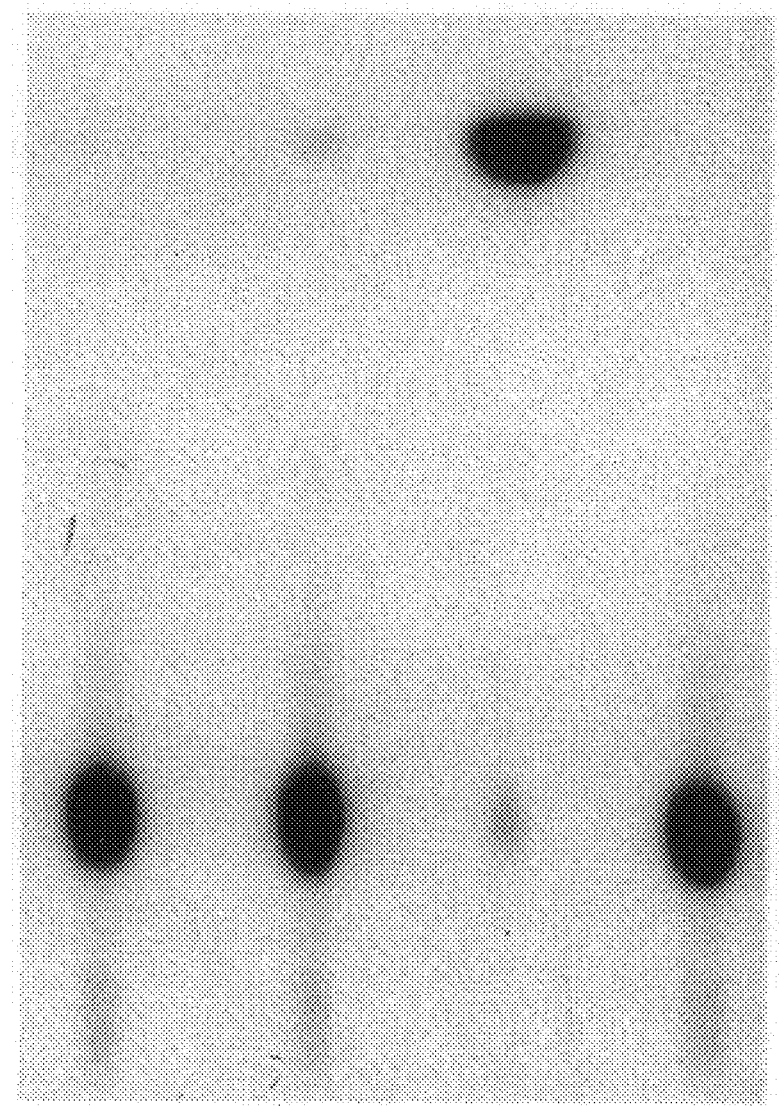
FIG. 7 shows the hydrolysis of ATP by Cet1p. Reaction mixtures (10 μl) containing 50 mM Tris HCl (pH 7.5), 5 mM DTT, 1 mM $[\gamma^{32}P]ATP$, 250 ng of recombinant Cet1p (phosphocellulose fraction), and 1 mM divalent cation as specified were incubated for 15 min at 30° C. An aliquot (4 μl) of the mixture was applied to a polyethyleneimine-cellulose TLC plate, which was developed with 0.5 M $LiCl_2$, 1 M formic acid. An autoradiograph of the TLC plate is shown. The positions of Pi and ATP are indicated on the left.

FIG. 7 illustrates that Ceg1p also catalyzes the near-quantitative release of $^{32}$Pi from 1 mM [γ$^{32}$P]ATP in the presence of 1 mM manganese as the divalent cation cofactor. There was no detectable ATP hydrolysis in the absence of a divalent cation and 1 mM magnesium was extremely feeble in supporting catalysis. The failure of previous investigators to appreciate the NTPase activity of the capping enzyme isolated from yeast extracts or recombinant Cet1p is most likely attributable to the reliance on magnesium as the divalent cation cofactor.

Divalent cation specificity was tested in reaction mixtures containing 1 mM ATP and 2 mM divalent cation. Cobalt was at least as effective as manganese in activating the ATPase. Calcium, copper, and zinc did not activate the ATPase. Cofactor titration experiments showed that hydrolysis of 1 mM ATP was optimal at 1 to 3 mM MnCl$_2$. Cobalt-dependent hydrolysis of 1 mM ATP was optimal at 1 to 5 mM CoCl$_2$. ATP hydrolysis was measured in 50 mM Tris buffer from pH 6.0 to pH 9.5. Activity was optimal from pH 6.5 to pH 7.0 and declined with increased alkalinity. Activity at pH 9.5 was 25% that at pH 7.0.

EXAMPLE 11
Kinetics of ATP Hydrolysis by Cet1p

Figure 8D:
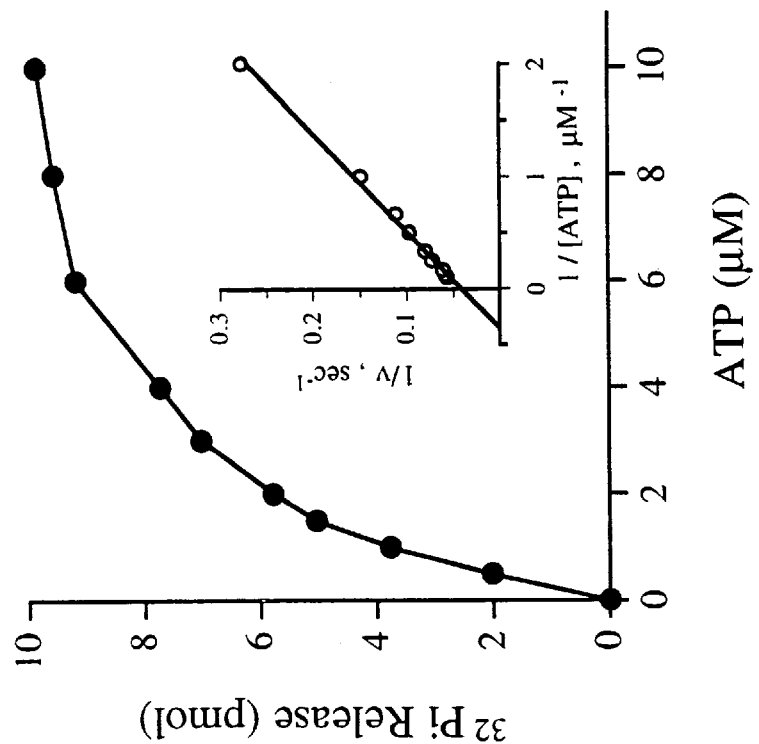
(FIG. 8D) ATP-dependence. Reaction mixtures (20 μl) containing 50 mM Tris HCl (pH 7.0), 5 mM DTT, 2 mM MnC$_2$, 40 pg of Cet1p, and [γ$^{32}$P]ATP as indicated were incubated for 15 min at 30° C. Pi release is plotted as a function of ATP concentration. Inset: a double-reciprocal plot of the data is shown.
Figure 8C:
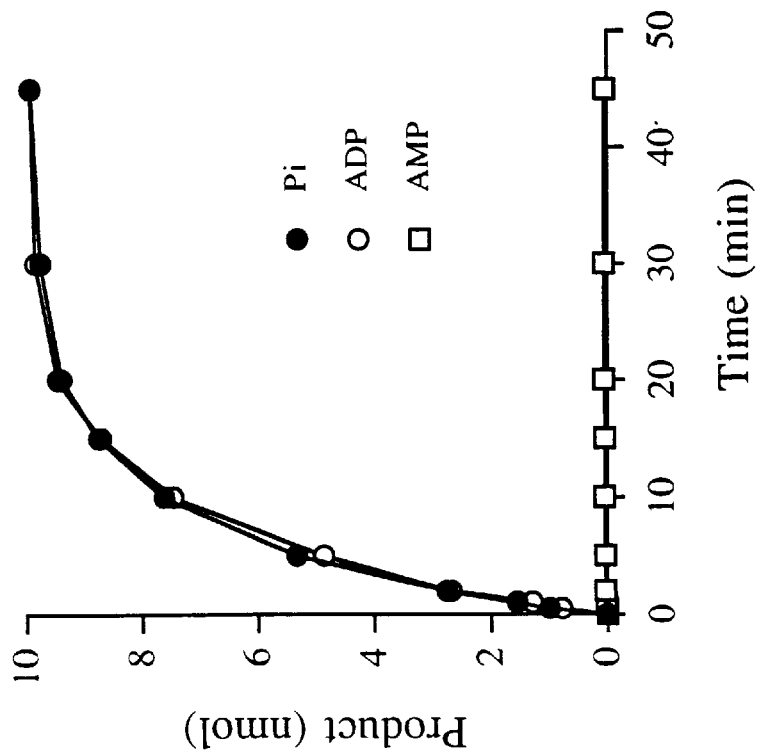
(FIG. 8C) Hydrolysis of [α$^{32}$P]ATP. Reaction mixtures (100 μl) containing 50 mM Tris HCl (pH 7.0), 5 mM DTT, 2 mM MnCl$_2$, 1 mM [α$^{32}$P]ATP, and 100 ng of Cet1p were incubated at 30° C. Aliquots (10 μl) were withdrawn at the times indicated and quenched with formic acid. The products were analyzed by TLC. The levels of [α$^{32}$P]ADP (o) and [α$^{32}$P]AMP (q) are plotted as a function of time. An otherwise identical reaction containing 1 mM [γ$^{32}$P]ATP was analyzed in parallel; Pi release (•).

The extent of $^{32}$Pi release from [γ$^{32}$P]ATP during a 15 min reaction was proportional to the amount of input Cet1p protein (FIG. 8A). $^{32}$Pi accumulated with time over 30 min; the rate of reaction varied linearly with Cet1p concentration (FIG. 8B). From a plot of initial rate versus enzyme concentration, a turnover number of 25 s$^{-1}$ was calculated. Cet1p catalyzed the quantitative conversion of [α$^{32}$P]ATP to [α$^{32}$P]ADP. The rate of [α$^{32}$P]ADP formation was identical to the rate of $^{32}$Pi release from [γ$^{32}$P]ATP assayed in a parallel reaction mixture (FIG. 8C). No formation of [α$^{32}$P] AMP from [α$^{32}$P]ATP was detected, even after 20–45 min of incubation, by which time all of the nucleotide had been converted to ADP. Thus, Cet1p catalyzes the hydrolysis of ATP to ADP plus Pi and is unable to further hydrolyze the ADP reaction product. Kinetic parameters were determined by measuring ATPase activity as a function of input [γ$^{32}$P] ATP concentration (FIG. 8D). From a double-reciprocal plot of the data, a Km of 2.8 μM ATP was calculated and a Vmax of 25 s$^{-1}$ (FIG. 8D). The phosphohydrolase activity of Cet1p was not restricted to ATP. Cet1p also catalyzed manganese-dependent hydrolysis of [α$^{32}$P]GTP to [α$^{32}$P]GDP, [α$^{32}$P] dCTP to [α$^{32}$P]dCDP, and [α$^{32}$P]dATP to [α$^{32}$P]dADP.

The turnover number of the yeast enzyme in ATP hydrolysis (25 s$^{-1}$) is similar to the values reported for the baculovirus (30 s$^{-1}$) and vaccinia virus (10 s$^{-1}$) triphosphatases, although the affinity of the yeast enzyme for ATP (Km=2.8 μM) is significantly higher than that of either LEF-4 (Km= 43 μM) or vaccinia triphosphatase (Km=800 μM) [12].

EXAMPLE 12
ATPase Activity of Cet1(201-549) and Cet1(246-549).

Two N-terminal truncation mutants, Cet1(201-549)p and Cet1(246-549)p, that retained full activity in catalyzing the release of $^{32}$Pi from γ$^{32}$P-labeled triphosphate-terminated poly(A) were previously purified and characterized [11]. Similarly, the two truncated proteins were as active as full-length Cet1p in hydrolyzing ATP (FIG. 3A). Both reactions are catalyzed by the same catalytic site within the carboxyl-terminal domain. The kinetic parameters determined for ATP hydrolysis by Cet1(201-549)p [Km=3.3 μM ATP, Vmax=33 s$^{-1}$] were similar to those of full-length Cet1p. These data suggest that the deleted N-terminal 200-amino acid segment does not contribute to nucleotide binding or reaction chemistry. Hence, purified recombinant Cet1 (201-540)p can be used to screen in vitro for candidate inhibitors of the first step of fungal cap formation based on the effects of exogenous compounds on the ATPase activity of Cet1(201-540)p.

EXAMPLE 13
Purification and Characterization of Recombinant Human Cap Methyltransferase The 476-amino acid polypeptide encoded by human cDNA KIAA0398 (Genbank accession AB007858), named Hcm1p, displays sequence conservation throughout its length with the 426-amino acid Abd1p protein (FIGS. 5A and 5B). Abd1p contains an 11-amino acid C-terminal extension that has no counterpart in Hcm1p; the C-terminal decapeptide of Abd1p is dispensable for cap methyltransferase activity in vitro and in vivo [9]. Hcm1p also displays extensive sequence similarity to the candidate cap methyltransferase from *C. elegans* (FIG. 5A and 5B). All six enzymic functional groups that have been shown to be essential for cap methylation by Abd1p (denoted by dots above the aligned sequences in FIG. 5A and 5B) are conserved in Hcm1p [8, 9].

The Hcm1p protein was expressed in bacteria fused to short histidine-rich amino-terminal leader segment. The His-tag allowed for rapid enrichment of Hcm1p based on the affinity of the tag for immobilized nickel. The bacterial lysate was applied to Ni-agarose and adsorbed material was step-eluted with increasing concentrations of imidazole. SDS-PAGE analysis revealed a prominent 56 kDa Coomassie blue-stained species in the 200 mM imidazole eluate (see FIG. 10A). This polypeptide was not recovered when lysates of IPTG-induced BL21(DE3) carrying either the pET vector alone or pET plasmids expressing other His-tagged gene products were subjected to the same Ni-agarose chromatography procedure.

Figure 9:
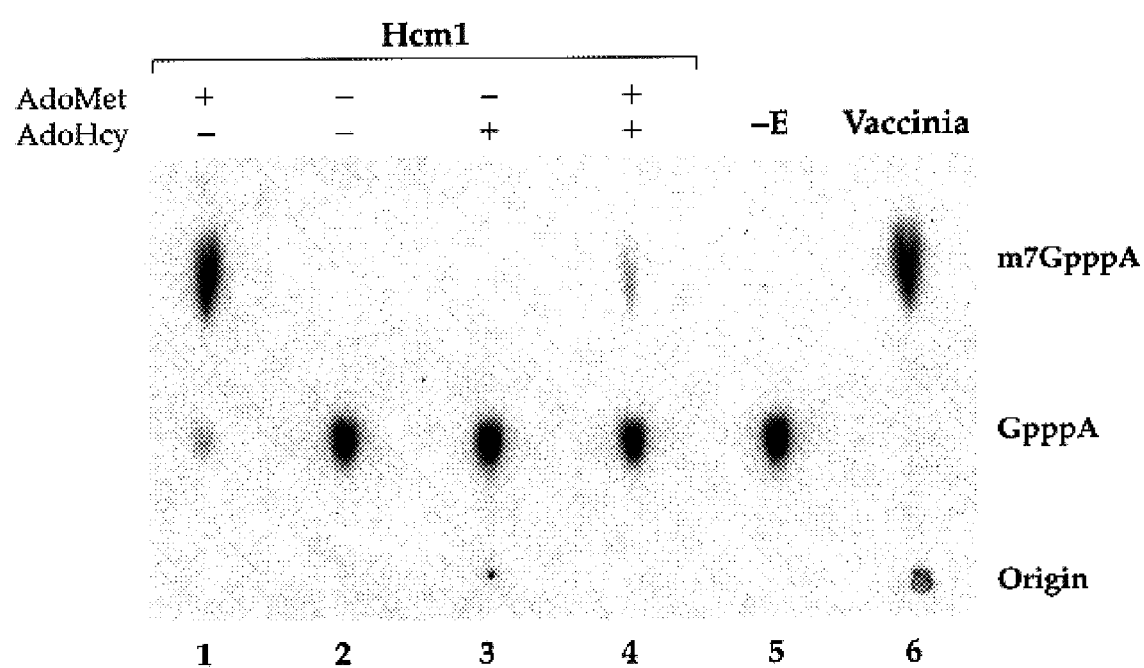
FIG. 9 shows cap methyltransferase activity of recombinant Hcm1p. The complete reaction mixture (lane 1) contained (in 10 μl) 50 mM Tris HCl (pH 7.5), 5 mM DTT, 16 fmol of cap-labeled poly(A), 50 μM AdoMet, and ~50 fmol of Hcm1p (Ni-agarose 0.2 M imidazole eluate fraction). Reaction components were varied as follows: omit AdoMet (lane 2); omit AdoMet, include 50 μM AdoHcy (lane 3); include 50 μM AdoMet plus 500 μM AdoHcy (lane 4); omit Hcm1p (lane 5); omit Hcm1p, include purified recombinant vaccinia capping enzyme (lane 6). After incubation at 37° C. for 10 min, the reaction mixtures were heated at 95° C. for 5 min, then adjusted to 50 mM sodium acetate (pH 5.5). The samples were incubated with 5 μg of nuclease P1 for 30–60 min at 37° C. The digests were then spotted on polyethyleneimine cellulose TLC plates that were developed with 0.2 M (NH$_4$)$_2$SO$_4$. An autoradiograph of the chromatogram is shown. The chromatographic origin and the positions of cap dinucleotides m7GpppA and GpppA are indicated on the right.

RNA (guanine-7-) methyltransferase activity of the Ni-agarose Hcm1p preparation was detected by the conversion of $^{32}$P cap-labeled poly(A) to methylated cap-labeled poly(A) in the presence of AdoMet [7]. The reaction products were digested to cap dinucleotides with nuclease PI and then analyzed by PEI-cellulose thin layer chromatography, which resolves the GpppA cap from the methylated cap m7GpppA. The radiolabeled product synthesized by Hcm1p (FIG. 9, lane 1) co-migrated with m7GpppA generated in a parallel reaction mixture containing purified recombinant vaccinia virus cap methyltransferase (FIG. 9, lane 6). Cap methylation by Hcm1p depended on inclusion of S-adenosylmethionine in the reaction mixture (FIG. 9, lane 2). S-adenosylhomocysteine did not support cap methylation (FIG. 9, lane 3) and was partially inhibitory in the presence of AdoMet (FIG. 9, lane 4).

Figure 10A:
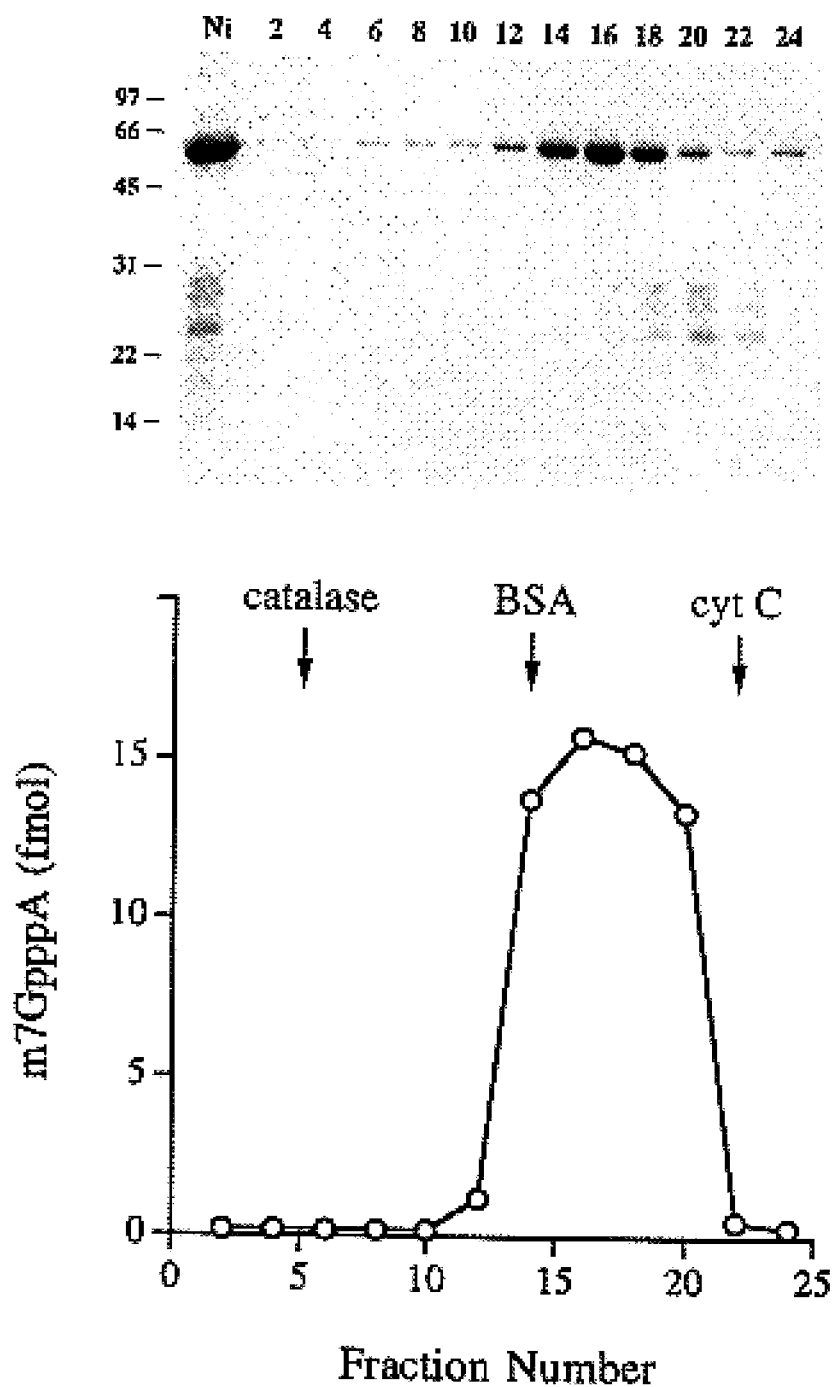
FIG. 10 shows glycerol gradient sedimentation of human cap methyltransferase. The Ni-agarose fractions of Hcm1p (FIG. 10A), and N-terminal deletion mutants Δ120 (FIG. 10B) and Δ151 (FIG. 10C) were sedimented in glycerol gradients as described under Methods. Fractions were collected from the bottom of the tubes (fraction 1). Aliquots (20 μl) of alternate fractions were analyzed by SDS-PAGE along with an aliquot of the material that had been applied to the gradient (lane Ni). The gels were fixed and stained with Coomassie blue dye. The positions and sizes (kDa) of coelectrophoresed marker polypeptides are indicated at the left of each gel. Methyltransferase reaction mixtures contained 16 fmol of cap-labeled poly(A), 50 μM AdoMet, and 1 ml of a 1/500 dilution of the indicated fractions from the Hcm1p and Δ120 glycerol gradients or 1 ml of a 1/50 dilution of fractions from the Δ151 glycerol gradient. The reaction products were digested with nuclease P1 and analyzed by TLC. The extent of cap methylation [m7GpppA/(m7GpppA+GpppA)] was determined by scanning the chromatogram using a FUJIX BAS1000 phosphorimager. The peaks of marker proteins catalase, BSA and cytochrome C, which were centrifuged in a parallel gradient, are indicated by arrowheads.

Hcm1p was further purified by centrifugation of the Ni-agarose fraction through a 15–30% glycerol gradient. Cap methyltransferase activity sedimented as a single peak coincident with the peak of the Hcm1p polypeptide (FIG. 10A). The apparent sedimentation coefficient of 4 S (relative to markers analyzed in parallel) indicated that the recombinant human cap methyltransferase is a monomer.

Characterization of the enzyme was performed using the peak glycerol gradient fraction of Hcm1p. Methylation of capped poly(A) varied linearly with input enzyme and was quantitative at saturation (FIG. 11B). Hcm1p formed 0.24 fmol of methylated capped ends per fmol of protein during a 10 min reaction. MgCl$_2$ strongly inhibited activity in a concentration-dependent fashion; methylation was reduced by an order of magnitude by 1 mM magnesium. The extent of methylation varied with AdoMet concentration. Half-maximal activity was observed at ~25 $\mu$M AdoMet. The reaction product AdoHcy inhibited cap methylation in a concentration-dependent manner; cap methylation in the presence of 10 $\mu$M AdoMet was reduced by 80% in the presence of 100 $\mu$M AdoHcy.

EXAMPLE 14
Effects of N-terminal Deletions on Cap Methyltransferase Activity.

Figure 10B:
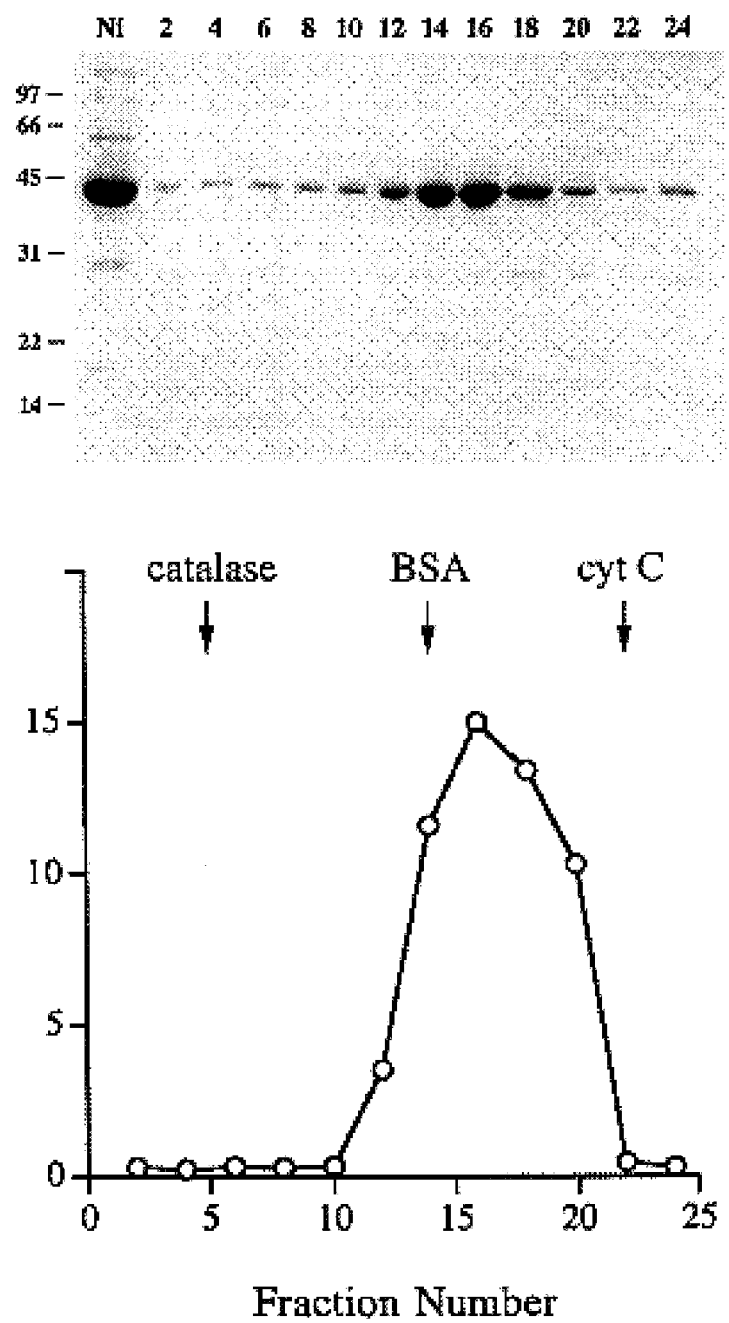
Figure 10C:
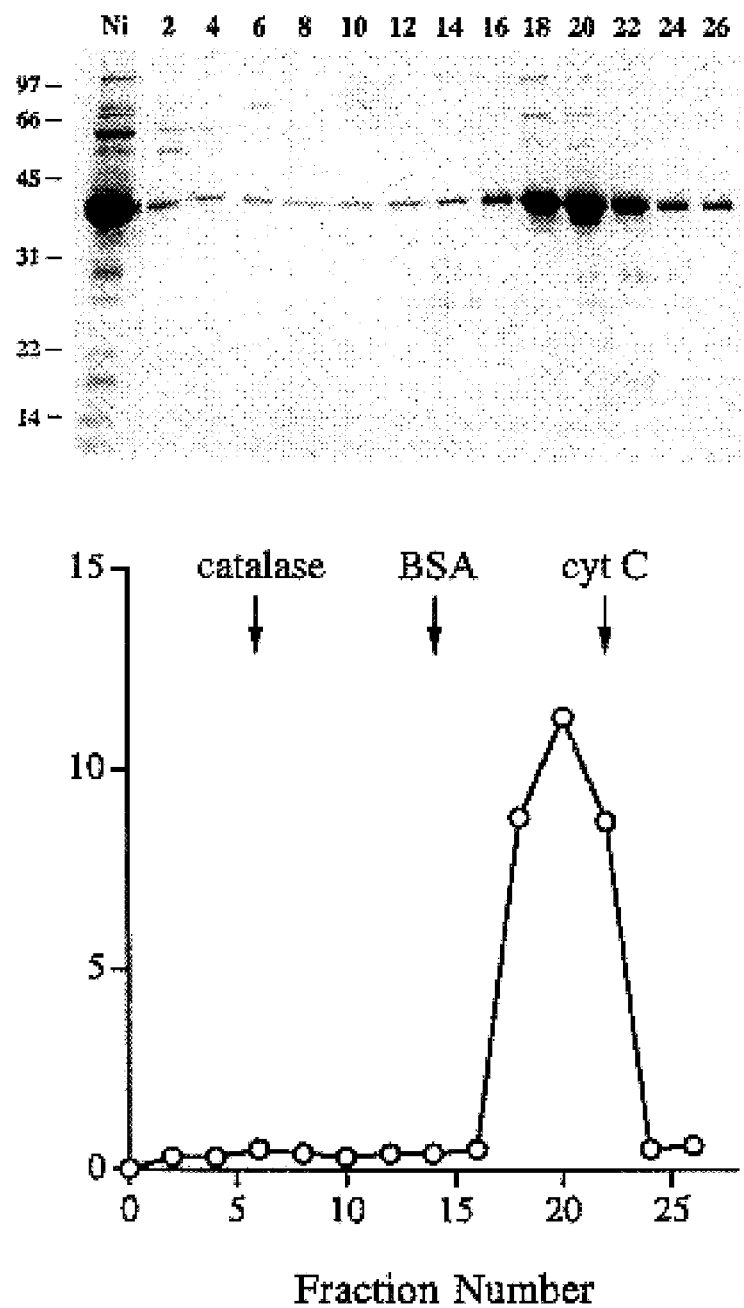

His-tagged versions of N-terminal truncated proteins Hcm1(121-476)p, Hcm1(152-476)p, and Hcm1(179-476)p were expressed in *E. coli*. Hcm1(121-476)p (referred to as Δ120) and Hcm1(152-476)p (Δ151) were purified from soluble bacterial lysates by Ni-agarose chromatography and glycerol gradient sedimentation (FIGS. 10B and 10C). Hcm1(179-476)p was insoluble and therefore not amenable to purification. The Δ120 and Δ151 proteins sedimented as discrete peaks of 4 S and 3 S respectively. Both preparations displayed cap methyltransferase activity that cosedimented with the recombinant proteins. Thus, both truncated enzymes are likely monomeric.

Figure 11A:
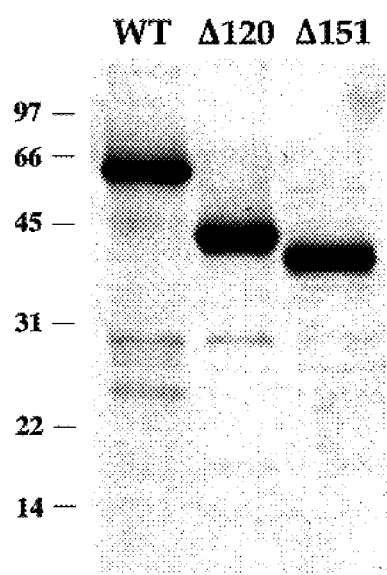
(FIG. 11A) Polypeptide composition. Aliquots (10 μg) of the peak glycerol gradient fractions of wild type Hcm1p and deletion mutants Δ120 and Δ151 were analyzed by SDS-PAGE. Polypeptides were visualized by staining with Coomassie Blue dye. The positions and sizes (kDa) of marker polypeptides are indicated at the left.
Figure 11B:
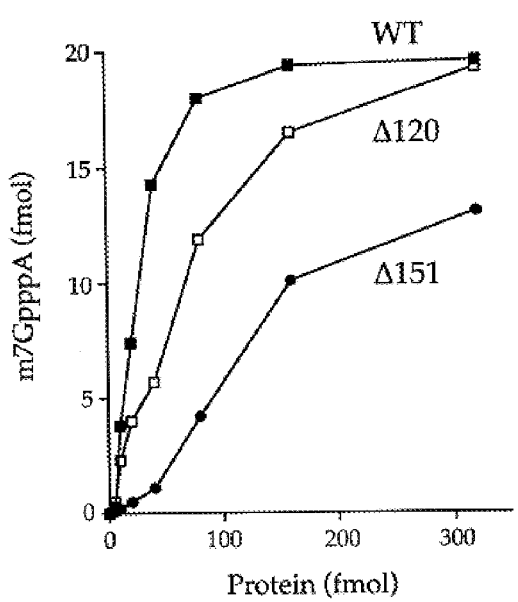
(FIG. 11B) Methyltransferase activity. Reaction mixtures contained 20 fmol of cap-labeled poly(A), 50 μM AdoMet, and WT, Δ120, or Δ151 enzyme as specified.

SDS-PAGE analysis of the peak glycerol gradient fractions of wild type Hcm1p, Δ120, and Δ151 revealed that the proteins were of comparable purity and that the truncated versions migrated more rapidly than the full-sized Hcm1p, as expected (FIG. 11A). The specific activities of Δ120 and Δ151 in cap methylation were calculated from the slopes of the titration curves in the linear range of enzyme-dependence (FIG. 11B). Δ120 retained 50% of the activity of full-length Hcm1p. Δ151 was 22% as active as the wild type enzyme.

EXAMPLE 15
Human Cap Methyltransferase is Functional In Vivo in Yeast.

Figure 12A:
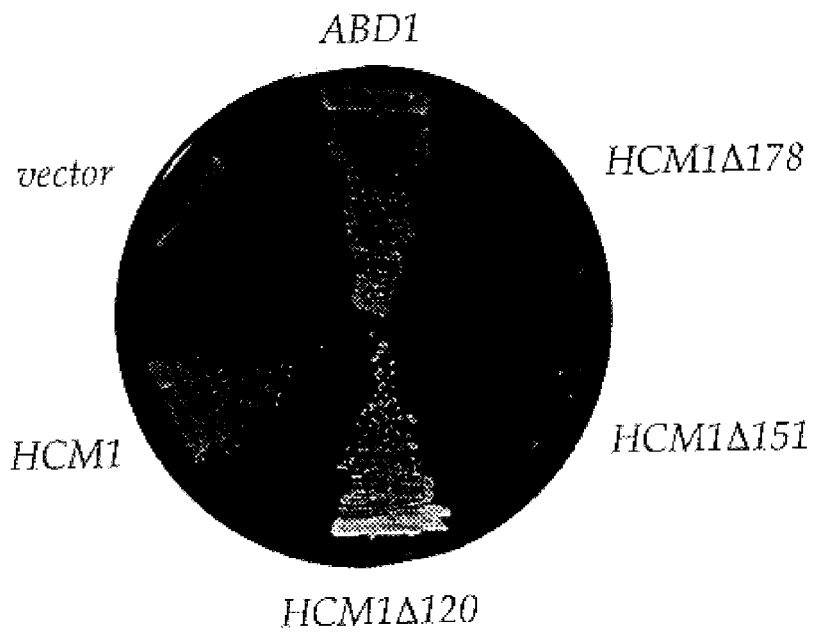
FIG. 12 shows Human cap methyltransferase substitutes for yeast Abd1p in vivo. Yeast strain YBS10 (MATa ura3 trp1 lys2 his3 leu2 abd1::hisG [pCEN URA3 ABD1])was transformed with 2 m TRP1 plasmids (FIG. 12A) or CEN TRP1 plasmids (FIG. 12B) containing the wild type HCM1 gene or N-terminal deletion mutants as specified. Control transformations were performed using the TRP1 vectors alone and a CEN TRP1 plasmid containing ABD1. Trp+ isolates were streaked on agar plates containing 0.75 mg/ml 5-FOA. The plates were photographed after incubation for 3 days at 30° C.

HCM1 and the truncated alleles HCM1(121-476), HCM1 (152-476), and HCM1(179-476) were cloned into a yeast 2$\mu$ TRP1 plasmid such that their expression was under the control of the yeast TPI1 promoter. The HCM1 plasmids were introduced into yeast strain YBS10 in which the chromosomal ABD1 locus was deleted. Growth of YBS10 is contingent on maintenance of an extrachromosomal ABD1 gene on a CEN URA3 plasmid. Trp+transformants were plated on medium containing 5-FOA to select against the URA3 ABD1 plasmid. Control cells transformed with a TRP1 ABD1 plasmid grew on 5-FOA, whereas cells transformed with the TRP1 vector were incapable of growth on 5-FOA (FIG. 12A). The instructive finding was that cells bearing the HCM1 or HCM1(121–476) plasmids grew on 5-FOA. Thus, human cap methyltransferase was functional in vivo in lieu of the endogenous yeast enzyme. The more extensively truncated alleles HCM1(152-476) and HCM1 (179–476) did not support growth on FOA (FIG. 12A).

Figure 12B:
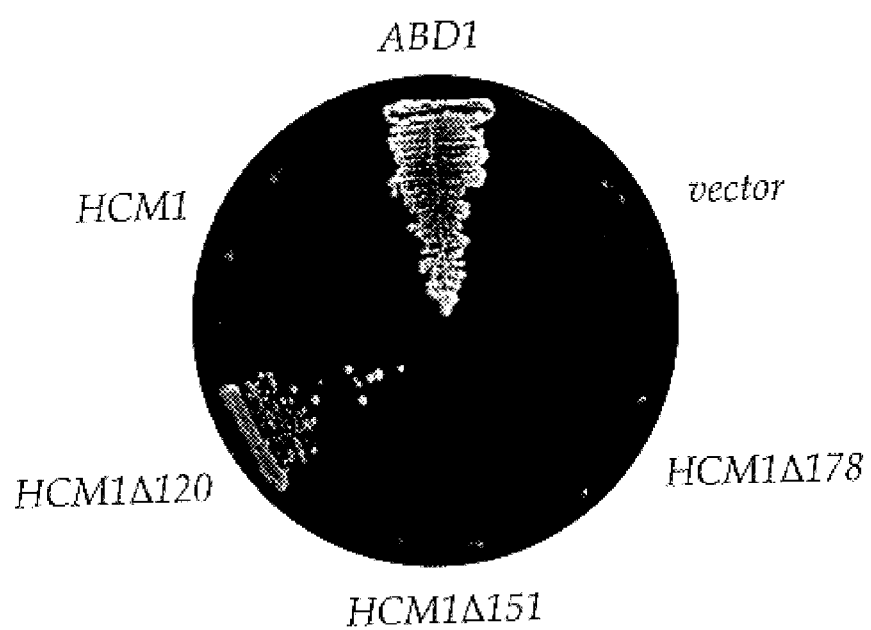

The full-length and truncated HCM1 alleles were also cloned into CEN TRP1 vectors. Expression of the Δ120 protein in single-copy complemented the abd1 deletion, whereas expression of the full-length Hcm1p protein did not (FIG. 12B). The copy-number dependence of complementation by full-length HCM1 may be indicative of lower levels of Hcm1p expression in yeast compared to the Δ120 derivative.

Based on the alignment in FIG. 5, the Δ120 deletion of Hcm1p would be roughly comparable to a deletion of 93-amino acids from the N-terminus of yeast Abd1p, whereas the Δ151 deletion would be analogous to removal of 124-amino acids from Abd1p. Deleting 52 or 109 amino acids from the N-terminus of Abd1p did not affect the ability of the deleted alleles to support yeast cell growth [8]. However, more extensive deletions of 120, 129, or 142 amino acids from the N-terminus were lethal [9]. The N-terminal margins of the minimal functional domains of the yeast and human cap methyltransferases appear to be quite similar.

EXAMPLE 16
Complete Replacement of the Yeast Capping Apparatus by Mammalian Enzymes.

The strategy for drug discovery underpinning the present invention is to identify compounds that block cell growth contingent on pathogen-encoded capping activities without affecting the growth of otherwise identical cells bearing the capping enzymes of the host organism. For this approach to be feasible, the capping systems of interest must be interchangeable in vivo. Thus, yeast strains were constructed in which the entire fungal capping apparatus was replaced by mammalian enzymes.

Figure 13A:
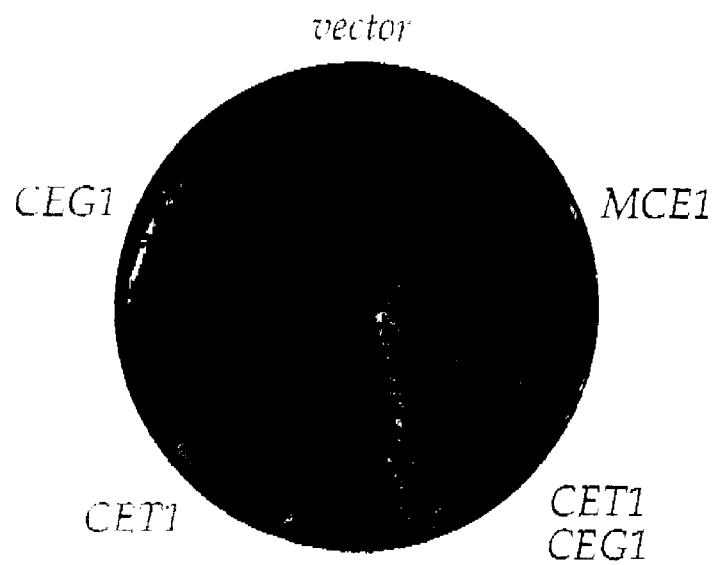
(FIG. 13A) Yeast strain YBS50 (Δcet1 Δceg1) was transformed with CEN TRP1 plasmids containing the indicated genes. Trp+isolates were streaked on agar containing 0.75 mg/ml 5-FOA. The plate was photographed after incubation for 3 days at 30° C.

Expression of the mammalian triphosphatase-guanylyltransferase in yeast can complement the growth of singly deleted Δceg1 or Δcet1 strains [11, 17, 18, 20]. The critical next step was to test the ability of the mammalian capping enzyme to complement a new Δcet1 Δceg1 double-deletion strain (YBS50), growth of which depends on maintenance of a CEN URA3 CET1 CEG1 plasmid. Control experiments showed that transformation of YBS50 with a CEN TRP1 CET1 CEG1 plasmid permitted the cells to grow on 5-FOA, whereas a CEN TRP1 plasmid containing only CET1 or only CEG1 was unable to rescue growth on 5-FOA (FIG. 10A). Expression of MCE1 on a CEN TRP1 plasmid under control of the yeast TPI1 promoter fully complemented the Δcet1 Δceg1 double-deletion (FIG. 13A).

Figure 13B:
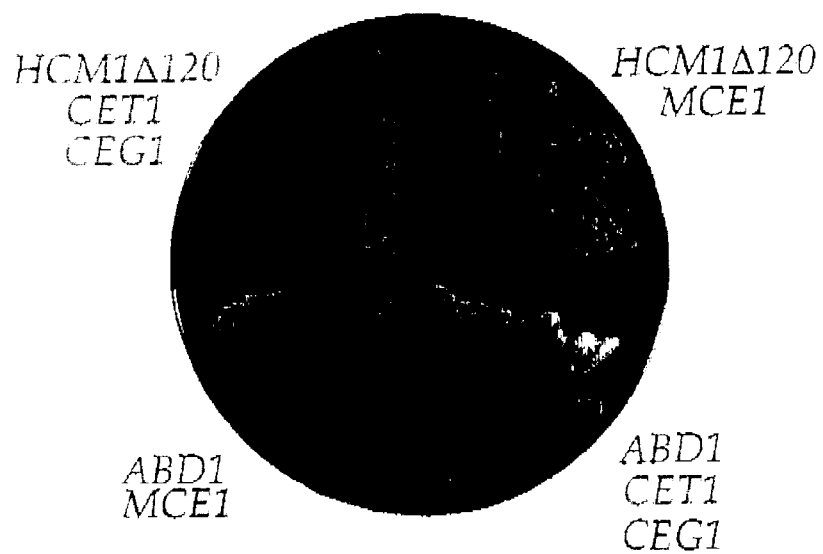
(FIG. 13B) Isogenic strains deleted at one or more yeast capping enzyme loci were transformed with CEN TRP1 plasmids as specified below and then selected on 5-FOA. FOA-resistant isolates were streaked on a YPD agar plate. The plate was photographed after incubation for 3 days at 30° C. HCM1Δ120 MCE1 is YBS52 transformed with HCM1(121-476) and MCE1; ABD1 CET1 CEG1 is YBS52 transformed with ABD1 CET1 and CEG1 on a single plasmid; ABD1 MCE1 is YBS50 transformed with MCE1; HCM1 Δ120 CET1 CEG1 is YBS40 transformed with HCM1(121-476).

A new Δcet1 Δceg1 Δabd1 triple-deletion strain (YBS52), was then constructed, growth of which is sustained by a CEN URA3 CET1 CEG1 ABD1 plasmid. Control plasmid shuffle experiments showed that YBS52 cells transformed with a CEN TRP1 CET1 CEG1 ABD1 plasmid grew on 5-FOA, whereas plasmids containing only CET1, only CEG1, or only ABD1 did not complement growth on 5-FOA. Cotransformation with MCE1 plus HCM1(121-476) complemented the triple-deletion; neither MCE1 alone nor HCM1(121-476) alone permitted growth of YBS52 on 5-FOA. FOA-resistant isolates were then streaked on YPD plates at 30° C. Using colony size as a rough estimate of growth, cells containing either MCE1 in place of CET1 plus CEG1, or HCM1(121-476) in place of ABD1 grew about as well as the strain containing an all-yeast capping apparatus (FIG. 13B). However, colony size was smaller when all three yeast genes were replaced by MCE1 plus HCM1(121-476) on CEN plasmids (FIG. 13B). Colony size was increased when the yeast genes were replaced with CEN MCE1 plus 2p HCM1(121-476), implying that the human methyltransferase was limiting for growth in single copy in this background.

To better gauge the growth of isogenic yeast cells containing yeast versus mammalian capping enzyme components, their doubling times were measured in YPD medium in suspension cultures at 30° C. The growth rates of cells containing expressing either Mce1p or Hcm1(121-476)p in lieu of the yeast enzymes (generation times 1.6 to 1.8 h) were similar to that of cells with an all-yeast capping system (1.4 h). Cells with an all-mammalian capping system expressed from single copy plasmids grew more slowly (doubling time 3.3 h), but the defect was suppressed by high-copy expression of the human methyltransferase (doubling time 2.2 h). Thus, the entire three-component fungal capping system can be replaced by the two-component mammalian system.

The two yeast strains provide the tools to implement the method of drug discovery outlined in this application. The method consists of a series of primary and secondary screening steps that are outlined below. The procedures described in the following section are applicable to the embodiment of the invention that uses yeast as the target organism in a screen for molecules that target the fungal capping apparatus. Other embodiments can be adapted as discussed above.

EXAMPLE 17
Screening for Differential Growth Inhibition Based on the Composition or Source of the Capping Apparatus.

The two yeast strains used for screening differential growth inhibition are the "fungal capping strain" (FCS) and "mammalian capping strain" (MCS), respectively. The primary screen entails plating a suspension of fungal capping strain cells on one agar plate and a suspension of mammalian capping strain cells on another plate. A matrix of test compounds is applied to the two plates in parallel, e.g., via deposition of a solution of each compound within a small hole created in the agar. The compound solution will diffuse radially from the point of application and, if growth-inhibitory, will result in a gradient of no-growth or slow-growth emanating radially from the point source. Hence, after the plates are incubated for several days at permissive growth temperature (30° C. for the fungal capping strain and mammalian capping strain yeast strains), a halo of no-growth or slow-growth will be apparent against a background lawn of yeast cells. Compounds that inhibit growth of fungal capping strain and mammalian capping strain to the same extent are presumed to be nonspecific inhibitors of yeast growth. Capping-specific inhibitors are those that inhibit growth of one of the two test strains, but not the other. For example, a compound that inhibits fungal capping strain but not mammalian capping strain is a presumed to exert its effects via the fungal capping apparatus.

Delineation of which of the three fungal capping enzymes is targeted by a candidate anti-fungal capping strain compound identified in step 1 is accomplished by a second round of screening for differential growth inhibition using strains which contain a mixture of fungal and mammalian capping components. Derivatives of the triple-knockout yeast strain YBS52 (Δcet1 Δceg1 Δabd1) have been generated that contain: (i) fungal triphosphatase and guanylyltransferase plus mammalian cap methyltransferase, (ii) mammalian triphosphatase-guanylyltransferase plus fungal cap methyltransferase. Compounds that inhibited the fungal capping strain strain by targeting the fungal triphosphatase or guanylyltransferase will inhibit strain (i), but not strain (ii). Compounds that targeted the fungal methyltransferase will inhibit strain (ii), but not strain (i).

Anti-FCS compounds found during step 2 to target the fungal triphosphatase and/or guanylyltransferase are subjected to an additional screen to gauge which of the fungal enzymes is responsible for selective growth inhibition. For this purpose, a yeast strain was constructed that contains fungal triphosphatase and mammalian guanylyltransferase.

EXAMPLE 18
In Vitro Screening for Inhibitors of Fungal RNA Triphosphatase

Cet1p displays robust nucleoside triphosphatase (NTPase) activity in the presence of manganese or cobalt as the divalent cation cofactor. The NTPase function of Cet1p is mediated by the same catalytic moieties on the enzyme that carry out the RNA triphosphatase reaction. Hence, assay of the hydrolysis of NTP by Cet1p offers a much more convenient assay than RNA triphosphatase for conducting large scale testing of Cet1p inhibitors. This is because NTPs are commercially available (including radioactively labeled NTPs), whereas the synthesis of triphosphate-terminated RNA is technically complex.

Detection of ATP hydrolysis in the experiment in FIG. 7 entailed the use of radiolabeled ATP and product analysis by thin layer chromatography. However, the assay is easily adapted to a non-radioactive colorimetric method of detection of Pi release from ATP [49]. A colorimetric assay of Cet1p activity is especially conducive to high-throughput screening of candidate inhibitors.

Figure 14A:
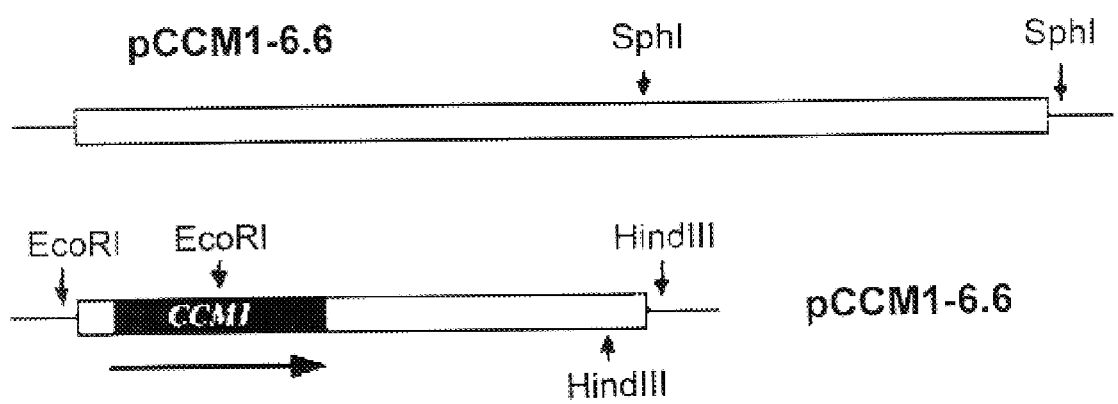
(FIG. 14A) The C. albicans genomic DNA inserts of the 2μ library plasmid pCCM1-6.6 and the subclone pCCM1-3.9 are illustrated. Restriction sites used in subcloning and gene mapping are indicated. The CCM1 open reading frame is depicted as a black bar, with the orientation of the coding strand indicated by an arrow.
Figure 14B:
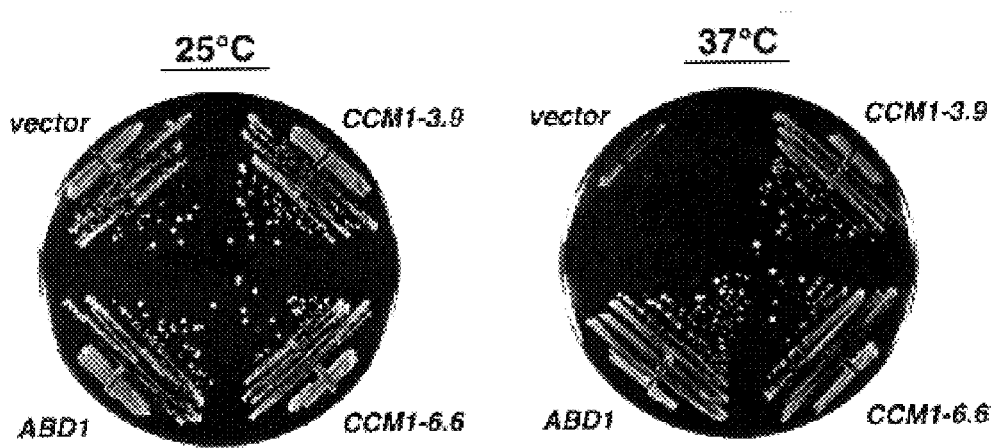
(FIG. 14B) Complementation of abd1-5 by CCM1. Yeast strain abd1-5 was transformed with 2μ URA3 plasmids pCCM1-6.6, pCCM1-3.9, YEp24 (vector), and YEp24-ABD1. Transformants were streaked on agar medium lacking uracil and incubated at either 25° C. or 37° C.

EXAMPLE 19
Isolation of the Gene Encoding Candida albicans Cap Methyltransferase by Selection for Complementation of abd1-ts Mutants The cap methyltransferase gene from the pathogenic yeast Candida albicans was identified by screening for complementation of the conditional growth defect of S. cerevisiae abd1-ts mutants after transforming three different ts mutant strains (abd1-5, abd1-8, and abd1-15) with a C. albicans genomic DNA library that had been cloned into an S. cerevisiae 2μ URA3 plasmid vector (50). Ura$^+$ transformants were selected for growth at the nonpermissive temperature of 34° C.; positive isolates were then rescreened for growth at the even higher restrictive temperature of 37° C. 2μ plasmid DNA recovered from 9 individual isolates that grew at 37° C. was amplified in E. coli and then the plasmid inserts were analyzed by digestion with a battery of restriction endonucleases that cut in the polylinker flanking the library insertion site. An apparently identical 6.6 kbp insert was present in the 2μ plasmids from all 9 isolates that had been rescued to grow at 37° C. This 2μ plasmid (named pCCM1-6.6; FIG. 14A) retested faithfully in complementation of the ts growth phenotype when retransformed into the abd1-5 strain (FIG. 14B). Hence, it was presumed that the plasmid contains the Candida cap methyltransferase gene (which was named CCM1). Excision of a 2.7 kbp SphI fragment from the right end of pCCM1-6.6 yielded the 2μ plasmid pCCM1-3.9 (FIG. 14A), which was as effective as the original isolate in rescuing growth of abd1-5 at 37° C. (FIG. 14B). Removal of a 1 kbp EcoRI fragment from the left end of the insert (to yield the 2μ plasmid pCCM1-ΔEco) resulted in loss of complementing activity, which implies that the CCM1 gene spans the EcoRI site of the insert. Removal of a 0.3 kbp HindIII fragment from the right end of the insert had no effect on complementation. Restriction fragments derived from the insert of pCCM1-3.9 were subcloned into pBluescript and then sequenced.

The CCM1 gene comprises a continuous open reading frame of 1422 nucleotides extending from left to right across the EcoRI site (FIG. 14A). CCM1 encodes a 474-amino acid polypeptide (FIG. 14C). The genomic insert in pCCM1-6.6 extends 254 bp upstream of the translation start site; this element apparently includes a C. albicans promoter element which can drive CCM1 expression in S. cerevisiae. The predicted amino acid sequence reveals Ccm1p to be a homologue of S. cerevisiae Abd1p (209 positions of identity or similarity) and the human cap methyltransferase Hcm1p (140 positions of identity or similarity). The 8 amino acid residues defined by alanine-scanning mutagenesis as essential for function of the human cap methyltransferase (22) are conserved in the C. albicans protein (FIG. 14C). Ccm1p is the first example of a cap methyltransferase from a fungal genus that is pathogenic for humans.

EXAMPLE 20
Deletion Analysis of Candida Cap Methyltransferase

Figure 15:
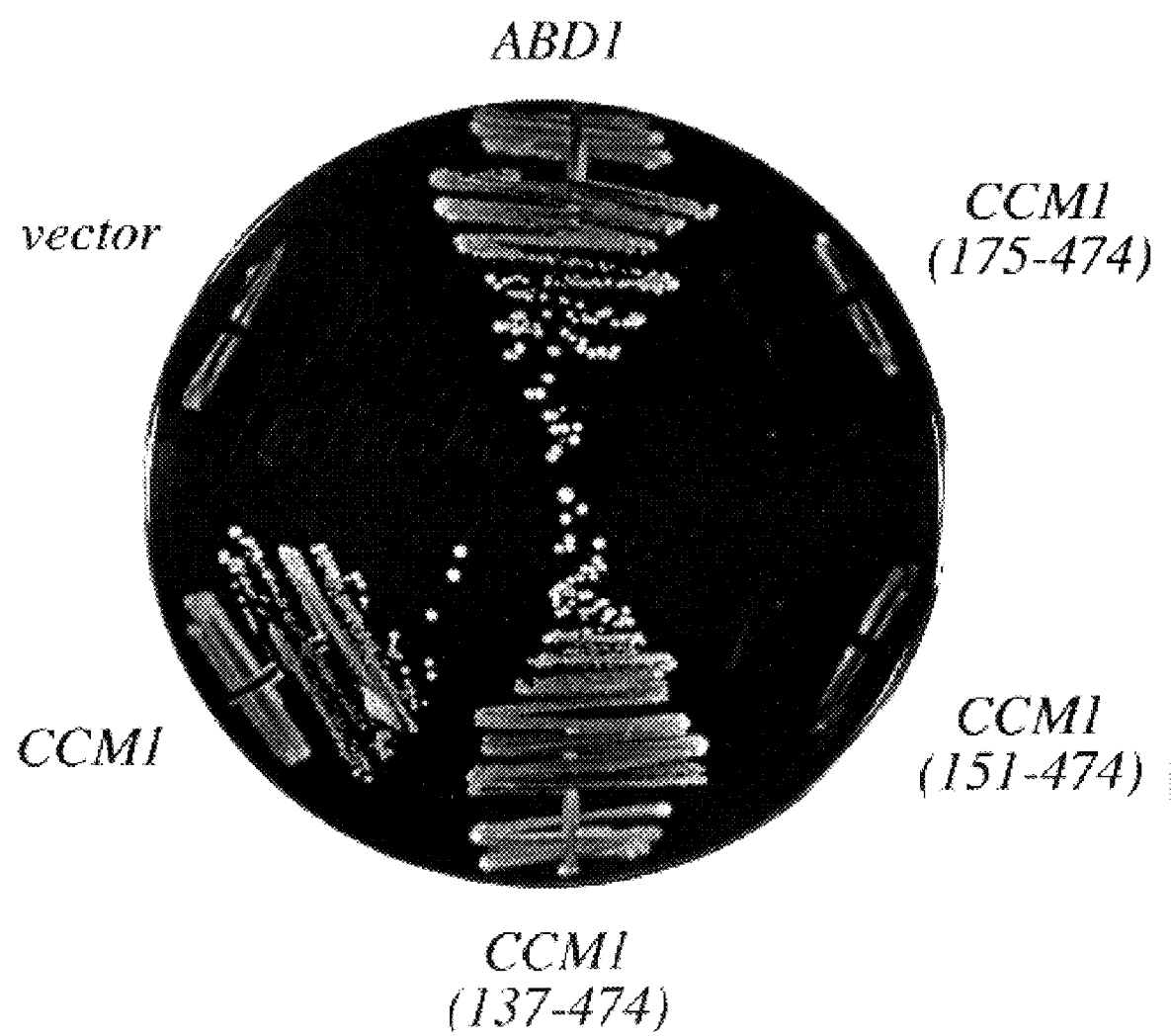
FIG. 15 shows complementation of a S. cerevisiae Δabd1 strain by the cap methyltransferase of Candida albicans and the effects of N-terminal deletions on CCM1 function in vivo. Yeast strain YBS40 was transformed with CEN TRP1 plasmids containing the indicated alleles of CCM1. Control transformations were performed using the TRP1 vector alone and p358-ABD1. Trp$^+$ isolates were streaked on an agar plate containing 0.75 mg/ml of 5-FOA. The plate was photographed after incubation for 3 days at 30° C.

The complete CCM1 coding sequence was cloned into a yeast CEN TRP1 plasmid such its expression was under the control of the constitutive S. cerevisiae TPI1 promoter. The CCM1 plasmid was introduced into a yeast strain in which the chromosomal ABD1 locus was deleted. Growth of the Δabd1 strain is contingent on maintenance of an extrachromosomal ABD1 gene on a CEN URA3 plasmid. Trp+ transformants were plated on medium containing 5-FOA to select against the URA3 ABD1 plasmid. Control cells transformed with a TRP1 ABD1 plasmid grew on 5-FOA, whereas cells transformed with the TRP1 vector were incapable of growth on 5-FOA (FIG. 15). Cells bearing the CCM1 plasmid grew on 5-FOA (FIG. 15). Thus, the C. albicans cap methyltransferase was functional in vivo in lieu of the endogenous S. cerevisiae enzyme.

Several N-terminal deletion mutants of CCM1 were cloned into the CEN TRP1 vector and tested for function in vivo by plasmid shuffle. CCM1(137-474) complemented growth of the Δabd1 strain on 5-FOA (FIG. 15). However, the more extensively truncated alleles CCM1(151-474) and PCM1(175-474) were lethal in vivo (FIG. 15). Based on an alignment of the amino acid sequences of the Ccm1p and Abd1p polypeptides, the viable N-terminal Δ136 deletion of Ccm1p would be analogous to a deletion of 108 amino acids from the N-terminus of Abd1p. The lethal N-terminal Δ150 and Δ174 deletions of Ccm1p correspond to Δ122 and Δ146 deletions of Abd1p. Prior studies showed that deleting 109 amino acids from the N-terminus of Abd1p had no effect on yeast cell growth, whereas deletion of 142 or 155 residues was lethal (51,52). Thus, the N-terminal margins of the functional domains of the Candida and Saccharomyces cap methyltransferases are fairly similar.

EXAMPLE 21
In Vivo Deletion Analysis of the Candida albicans and Saccharomyces cerevisiae RNA Triphosphatases The Candida albicans CaCET1 gene encodes a 520-amino acid RNA triphosphatase (53). The C-terminal segment of CaCet1p from residues 186 to 520 displays extensive sequence similarity to the carboxyl portion of S. cerevisiae Cet1p (a 549-amino acid polypeptide) from positions 225 to 538 (95 identical residues and 64 positions with side-chain similarity). In contrast, the N-terminal segments of CaCet1p and Cet1p are not conserved.

Figure 16:
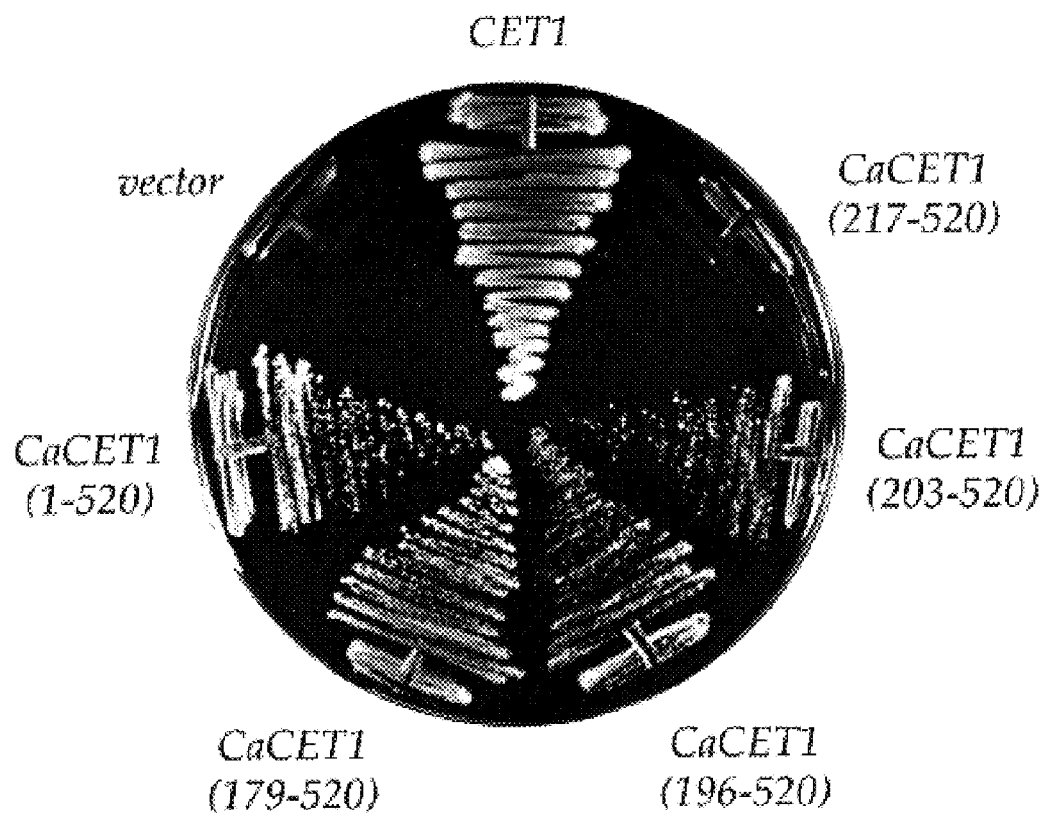
FIG. 16 shows an in vivo deletion analysis of Candida albicans RNA triphosphatase. YBS20 was transformed with CEN TRP1 plasmids containing either CET1 or the indicated alleles of CaCET1. A control transformation was performed using the TRP1 vector. Trp$^+$ isolates were streaked on agar plates containing 0.75 mg/ml of 5-FOA. The plates were photographed after incubation for 7 days at 25° C. The amino acid sequence of S. cerevisiae (Sc) Cet1p from residues 225-265 is aligned with the homologous segment of C. albicans (Ca) Cet1p. Identical amino acids are denoted by a colon (:); positions of side-chain similarity are denoted by a dot (.). The margins of the viable N-terminal deletion alleles of CET1 and CaCET1 are denoted by arrowheads above and below the aligned sequences. The N-terminus of the lethal CaCET1(217-520) mutant is marked by a small arrowhead with a cross.

To delineate the margins of the minimal functional domain of the Candida triphosphatase, the wild type CaCET1 gene and a series of N-terminal deletion alleles of CaCET1 were cloned into CEN vectors under the control of the yeast TPI1 promoter. These plasmids were transformed into a Δcet1 strain YBS20, in which the chromosomal CET1 locus has been deleted and replaced by LEU2. Growth of YBS20 is contingent on the maintenance of a wild type CET1 allele on a CEN URA3 plasmid. Hence, YBS20 is unable to grow on agar medium containing 5-fluoroorotic acid (5-FOA) unless it is transformed with a biologically active CET1 allele (FIG. 16) or a functional homologue from another organism. The instructive finding is that growth on 5-FOA was complemented by full-length CaCET1 and by deletion mutants CaCET1(179-520), CaCET1(196-520), and CaCET1(203-520), whereas CaCET1(217-520) was lethal (FIG. 16). This experiment delineates a short peptide segment between residues 203 and 216 that is required for CaCet1p function in vivo when the triphosphatase is expressed from the TPI1 promoter.

Figure 17A:
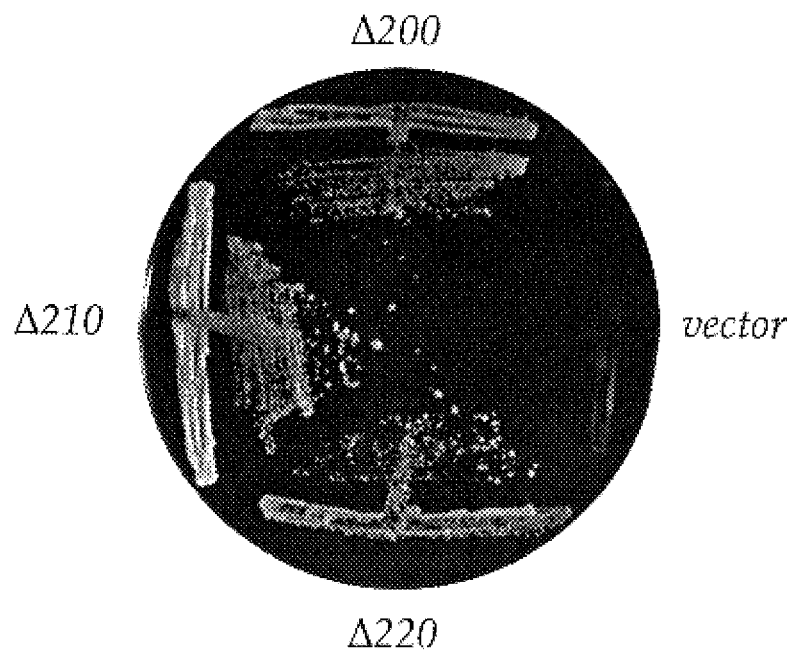
FIGS. 17A and 17B show the effect of N-terminal deletions on S. cerevisiae CET1 function in vivo. Yeast strain YBS20 was transformed with CEN TRP1 plasmids containing the indicated N-terminal deletion alleles of CET1. A control transformation was performed using the TRP1 vector. Trp+ isolates were streaked on agar plates containing 0.75 mg/ml of 5-FOA. The plates were photographed after incubation for 3 days at 30° C.
Figure 17B:
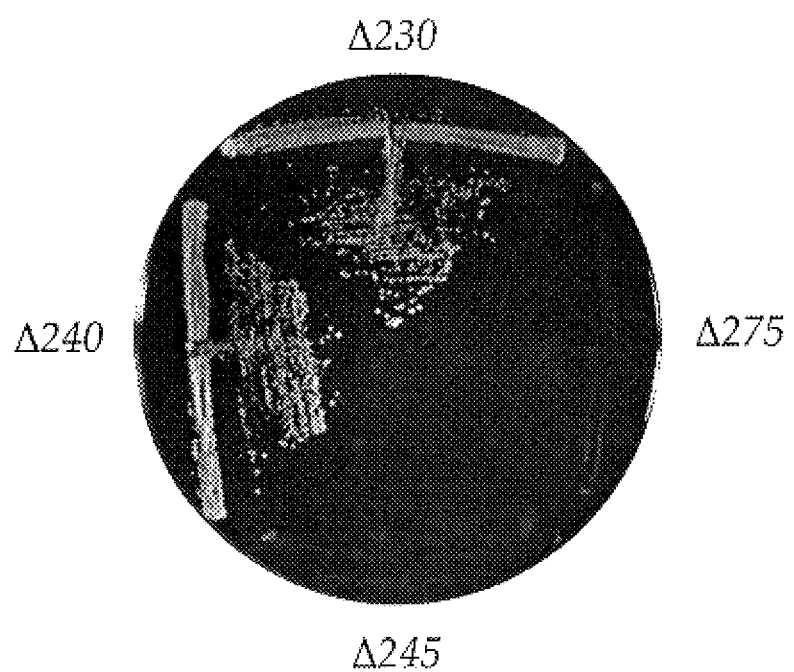

N-terminal deletion alleles of the S. cerevisiae CET1 gene—CET1(211-549), CET1(221-549), CET1(231-549), and CET1(241–549)—were cloned into a CEN TRP1 vector so as to place them under the control of the CET1 promoter. These plasmids were tested by plasmid shuffle for complementation of the Δcet1 strain YBS20. Growth on 5-FOA was complemented by CET1(201-549), CET1(211-549), CET1 (221-549), CET1(231-549), and CET1(241-549)(FIG. 17A: Δ200, Δ210, Δ220, Δ230, Δ240), but not by the more extensively truncated alleles CET1(246-549) or CET1(276-549) (FIG. 17B, Δ245 and Δ275). This experiment delineates a short peptide segment between residues 241 and 245 that is required for Cet1p function in vivo when the triphosphatase is expressed from its own promoter.

According to the sequence alignment shown in (FIGS. 17A and 17B), the viable Δ195 and Δ202 deletions of CaCet1p correspond to deletions of 235 and 242 amino acids from the N-terminus of Cet1p, whereas the lethal Δ216 mutation corresponds to a deletion of 256 residues from Cet1p. These results show that the upstream functional borders of the two fungal RNA triphosphatases are quite similar.

EXAMPLE 22
Complete Replacement of the Saccharomyces Capping Apparatus by Candida Enzymes A plausible strategy for capping-specific antifungal drug discovery is to identify compounds that inhibit the growth of yeast cells containing fungus-encoded capping activities without affecting the growth of otherwise identical yeast cells bearing the mammalian capping enzymes. Ideally, the fungal capping enzymes that sustain growth of the tester yeast cells would be those encoded by a clinically significant fungal pathogen. To achieve this scenario, S. cerevisiae strains were constructed in which the entire S. cerevisiae capping apparatus was replaced by enzymes from the pathogenic fungus Candida albicans.

Figure 18:
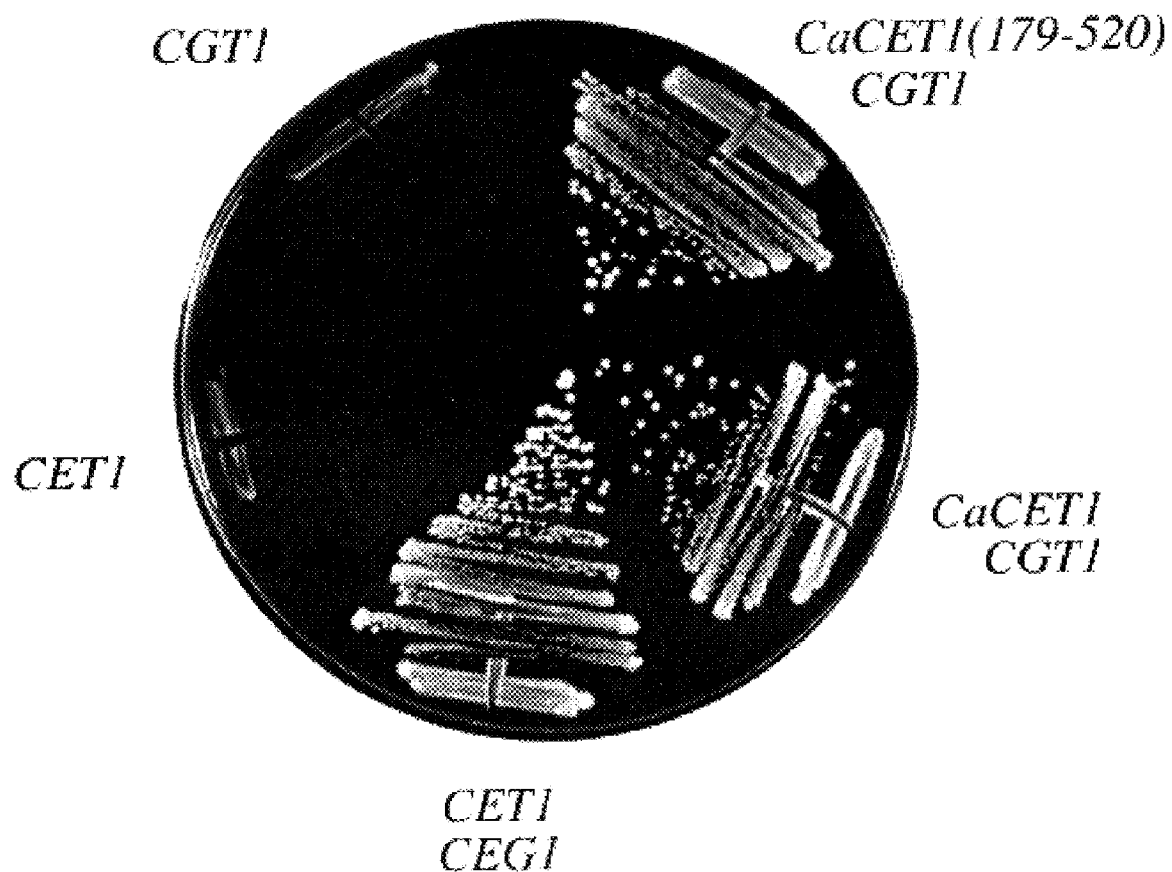
FIG. 18 shows the replacement of the triphosphatase and guanylyltransferase components of the Saccharomyces capping apparatus by Candida enzymes. Yeast strain YBS50 (Δcet1 Δceg1) was transformed with CEN TRP1 plasmids containing the indicated genes. Trp+ isolates were streaked on agar containing 0.75 mg/ml 5-FOA. The plate was photographed after incubation for 3 days at 30° C.

It has been shown that expression of Candida albicans CaCet1p (RNA triphosphatase) or Cgt1p (RNA guanylyltransferase) in S. cerevisiae can complement the growth of singly deleted Δceg1 or Δcet1 strains (53,54). FIG. 18 shows that coexpression of CaCet1p and Cgt1p in S. cerevisiae can complement a Δcet1 Δceg1 double-deletion strain (YBS50). Growth of YBS50 depends on maintenance of a CEN URA3 CET1 CEG1 plasmid. Transformation with a CEN TRP1 CET1 CEG1 plasmid permitted the cells to grow on 5-FOA, whereas a CEN TRP1 plasmid containing only CET1 or only CGT1 was unable to rescue growth on 5-FOA (FIG. 18). Transformation with a CEN TRP1 CaCET1 CGT1 plasmid complemented the Δcet1 Δceg1 strain (FIG. 18). Complementation was also evident when the cells were transformed with a plasmid containing CGT1 plus the truncated triphosphatase allele CaCET1 (179-520).

Having cloned the CCM1 gene encoding the C. albicans cap methylating enzyme, it became feasible to test whether the entire S. cerevisiae capping system could be replaced by Candida albicans enzymes. A CEN TRP1 expression plasmid (pCan-CAP-1) was constructed that contained three C. albicans genes under the control of S. cerevisiae promoters, as follows: CaCET1(179-520) controlled by the TPI1 promoter; CGT1 driven by the GPD1 promoter; CCM1 controlled by the TPI1 promoter. Another CEN TRP1 expression plasmid (pCan-CAP-2) was constructed that contained: CaCET1 (179–520) controlled by the TPI1 promoter; CGT1 driven by the GPD1 promoter; CCM1(137-474) controlled by the TPI1 promoter. pCan-CAP-1 and pCan-CAP-2 were transformed into the S. cerevisiae Δcet1 Δceg1 Δabd1 triple-deletion strain (YBS52), growth of which is sustained by a CEN URA3 CET1 CEG1 ABD1 plasmid. Plasmid shuffle experiments showed that YBS52 cells transformed with either pCan-CAP-1 and pCan-CAP-2, or with an "all-Saccharomyces" capping enzyme expression plasmid (CEN TRP1 CET1 CEG1 ABD1 ) grew on 5-FOA, whereas plasmids containing only CET1, only CEG1, or only ABD1 did not complement growth on 5-FOA.

Figure 19:
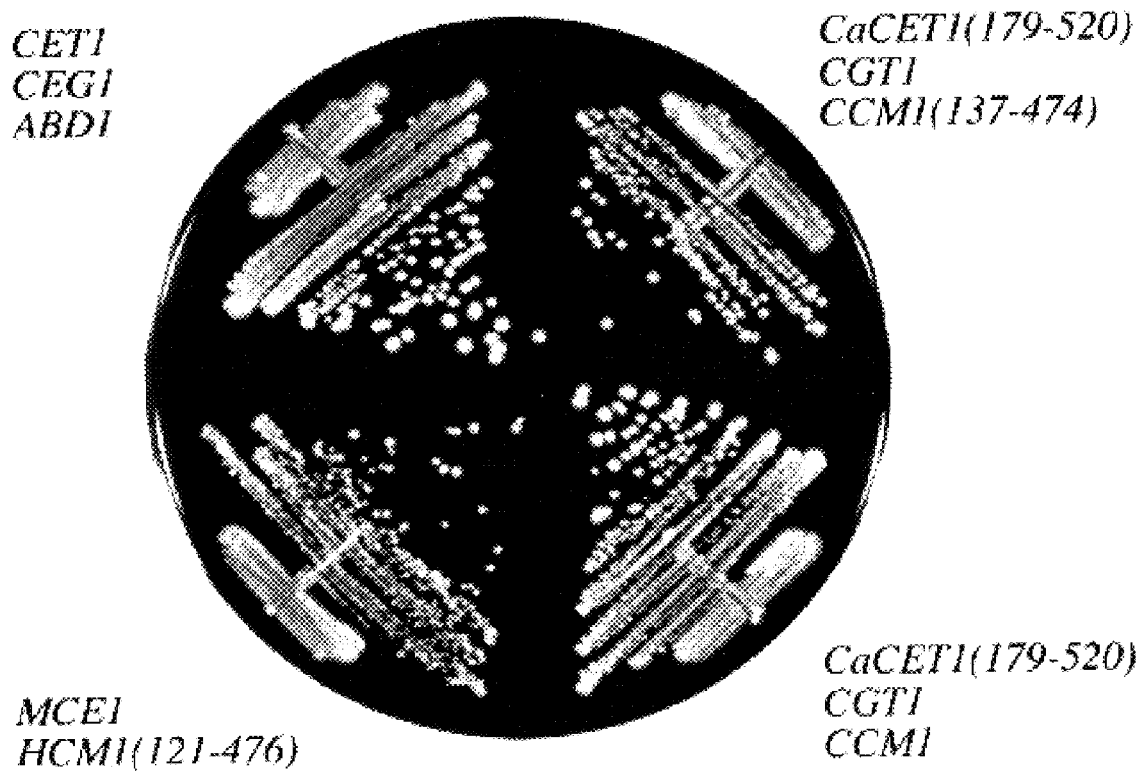
FIG. 19 shows the complete replacement of the Saccharomyces capping apparatus by Candida enzymes. Yeast strain YBS52 (Δcet1 Δceg1 Δabd1) was transformed with TRP1 plasmids as specified below and then selected on 5-FOA. FOA-resistant isolates were streaked on a YPD agar plate. The plate was photographed after incubation for 3 days at 30° C. ABD1 CET1 CEG1 was transformed with the three S. cerevisiae genes on a single CEN plasmid. CaCET1 (179-520) CGT1 CCM1(137-474) and CaCET(179-520) CGT1 CCM1 were transformed with the indicated sets of three C. albicans genes on CEN plasmids pCAN-CAP-2 and pCAN-CAP-2, respectively. MCE1 HCM1(121-476) was cotransformed with CEN MCE1 and 2μ HCM1(121 -476).

5-FOA-resistant isolates were then streaked on YPD plates at 30° C. Using colony size as a rough estimate of growth, it is surmised that cells containing either "all-Candida" capping apparatus grew as well as the cells containing an "all-Saccharomyces" capping apparatus (FIG. 19). Also shown on this plate is the growth of cells containing an "all-mammalian" capping system encoded by CEN MCE1 plus 2μ HCM1(121-476) plasmids (FIG. 19).

EXAMPLE 23

Expression and Purification of Recombinant CaCet1p

Full-length CaCet1p and the amino-terminal deletion mutants CaCet1(203-520)p (Δ202) and CaCet1(217-520)p (Δ216) were expressed in bacteria as His-tagged fusions. The CaCET1, CaCET1(203-520), and CaCET1(217-520) genes were cloned into pET-based bacterial expression vectors; the pET-CaCET plasmids were transformed into $E.$ $coli$ BL21(DE3). Cultures (100 ml) of single ampicillin-resistant transformants were grown at 37° C. in Luria Bertani medium containing 0.1 mg/ml ampicillin until the $A_{600}$ reached 0.5. The cultures were adjusted to 0.4 mM isopropyl-β-D-thiogalactopyranoside (IPTG) and incubation was continued at 37° C. for 3 h. Cells were harvested by centrifugation and the pellet was stored at −80° C. All subsequent procedures were performed at 4° C. Thawed bacteria were resuspended in 5 ml of lysis buffer (50 mM Tris HCl [pH 7.5], 0.15 M NaCl, 10% sucrose). Cell lysis was achieved by addition of lysozyme and Triton X-100 to final concentrations of 50 μg/ml and 0.1%, respectively. The lysate was sonicated to reduce viscosity and insoluble material was removed by centrifugation in a Sorvall SS34 rotor at 18,000 rpm for 45 min. The soluble lysates were applied to 1 ml columns of Ni-NTA agarose that had been equilibrated with lysis buffer. The columns were washed with 5 ml of lysis buffer containing 0.1% Triton X-100 and then eluted step-wise with a buffer solution (50 mM Tris-HCl [pH 8.0], 50 mM NaCl, 2 mM DTT, 10% glycerol, 0.05% Triton X-100) containing 50, 100, 200, 500, and 1000 mM imidazole. SDS-PAGE analysis showed that the recombinant Candida proteins were recovered predominantly in the 200 mM imidazole eluate fractions. The peak fractions containing the recombinant proteins were pooled, adjusted to 5 mM EDTA and dialyzed against P-Cell column buffer (50 mM Tris-HCl [pH 8.0], 2 mM DTT, 5 mM EDTA, 10% glycerol, 0.05% Triton X-100) containing 50 mM NaCl. The dialysates were applied to 0.5 ml columns of phosphocellulose that had been equilibrated in the same buffer. The columns were washed with buffer containing 50 mM NaCl and then eluted step-wise with P-Cell buffer containing 0.1, 0.2, 0.5, and 1.0 M NaCl. The recombinant proteins were recovered predominantly in the 0.5 M NaCl eluate fractions. Protein concentrations were determined by the Biorad dye-binding method with bovine serum albumin as the standard. The phosphocellulose enzyme preparations were stored at −80° C.

Figure 20A:
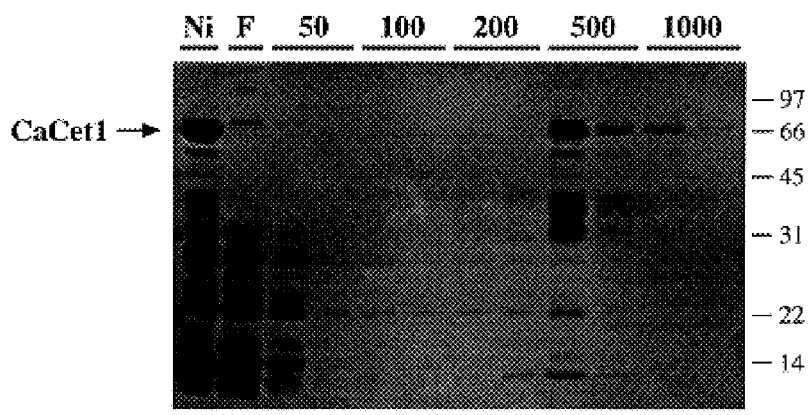
FIG. 20 shows the purification of recombinant CaCet1p, CaCet1(203-520)p (Δ202)(FIG. 20B), and CaCet1(FIG. 20A)(217-520)p (Δ216)(FIG. 20C). The phosphocellulose column elution profiles were analyzed by SDS-PAGE. Aliquots (20 μl) of the Ni-agarose fractions that were applied to the phosphocellulose columns (lanes Ni); the phosphocellulose flow-through fraction (lanes F), the phosphocellulose 50 mM NaCl wash fractions (lanes 50), the 100 mM NaCl eluate fractions (lanes 100), the 200 mM NaCl eluate fractions (lanes 200), the 500 mM NaCl eluate fractions (lanes 500) and the 1 M NaCl eluate fractions (lanes 1000) were electrophoresed through 12.5% polyacrylamide gels containing 0.1% SDS. The polypeptides were visualized by staining with Coomassie blue dye. The positions and sizes (kDa) of co-electrophoresed marker polypeptides are indicated at the right of each gel. The recombinant Candida proteins are indicated on the left.
Figure 20B:
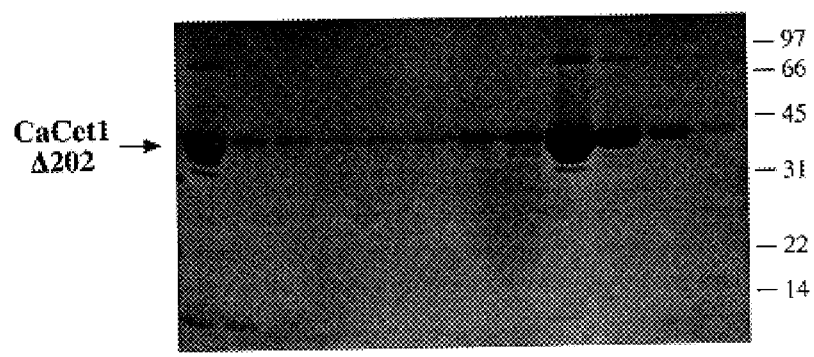
Figure 20C:
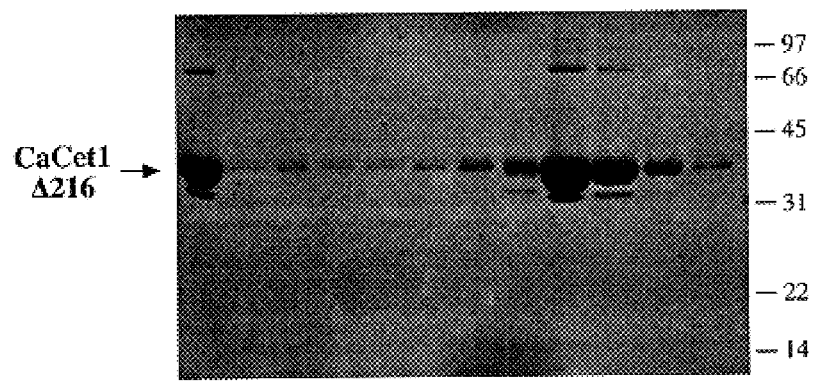

SDS-PAGE analysis of the polypeptide compositions of the Ni-agarose preparations and the phosphocellulose elution profiles are shown in (FIGS. 20A-C). The Ni-agarose eluate fraction of CaCet1p contained, in addition to the full-length 66 kDa recombinant protein, a large number of smaller polypeptides that are presumed to correspond to proteolytic fragments of CaCet1p that retain the N-terminal His-tag (FIGS. 20A-C). Similar breakdown products were also noted during Ni-agarose purification of recombinant $S.$ $cerevisiae$ Cet1p (55). The recombinant Δ202 and Δ216 polypeptides were substantially pure at the Ni-agarose step (FIG. 20A-B, lane Ni); the absence of smaller breakdown products in these preparations suggests that the N-terminal domain of CaCet1p is especially susceptible to proteolysis when expressed in bacteria.

Further purification of CaCet1p was achieved by phosphocellulose column chromatography. CaCet1p adsorbed to phosphocellulose and was step-eluted with buffer containing 0.5 M NaCl. Many of the lower molecular weight contaminant polypeptides were removed at this step (FIGS. 20A-B). The Δ202 and Δ216 proteins also adsorbed to phosphocellulose and were recovered in the 0.5 M NaCl eluate fractions (FIG. 20A-B).

EXAMPLE 24

Manganese- and Cobalt-Dependent NTPase Activity of CaCet1p

As documented in the initial patent application, $S.$ $cerevisiae$ Cet1p has an intrinsic capacity to hydrolyze nucleoside triphosphates to nucleoside diphosphates and inorganic phosphate in the presence of a divalent cation cofactor—either manganese or cobalt. The divalent cation specificity of the NTPase is distinct from the RNA triphosphatase activity of Cet1p, which is supported by magnesium. The utility of the ATPase-based assay for in vitro screening of inhibitors of fungal RNA triphosphatases is underscored by a demonstration that NTPase activity is a general property of fungal RNA triphosphatases (especially in pathogenic fungi like $C.$ $albicans$) and not merely restricted to the enzyme from $S.$ $cerevisiae.$ Experiments illustrated in FIG. 21 demonstrate that the phosphocellulose preparations of recombinant CaCet1p, Δ202, and Δ216 catalyzed the release of $^{32}Pi$ from $[\gamma^{32}P]$ ATP in the presence of manganese chloride. The extent of ATP hydrolysis increased as a function of input enzyme (FIG. 21). The specific activities of Δ202 and Δ216 were virtually identical. A turnover number of 14 $s^{-1}$ for Δ202 was calculated from the slope of the titration curve in the linear range. This value for the Candida protein is similar to the turnover number of 25 $s^{-1}$ determined for manganese-dependent ATP hydrolysis by $S.$ $cerevisiae$ Cet1p. The activity of full-length CaCet1p (on a per nanogram basis) was slightly less than that of the truncated proteins (FIG. 21); this is most probably attributable to the presence of inactive contaminating polypeptides in the preparation. Further characterization of the biochemical properties of CaCet1p was performed with the Δ202 enzyme.

Figure 22A:
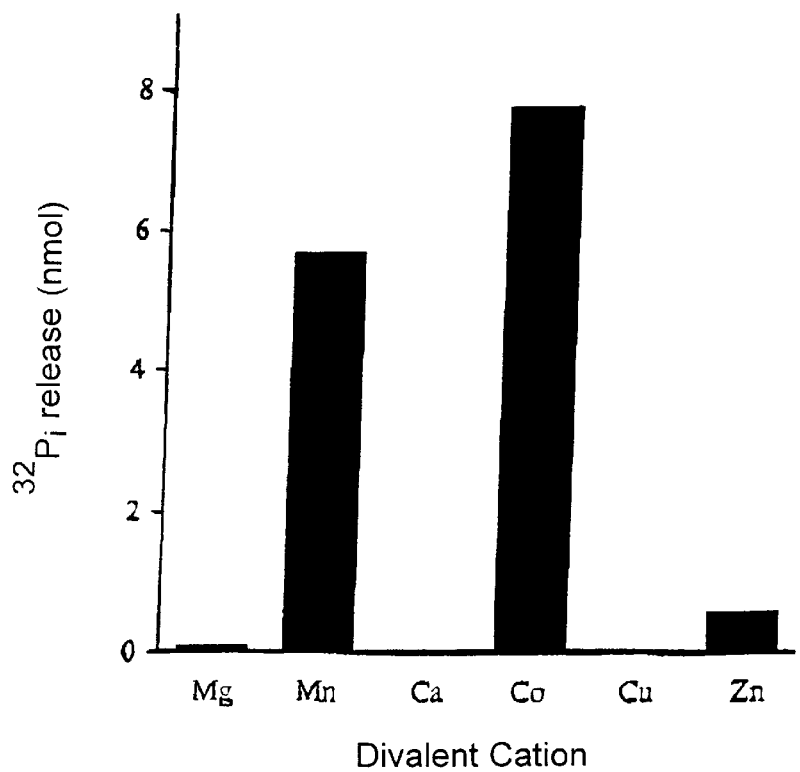
FIG. 22A: Divalent cation specificity. Reaction mixtures (10 μl) containing 50 mM Tris-HCl (pH 7.5), 1 mM [γ$^{32}$P]ATP, 50 ng of CaCet1(203-520)p (Δ202), and 2 mM divalent cation as specified were incubated for 15 min at 30° C. Mg, Mn, Ca, Co, and Zn were added as chloride salts; Cu was added as copper sulfate. The reaction products were analyzed by TLC.

The metal specificity of CaCet1Δ202 was tested in reaction mixtures containing 1 mM ATP and 2 mM divalent cation (FIG. 22A). Cobalt was even more effective than manganese in activating the ATPase, whereas magnesium did not support ATP hydrolysis. Calcium and copper did not activate the ATPase; zinc was weakly active. (The divalent cation specificity of the ATPase activity of recombinant full-length CaCet1p was the same as that shown for Cet1Δ202). The failure of previous investigators to appreciate the ATPase activity of CaCet1p (53) can be attributed to their reliance on magnesium as the divalent cation cofactor.

Figure 22B:
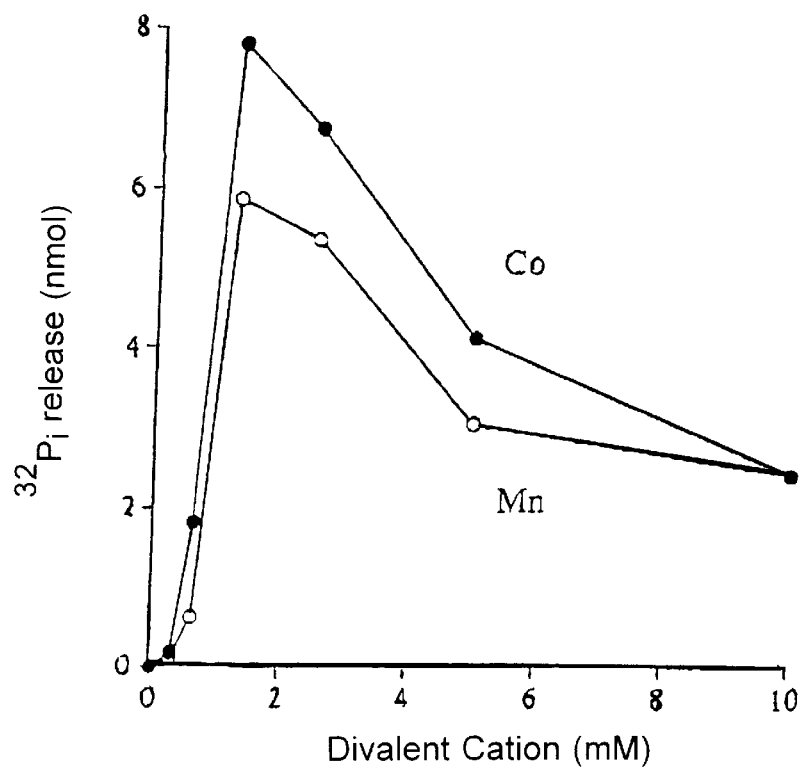
FIG. 22B: Titration of manganese and cobalt. Reaction mixtures (10 μl) containing 50 mM Tris-HCl (pH 7.5), 50 ng of Δ202, 1 mM [γ$^{32}$P]ATP, and either MnCl$_2$ or CoCl$_2$ as specified were incubated for 15 min at 30° C. Pi release is plotted as a function of manganese or cobalt concentration.

Cofactor titration experiments showed that hydrolysis of 1 mM ATP was optimal at 1 to 2.5 mM manganese or cobalt and declined slightly as the divalent cation concentrations were increased to 5 and 10 mM (FIG. 22B). The titration curves were sharply sigmoidal at manganese or cobalt concentrations below the level of input ATP.

Figure 23:
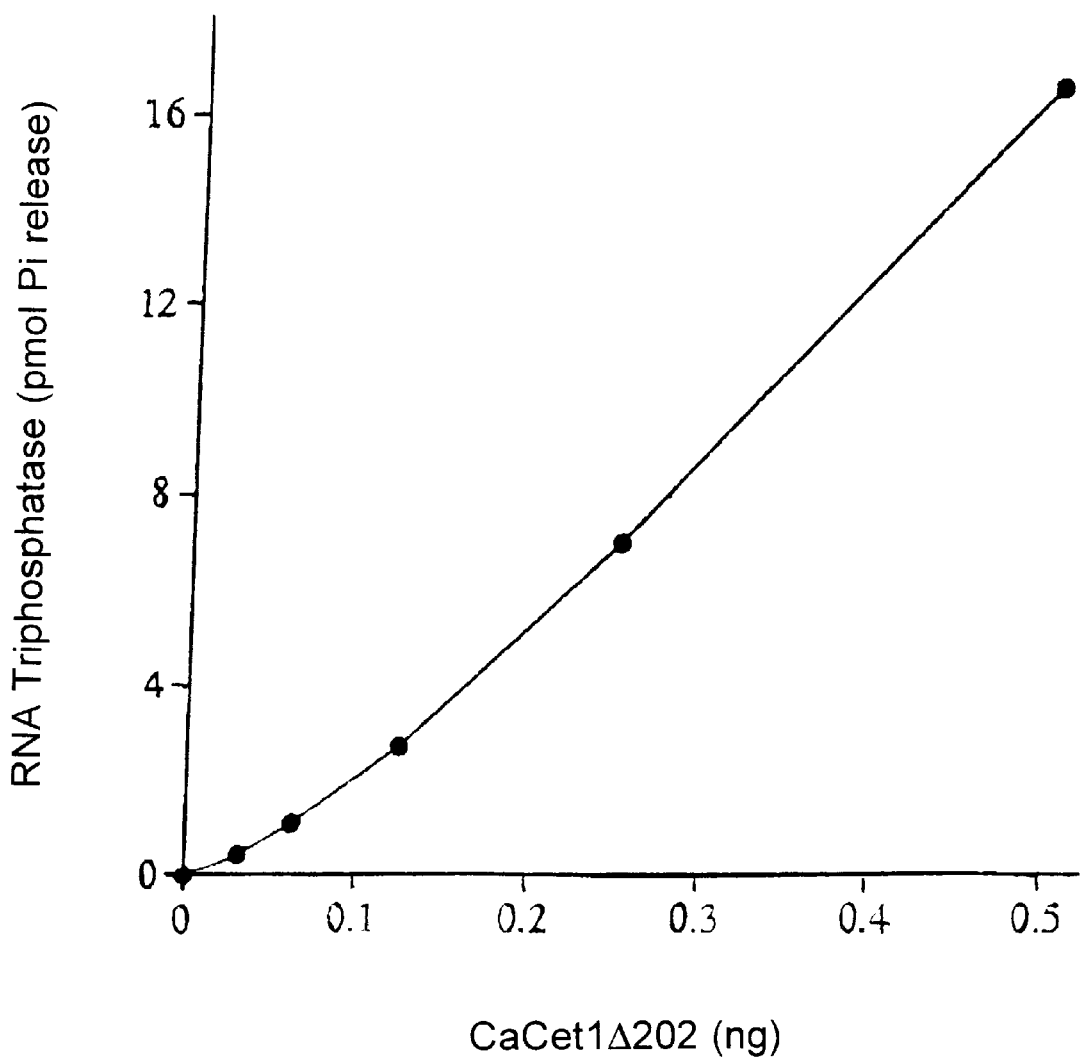
FIG. 23 shows the RNA triphosphatase activity of recombinant CaCet1(203-540)p. Reaction mixtures (10 μl) containing 50 mM Tris-HCl (pH 7.5), 5 mM DTT, 1 mM MgCl$_2$, 20 pmol (of triphosphate termini) of [γ$^{32}$P]-poly(A), and Δ202 as specified were incubated for 15 min at 30° C. Reactions were quenched by adding 2.5 μl of 5 M formic acid. Aliquots (5 μl) of the mixtures were applied to a polyethyleneimine-cellulose TLC plate, which was developed with 0.75 M potassium phosphate (pH 4.3). $^{32}$Pi release is plotted as a function of input Δ202 protein.

The RNA triphosphatase activity of CaCet1Δ202 was gauged by the release of $^{32}Pi$ from 2 μM $[\gamma^{32}P]poly(A)$ in the presence of 1 mM magnesium (FIG. 23). The specific activity, determined from the slope of the titration curve, was 32 pmol Pi released per nanogram of protein in 15 min. This corresponds to turnover number of ~1.4 s$^{-1}$ (a value that is quite close to the Vmax value of 1 s$^{-1}$ for the hydrolysis of [$\gamma^{32}$P]poly(A) by S. cerevisiae Cet1p).

The following referenes were cited herein:

1. Shuman, S. (1995) Prog. Nucleic Acid Res. Mol. Biol. 50, 101–129.
2. Schwer, et al., (1994) Proc. Natl. Acad. Sci. USA 91, 4328–4332.
3. Fresco, et al., (1994) Proc. Natl. Acad. Sci. USA 91, 6624–6628.
4. Shibagaki, et al., (1995) J. Biochem. 118, 1303–1309.
5. Shuman, et al., (1994) Proc. Natl. Acad. Sci. USA 91, 12046–12050.
6. Wang, et al., (1997) Proc. Natl. Acad. Sci. USA 94, 9573–9578.
7. Mao, et al., (1995) Mol. Cell. Biol. 15, 4167–4174.
8. Mao, et al., (1996) Mol. Cell. Biol. 16, 475–480.
9. Wang, et al., (1997) J. Biol. Chem. 272, 14683–14689.
10. Tsukamoto, et al., (1997) Biochem. Biophys. Res. Comm. 239, 116–122.
11. Ho, et al., (1998) Mol. Cell. Biol. 18, 5189–5198.
12. Ho, et al., (1998) J. Biol. Chem. (in press).
13. Schwer, et al., (1998) Nucleic Acids Res. 26, 2050–2057.
14. Sachs, et al., (1997) Cell 89, 831–838.
15. Takagi, et al., (1997) Cell 89, 867–873.
16. McCracken, et al., (1997) Genes Dev. 11, 3306–3318.
17. Yue, et al., (1997) Proc. Natl. Acad. Sci. USA 94, 12898–12903.
18. Ho, et al.,(1998) J. Biol. Chem. 273, 9577–9585.
19. Tsukamoto, et al., (1998) Biochem. Biophys. Res. Comm. 243, 101–108.
20. Yamada-Okabe, et al., (1998) Nucleic Acids Res. 26, 1700–1706.
21. Pillutla, et al., (1998) J. Biol. Chem. 273, 21443–21446.
22. Saha, et al., (1999) J. Biol. Chem. in press
24. Mao, X., & S. Shuman. (1994) J. Biol. Chem. 269, 24472–24479.
25. Higman, et al., (1994) J. Biol. Chem. 269, 14974–14981.
26. Cong. P., & Shuman, S. (1995) Mol. Cell. Biol. 15, 6222–6231.
27. Yu, L., & Shuman, S. (1996) J. Virol. 70, 6162–6168.
28. Yu, et al., (1997) J. Virol. 71, 9837–9843.
29. Myette, et al., (1996) J. Biol. Chem. 271, 11936–11944.
30. Myette, et al., (1996) J. Biol. Chem. 271, 11945–11952.
31. Gross, C. H., & Shuman, S. (1998) J. Virol. (in press).
32. Jin, et al., (1998) J. Virol. (in press).
33. Ho, et al., (1996) J. Virol. 70, 6658–6664.
34. Shuman, S., & Hurwitz, J. (1981) Proc. Natl. Acad. Sci. USA 78, 187–191.
35. Shuman, S., & Schwer, B. (1995) Mol. Microbiol. 17, 405–410.
36. Hakansson, et al., (1997) Cell 89, 545–553.
37. Wang, S. P., & Shuman, S. (unpublished).
38. Wen et al., (1998) Proc. Natl. Acad. Sci. USA 95, 12226–12231.
39. Gross, C. H., & Shuman, S. (1998) J. Virol. 72, 7057–7063.
40. Takagi, et al., (1998) Proc. Natl. Acad. Sci. USA 95, 9808–9812.
41. Bisaillon, M., & Lemay, G. (1997) Virology 236, 1–7.
42. Silva, et al., (1998) Mol. Cell. Biol. 18, 4612–4619.
43. Shuman, et al., (1980) J. Biol. Chem. 255, 11588–11598.
44. Shuman, S. (1990). J. Biol. Chem. 265, 11960–11966.
45. Yamada-Okabe, et al., (1998) FEBS Lett. 435, 49–54.
46. Mao, X., & S. Shuman (1996) Biochemistry 35, 6900–6910.
47. Cho, et al., (1997) Genes Dev. 11, 3319–3326.
48. Shuman, S. (1997) Proc. Natl. Acad. Sci. USA 94, 12758–12760.
49. Lanzetta, et al., (1979) Anal. Biochem. 100, 95–97.
50. Janbon, G., et al., (1997) Yeast 10, 985–990.
51. Mao, X., et al., (1996) Mol. Cell. Biol. 16, 475–480.
52. Wang, S. & Shuman, S. (1997) J. Biol. Chem. 272, 14683–14689.
53. Yamada-Okabe, T., et al., (1998) FEBS Lett. 435, 49–54.
54. Yamada-Okabe, T., et al., (1996) Microbiology 142, 2515–2523.
55. Ho, C. K., et al., (1998) Mol. Cell. Biol. 18, 5189–5198.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for a compound that inhibits formation of an organism's 5' mRNA cap structure, wherein the organism is fungi; comprising the steps of:
    a) replacing a host organism's genes encoding entire 5' mRNA capping functions with genes encoding 5' mRNA capping functions from a first organism, thereby producing a host organism expressing the first organism's complete capping apparatus;
    b) replacing a host organism's genes encoding entire 5' mRNA capping functions with genes encoding the 5' mRNA capping functions from a second organism, thereby producing a host organism expressing the second organism's complete capping apparatus, wherein said first organism and said second organism are not the same;
    c) treating said host organism expressing the first organism's complete capping apparatus and said host organism expressing the second organism's complete capping apparatus with a test compound; and
    d) comparing growth inhibition of the host organism expressing the first organism's complete capping apparatus with growth inhibition of the host organism expressing the second organism's complete capping apparatus, wherein growth inhibition of only the host organism expressing the first organism's complete capping apparatus relative to the host organism expressing the second organism's complete capping apparatus indicates that the test compound inhibits the 5' mRNA capping functions of the first organism, whereas growth inhibition of only the host organism expressing the second organism's complete capping apparatus relative to the host organism expressing the first organism's complete capping apparatus indicates that the test compound inhibits the 5' mRNA capping functions of the second organism.

2. The method of claim 1, wherein the host organism is selected from the group consisting of viruses, fungal cells, insect cells, plant cells, and mammalian cells.

3. The method of claim 2, wherein when said host organism is a virus, comparison of growth inhibition of the virus expressing the first organism's capping apparatus with the virus expressing the second organism's capping apparatus is selected from the group consisting of the number of viral plaques formed on viral-permissive host cells and the viral plaque size formed on viral-permissive host cells.

4. The method of claim 2, wherein said fungal cells are *Saccharomyces cerevisiae* or *Candida albicans*.

5. The method of claim 1, wherein said first organism and said second organism are selected from the group consisting of viruses, fungi, protozoa, plants, insects and mammals.

6. The method of claim 1, wherein said test compound is selected from the group consisting of chemicals, drugs and proteins.

7. The method of claim 6, wherein said protein is encoded by a DNA expressed in said host cells, wherein said DNA is operably linked to an inducible promoter.

8. The method of claim 1, wherein said 5' mRNA capping function is selected from the group consisting of RNA triphosphatase, RNA guanylyltransferase, and RNA (guanine-N7)-methyltransferase.

9. A method of screening for a compound that inhibits formation of an organism's 5' mRNA cap structure, comprising the steps of:
    a) replacing genes encoding entire 5' mRNA capping functions from *Saccharomyces cerevisiae* or *Candida albicans* with genes encoding 5' mRNA capping functions from a first organism, thereby producing *S. cerevisiae* or *Candida albicans* cells expressing the first organism's complete capping apparatus;
    b) replacing genes encoding entire 5' mRNA capping functions from *Saccharomyces cerevisiae* or *Candida albicans* with genes encoding the 5' mRNA capping functions from a second organism, thereby producing *S. cerevisiae* or *Candida albicans* cells expressing the second organism's complete capping apparatus, wherein said first organism and said second organism are not the same;
    c) treating *S. cerevisiae* or *Candida albicans* cells expressing the first organism's complete capping apparatus and *S. cerevisiae* or *Candida albicans* cells expressing the second organism's complete capping apparatus with a test compound; and
    d) comparing growth inhibition of the *S. cerevisiae* or *Candida albicans* cells expressing the first organism's complete capping apparatus with growth inhibition of the *S. cerevisiae* or *Candida albicans* cells expressing the second organism's complete capping apparatus, wherein growth inhibition of only *S. cerevisiae* or *Candida albicans* cells expressing the first organism's capping apparatus relative to *S. cerevisiae* cells or *Candida albicans* expressing the second organism's complete capping apparatus indicates that the test compound inhibits the 5' mRNA capping functions of the first organism, whereas growth inhibition of only *S. cerevisiae* or *Candida albicans* cells expressing the second organism's capping apparatus relative to *S. cerevisiae* or *Candida albicans* cells expressing the first organism's complete capping apparatus indicates that the test compound inhibits the 5' mRNA capping functions of the second organism.

10. The method of claim 9, wherein said first organism and said second organism are selected from the group consisting of viruses, fungi, protozoa, plants, insects and mammals.

11. The method of claim 9, wherein said test compound is selected from the group consisting of chemicals, drugs and proteins.

12. The method of claim 11, wherein said protein is encoded by a DNA expressed in said *S. cerevisiae* or *Candida albicans* cells, wherein said DNA is operably linked to an inducible promoter.

13. The method of claim 9, wherein said 5' mRNA capping function is selected from the group consisting of RNA triphosphatase, RNA guanylyltransferase, and RNA (guanine-N7)-methyltransferase.

14. A method of screening for a compound that inhibits formation of an organism's 5' mRNA cap structure, comprising the steps of:
   a) replacing genes encoding entire 5' mRNA capping functions from *Saccharomyces cerevisiae* or *Candida albicans* with genes encoding 5' mRNA capping functions from a fungal organism, thereby producing *S. cerevisiae* or *Candida albicans* cells expressing the fungal organism's complete capping apparatus;
   b) replacing genes encoding entire 5' mRNA capping functions from *Saccharomyces cerevisiae* or *Candida albicans* with genes encoding the 5' mRNA capping functions from a mammalian organism, thereby producing *S. cerevisiae* or *Candida albicans* cells expressing the mammalian organism's complete capping apparatus;
   c) treating *S. cerevisiae* or *Candida albicans* cells expressing the fungal organism's complete capping apparatus and *S. cerevisiae* or *Candida albicans* cells expressing the mammalian organism's complete capping apparatus with a test compound; and
   d) comparing growth inhibition of the *S. cerevisiae* or *Candida albicans* cells expressing the fungal organism's complete capping apparatus with the *S. cerevisiae* or *Candida albicans* cells expressing the mammalian organism's complete capping apparatus, wherein growth inhibition of only *S. cerevisiae* or *Candida albicans* cells expressing the fungal organism's complete capping apparatus relative to *S. cerevisiae* or *Candida albicans* cells expressing the mammalian organism's complete capping apparatus indicates that the test compound inhibits the 5' mRNA capping functions of the fungal organism, whereas growth inhibition of only *S. cerevisiae* cells or *Candida albicans* expressing the mammalian organism's complete capping apparatus relative to *S. cerevisiae* or *Candida albicans* cells expressing the fungal organism's capping apparatus indicates that the test compound inhibits the 5' mRNA capping functions of the mammalian organism.

15. The method of claim 14, wherein said test compound is selected from the group consisting of chemicals, drugs and proteins.

16. The method of claim 15, wherein said protein is encoded by a DNA expressed in said *S. cerevisiae* or *Candida albicans* cells, wherein said DNA is operably linked to an inducible promoter.

17. The method of claim 14, wherein said 5' mRNA capping function is selected from the group consisting of RNA triphosphatase, RNA guanylyltransferase, and RNA (guanine-N7)-methyltransferase.

18. A method of screening for a compound that inhibits the catalytic activity of fungal RNA 5' triphosphatase, comprising the steps of:
   a) contacting said fungal RNA 5' triphosphatase with a nucleoside triphosphate and a divalent cation cofactor in the presence and absence of a test compound; and
   b) detecting hydrolysis of said nucleoside triphosphate, wherein a lack of hydrolysis of said nucleoside triphosphate or a decrease in hydrolysis of said nucleoside triphosphate indicates inhibition of said fungal RNA 5' triphosphatase by said test compound.

19. The method of claim 18, wherein said divalent cation cofactor is selected from the group consisting of manganese and cobalt.

20. The method of claim 19, wherein said detection of hydrolysis is selected from the group consisting of a radioisotope assay and a colorimetric assay.

21. The method of claim 18 wherein said fungal RNA triphosphatase is an RNA triphosphatase from *Candida albicans*.

* * * * *

SEQUENCE LISTING

<160> NUMBER OF SEQ ID NOS: 116

<210> SEQ ID NO 1
<211> LENGTH: 6
<212> TYPE: PRT
<213> ORGANISM: Saccharomyces cerevisiae
<220> FEATURE:
<223> OTHER INFORMATION: Motif I of RNA guanylyltransferase.

<400> SEQUENCE: 1

Lys Thr Asp Gly Leu Arg

```
<210> SEQ ID NO 2
<211> LENGTH: 8
<212> TYPE: PRT
<213> ORGANISM: Saccharomyces cerevisiae
<220> FEATURE:
<223> OTHER INFORMATION: Motif III of RNA guanylyltransferase.

<400> SEQUENCE: 2

Thr Leu Leu Asp Gly Glu Leu Val
                5

<210> SEQ ID NO 3
<211> LENGTH: 12
<212> TYPE: PRT
<213> ORGANISM: Saccharomyces cerevisiae
<220> FEATURE:
<223> OTHER INFORMATION: Motif IIIa of RNA guanylyltransferase.

<400> SEQUENCE: 3

Arg Tyr Leu Met Phe Asp Cys Leu Ala Ile Asn Gly
                5                  10

<210> SEQ ID NO 4
<211> LENGTH: 5
<212> TYPE: PRT
<213> ORGANISM: Saccharomyces cerevisiae
<220> FEATURE:
<223> OTHER INFORMATION: Motif IV of RNA guanylyltransferase.

<400> SEQUENCE: 4

Asp Gly Leu Ile Phe
                5

<210> SEQ ID NO 5
<211> LENGTH: 13
<212> TYPE: PRT
<213> ORGANISM: Saccharomyces cerevisiae
<220> FEATURE:
<223> OTHER INFORMATION: Motif V of RNA guanylyltransferase.

<400> SEQUENCE: 5

Leu Leu Lys Trp Leu Pro Glu Gln Glu Asn Thr Val Asp
                5                  10

<210> SEQ ID NO 6
<211> LENGTH: 10
<212> TYPE: PRT
<213> ORGANISM: Saccharomyces cerevisiae
<220> FEATURE:
<223> OTHER INFORMATION: Motif VI of RNA guanylyltransferase.

<400> SEQUENCE: 6

Trp Glu Met Leu Arg Phe Arg Asp Asp Lys
                5                  10

<210> SEQ ID NO 7
<211> LENGTH: 6
<212> TYPE: PRT
<213> ORGANISM: Schizosaccharomyces pombe
<220> FEATURE:
<223> OTHER INFORMATION: Motif I of RNA guanylyltransferase.

<400> SEQUENCE: 7

Lys Ser Asp Gly Ile Arg
                5
```

<210> SEQ ID NO 8
<211> LENGTH: 8
<212> TYPE: PRT
<213> ORGANISM: Schizosaccharomyces pombe
<220> FEATURE:
<223> OTHER INFORMATION: Motif III of RNA guanylyltransferase

<400> SEQUENCE: 8

Thr Leu Leu Asp Gly Glu Leu Val
                5

<210> SEQ ID NO 9
<211> LENGTH: 12
<212> TYPE: PRT
<213> ORGANISM: Schizosaccharomyces pombe
<220> FEATURE:
<223> OTHER INFORMATION: Motif IIIa of RNA guanylyltransferase

<400> SEQUENCE: 9

Arg Tyr Leu Val Phe Asp Cys Leu Ala Cys Asp Gly
                5                   10

<210> SEQ ID NO 10
<211> LENGTH: 5
<212> TYPE: PRT
<213> ORGANISM: Schizosaccharomyces pombe
<220> FEATURE:
<223> OTHER INFORMATION: Motif IV of RNA guanylyltransferase

<400> SEQUENCE: 10

Asp Gly Leu Ile Phe
                5

<210> SEQ ID NO 11
<211> LENGTH: 13
<212> TYPE: PRT
<213> ORGANISM: Schizosaccharomyces pombe
<220> FEATURE:
<223> OTHER INFORMATION: Motif V of RNA guanylyltransferase

<400> SEQUENCE: 11

Leu Leu Lys Trp Lys Pro Lys Glu Met Asn Thr Ile Asp
                5                   10

<210> SEQ ID NO 12
<211> LENGTH: 10
<212> TYPE: PRT
<213> ORGANISM: Schizosaccharomyces pombe
<220> FEATURE:
<223> OTHER INFORMATION: Motif VI of RNA guanylyltransferase

<400> SEQUENCE: 12

Trp Arg Phe Leu Arg Phe Arg Asp Asp Lys
                5                   10

<210> SEQ ID NO 13
<211> LENGTH: 6
<212> TYPE: PRT
<213> ORGANISM: Candida albicans
<220> FEATURE:
<223> OTHER INFORMATION: Motif I of RNA guanylyltransferase.

<400> SEQUENCE: 13

Lys Thr Asp Gly Leu Arg
                5

```
<210> SEQ ID NO 14
<211> LENGTH: 8
<212> TYPE: PRT
<213> ORGANISM: Candida albicans
<220> FEATURE:
<223> OTHER INFORMATION: Motif III of RNA guanylyltransferase.

<400> SEQUENCE: 14

Thr Leu Leu Asp Gly Glu Leu Val
                5

<210> SEQ ID NO 15
<211> LENGTH: 12
<212> TYPE: PRT
<213> ORGANISM: Candida albicans
<220> FEATURE:
<223> OTHER INFORMATION: Motif IIIa of RNA guanylyltransferase.

<400> SEQUENCE: 15

Arg Tyr Val Ile Phe Asp Ala Leu Ala Ile His Gly
                5                  10

<210> SEQ ID NO 16
<211> LENGTH: 5
<212> TYPE: PRT
<213> ORGANISM: Candida albicans
<220> FEATURE:
<223> OTHER INFORMATION: Motif IV of RNA guanylyltransferase.

<400> SEQUENCE: 16

Asp Gly Leu Ile Tyr
                5

<210> SEQ ID NO 17
<211> LENGTH: 13
<212> TYPE: PRT
<213> ORGANISM: Candida albicans
<220> FEATURE:
<223> OTHER INFORMATION: Motif V of RNA guanylyltransferase.

<400> SEQUENCE: 17

Leu Leu Lys Trp Lys Pro Ala Glu Glu Asn Thr Val Asp
                5                  10

<210> SEQ ID NO 18
<211> LENGTH: 10
<212> TYPE: PRT
<213> ORGANISM: Candida albicans
<220> FEATURE:
<223> OTHER INFORMATION: Motif VI of RNA guanylyltransferase.

<400> SEQUENCE: 18

Trp Glu Met Leu Arg Phe Arg Asn Asp Lys
                5                  10

<210> SEQ ID NO 19
<211> LENGTH: 6
<212> TYPE: PRT
<213> ORGANISM: Chlorella virus PBCV-1
<220> FEATURE:
<223> OTHER INFORMATION: Motif I of RNA guanylyltransferase.

<400> SEQUENCE: 19

Lys Thr Asp Gly Ile Arg
                5
```

```
<210> SEQ ID NO 20
<211> LENGTH: 8
<212> TYPE: PRT
<213> ORGANISM: Chlorella virus PBCV-1
<220> FEATURE:
<223> OTHER INFORMATION: Motif III of RNA guanylyltransferase.

<400> SEQUENCE: 20

Ser Ile Phe Asp Gly Glu Leu Cys
                5

<210> SEQ ID NO 21
<211> LENGTH: 12
<212> TYPE: PRT
<213> ORGANISM: Chlorella virus PBCV-1
<220> FEATURE:
<223> OTHER INFORMATION: Motif IIIa of RNA guanylyltransferase.

<400> SEQUENCE: 21

Ala Phe Val Leu Phe Asp Ala Val Val Val Ser Gly
                5                  10

<210> SEQ ID NO 22
<211> LENGTH: 5
<212> TYPE: PRT
<213> ORGANISM: Chlorella virus PBCV-1
<220> FEATURE:
<223> OTHER INFORMATION: Motif IV of RNA guanylyltransferase.

<400> SEQUENCE: 22

Asp Gly Leu Ile Ile
                5

<210> SEQ ID NO 23
<211> LENGTH: 13
<212> TYPE: PRT
<213> ORGANISM: Chlorella virus PBCV-1
<220> FEATURE:
<223> OTHER INFORMATION: Motif V of RNA guanylyltransferase.

<400> SEQUENCE: 23

Leu Phe Lys Leu Lys Pro Gly Thr His His Thr Ile Asp
                5                  10

<210> SEQ ID NO 24
<211> LENGTH: 10
<212> TYPE: PRT
<213> ORGANISM: Chlorella virus PBCV-1
<220> FEATURE:
<223> OTHER INFORMATION: Motif VI of RNA guanylyltransferase.

<400> SEQUENCE: 24

Trp Lys Tyr Ile Gln Gly Arg Ser Asp Lys
                5                  10

<210> SEQ ID NO 25
<211> LENGTH: 6
<212> TYPE: PRT
<213> ORGANISM: Caenorhabditis elegans
<220> FEATURE:
<223> OTHER INFORMATION: Motif I of RNA guanylyltransferase.

<400> SEQUENCE: 25

Lys Ala Asp Gly Met Arg
                5

<210> SEQ ID NO 26
```

```
<211> LENGTH: 8
<212> TYPE: PRT
<213> ORGANISM: Caenorhabditis elegans
<220> FEATURE:
<223> OTHER INFORMATION: Motif III of RNA guanylyltransferase.

<400> SEQUENCE: 26

Thr Leu Val Asp Thr Glu Val Ile
                5

<210> SEQ ID NO 27
<211> LENGTH: 12
<212> TYPE: PRT
<213> ORGANISM: Caenorhabditis elegans
<220> FEATURE:
<223> OTHER INFORMATION: Motif IIIa of RNA guanylyltransferase.

<400> SEQUENCE: 27

Arg Met Leu Ile Tyr Asp Ile Met Arg Phe Asn Ser
                5                  10

<210> SEQ ID NO 28
<211> LENGTH: 5
<212> TYPE: PRT
<213> ORGANISM: Caenorhabditis elegans
<220> FEATURE:
<223> OTHER INFORMATION: Motif IV of RNA guanylyltransferase.

<400> SEQUENCE: 28

Asp Gly Leu Ile Phe
                5

<210> SEQ ID NO 29
<211> LENGTH: 13
<212> TYPE: PRT
<213> ORGANISM: Caenorhabditis elegans
<220> FEATURE:
<223> OTHER INFORMATION: Motif V of RNA guanylyltransferase.

<400> SEQUENCE: 29

Val Leu Lys Trp Lys Pro Pro Ser His Asn Ser Val Asp
                5                  10

<210> SEQ ID NO 30
<211> LENGTH: 10
<212> TYPE: PRT
<213> ORGANISM: Caenorhabditis elegans
<220> FEATURE:
<223> OTHER INFORMATION: Motif VI of RNA guanylyltransferase.

<400> SEQUENCE: 30

Trp Lys Phe Met Arg Glu Arg Thr Asp Lys
                5                  10

<210> SEQ ID NO 31
<211> LENGTH: 6
<212> TYPE: PRT
<213> ORGANISM: Mus
<220> FEATURE:
<223> OTHER INFORMATION: Motif I of RNA guanylyltransferase.

<400> SEQUENCE: 31

Lys Ala Asp Gly Thr Arg
                5

<210> SEQ ID NO 32
<211> LENGTH: 8
```

```
<212> TYPE: PRT
<213> ORGANISM: Mus
<220> FEATURE:
<223> OTHER INFORMATION: Motif III of RNA guanylyltransferase.

<400> SEQUENCE: 32

Thr Leu Leu Asp Gly Glu Met Ile
                5

<210> SEQ ID NO 33
<211> LENGTH: 12
<212> TYPE: PRT
<213> ORGANISM: Mus
<220> FEATURE:
<223> OTHER INFORMATION: Motif IIIa of RNA guanylyltransferase.

<400> SEQUENCE: 33

Arg Tyr Leu Ile Tyr Asp Ile Ile Lys Phe Asn Ala
                5                   10

<210> SEQ ID NO 34
<211> LENGTH: 5
<212> TYPE: PRT
<213> ORGANISM: Mus
<220> FEATURE:
<223> OTHER INFORMATION: Motif IV of RNA guanylyltransferase.

<400> SEQUENCE: 34

Asp Gly Leu Ile Phe
                5

<210> SEQ ID NO 35
<211> LENGTH: 13
<212> TYPE: PRT
<213> ORGANISM: Mus
<220> FEATURE:
<223> OTHER INFORMATION: Motif V of RNA guanylyltransferase.

<400> SEQUENCE: 35

Ile Leu Lys Trp Lys Pro Pro Ser Leu Asn Ser Val Asp
                5                   10

<210> SEQ ID NO 36
<211> LENGTH: 10
<212> TYPE: PRT
<213> ORGANISM: Mus
<220> FEATURE:
<223> OTHER INFORMATION: Motif VI of RNA guanylyltransferase.

<400> SEQUENCE: 36

Trp Val Phe Met Arg Gln Arg Ile Asp Lys
                5                   10

<210> SEQ ID NO 37
<211> LENGTH: 6
<212> TYPE: PRT
<213> ORGANISM: African swine fever virus
<220> FEATURE:
<223> OTHER INFORMATION: Motif I of RNA guanylyltransferase.

<400> SEQUENCE: 37

Lys Ala Asp Gly Ile Arg
                5

<210> SEQ ID NO 38
<211> LENGTH: 8
<212> TYPE: PRT
```

```
<213> ORGANISM: African swine fever virus
<220> FEATURE:
<223> OTHER INFORMATION: Motif III of RNA guanylyltransferase.

<400> SEQUENCE: 38

Thr Ile Leu Asp Gly Glu Phe Met
                5

<210> SEQ ID NO 39
<211> LENGTH: 12
<212> TYPE: PRT
<213> ORGANISM: African swine fever virus
<220> FEATURE:
<223> OTHER INFORMATION: Motif IIIa of RNA guanylyltransferase.

<400> SEQUENCE: 39

Glu Phe Tyr Gly Phe Asp Val Ile Met Tyr Glu Gly
                5                   10

<210> SEQ ID NO 40
<211> LENGTH: 5
<212> TYPE: PRT
<213> ORGANISM: African swine fever virus
<220> FEATURE:
<223> OTHER INFORMATION: Motif IV of RNA guanylyltransferase.

<400> SEQUENCE: 40

Asp Gly Ile Ile Leu
                5

<210> SEQ ID NO 41
<211> LENGTH: 13
<212> TYPE: PRT
<213> ORGANISM: African swine fever virus
<220> FEATURE:
<223> OTHER INFORMATION: Motif V of RNA guanylyltransferase.

<400> SEQUENCE: 41

Thr Phe Lys Trp Lys Pro Thr Trp Asp Asn Thr Leu Asp
                5                   10

<210> SEQ ID NO 42
<211> LENGTH: 10
<212> TYPE: PRT
<213> ORGANISM: African swine fever virus
<220> FEATURE:
<223> OTHER INFORMATION: Motif VI of RNA guanylyltransferase.

<400> SEQUENCE: 42

Trp Glu Ile Val Lys Ile Arg Glu Asp Arg
                5                   10

<210> SEQ ID NO 43
<211> LENGTH: 6
<212> TYPE: PRT
<213> ORGANISM: Trypanosoma brucei gambiense
<220> FEATURE:
<223> OTHER INFORMATION: Motif I of RNA guanylyltransferase.

<400> SEQUENCE: 43

Lys Ala Asp Gly Leu Arg
                5

<210> SEQ ID NO 44
<211> LENGTH: 8
<212> TYPE: PRT
<213> ORGANISM: Trypanosoma brucei gambiense
```

```
<220> FEATURE:
<223> OTHER INFORMATION: Motif III of RNA guanylyltransferase.

<400> SEQUENCE: 44

Phe Leu Leu Asp Thr Glu Val Val
                5

<210> SEQ ID NO 45
<211> LENGTH: 12
<212> TYPE: PRT
<213> ORGANISM: Trypanosoma brucei gambiense
<220> FEATURE:
<223> OTHER INFORMATION: Motif IIIa of RNA guanylyltransferase.

<400> SEQUENCE: 45

Asp Phe Ile Tyr Phe Trp Gly Leu Asp Gly Arg Arg
                5                  10

<210> SEQ ID NO 46
<211> LENGTH: 5
<212> TYPE: PRT
<213> ORGANISM: Trypanosoma brucei gambiense
<220> FEATURE:
<223> OTHER INFORMATION: Motif IV of RNA guanylyltransferase.

<400> SEQUENCE: 46

Asp Gly Leu Ile Phe
                5

<210> SEQ ID NO 47
<211> LENGTH: 13
<212> TYPE: PRT
<213> ORGANISM: Trypanosoma brucei gambiense
<220> FEATURE:
<223> OTHER INFORMATION: Motif V of RNA guanylyltransferase.

<400> SEQUENCE: 47

Leu Ile Lys Trp Lys Pro Val His Leu Cys Thr Val Asp
                5                  10

<210> SEQ ID NO 48
<211> LENGTH: 10
<212> TYPE: PRT
<213> ORGANISM: Trypanosoma brucei gambiense
<220> FEATURE:
<223> OTHER INFORMATION: Motif VI of RNA guanylyltransferase.

<400> SEQUENCE: 48

Trp Thr Phe Arg Asn Ala Arg Asn Asp Lys
                5                  10

<210> SEQ ID NO 49
<211> LENGTH: 6
<212> TYPE: PRT
<213> ORGANISM: Crithidia fasciculata
<220> FEATURE:
<223> OTHER INFORMATION: Motif I of RNA guanylyltransferase.

<400> SEQUENCE: 49

Lys Val Asp Gly Gln Arg
                5

<210> SEQ ID NO 50
<211> LENGTH: 8
<212> TYPE: PRT
<213> ORGANISM: Crithidia fasciculata
<220> FEATURE:
```

-continued

```
<223> OTHER INFORMATION: Motif III of RNA guanylyltransferase.

<400> SEQUENCE: 50

Trp Met Leu Asp Ala Glu Leu Ser
                5

<210> SEQ ID NO 51
<211> LENGTH: 12
<212> TYPE: PRT
<213> ORGANISM: Crithidia fasciculata
<220> FEATURE:
<223> OTHER INFORMATION: Motif IIIa of RNA guanylyltransferase.

<400> SEQUENCE: 51

Asp Tyr Val Phe Phe Gly Gly Lys Gln Ala Lys Arg
                5                   10

<210> SEQ ID NO 52
<211> LENGTH: 5
<212> TYPE: PRT
<213> ORGANISM: Crithidia fasciculata
<220> FEATURE:
<223> OTHER INFORMATION: Motif IV of RNA guanylyltransferase.

<400> SEQUENCE: 52

Asp Gly Leu Val Phe
                5

<210> SEQ ID NO 53
<211> LENGTH: 13
<212> TYPE: PRT
<213> ORGANISM: Crithidia fasciculata
<220> FEATURE:
<223> OTHER INFORMATION: Motif V of RNA guanylyltransferase.

<400> SEQUENCE: 53

Leu Leu Lys Trp Lys Pro Leu Ser Leu Cys Thr Ala Asp
                5                   10

<210> SEQ ID NO 54
<211> LENGTH: 10
<212> TYPE: PRT
<213> ORGANISM: Crithidia fasciculata
<220> FEATURE:
<223> OTHER INFORMATION: Motif VI of RNA guanylyltransferase.

<400> SEQUENCE: 54

Trp Arg Leu His Arg Leu Arg Ser Asp Lys
                5                   10

<210> SEQ ID NO 55
<211> LENGTH: 6
<212> TYPE: PRT
<213> ORGANISM: baculovirus
<220> FEATURE:
<223> OTHER INFORMATION: Motif I of RNA guanylyltransferase.

<400> SEQUENCE: 55

Lys Leu Asp Gly Met Arg
                5

<210> SEQ ID NO 56
<211> LENGTH: 8
<212> TYPE: PRT
<213> ORGANISM: baculovirus
<220> FEATURE:
<223> OTHER INFORMATION: Motif III of RNA guanylyltransferase.
```

<400> SEQUENCE: 56

Val Ala Phe Gln Cys Glu Val Met
                5

<210> SEQ ID NO 57
<211> LENGTH: 12
<212> TYPE: PRT
<213> ORGANISM: baculovirus
<220> FEATURE:
<223> OTHER INFORMATION: Motif IIIa of RNA guanylyltransferase.

<400> SEQUENCE: 57

Asn Arg Thr Gln Tyr Glu Cys Gly Val Asn Ala Ser
                5                   10

<210> SEQ ID NO 58
<211> LENGTH: 5
<212> TYPE: PRT
<213> ORGANISM: AcNPV baculovirus
<220> FEATURE:
<223> OTHER INFORMATION: Motif IV of RNA guanylyltransferase.

<400> SEQUENCE: 58

Asp Gly Tyr Val Val
                5

<210> SEQ ID NO 59
<211> LENGTH: 15
<212> TYPE: PRT
<213> ORGANISM: AcNPV baculovirus
<220> FEATURE:
<223> OTHER INFORMATION: Motif V of RNA guanylyltransferase.

<400> SEQUENCE: 59

Tyr Val Lys Tyr Lys Trp Met Pro Thr Thr Glu Leu Glu Tyr Asp
                5                   10                  15

<210> SEQ ID NO 60
<211> LENGTH: 10
<212> TYPE: PRT
<213> ORGANISM: baculovirus
<220> FEATURE:
<223> OTHER INFORMATION: Motif VI of RNA guanylyltransferase.

<400> SEQUENCE: 60

Ile Asn Val Leu Arg His Arg Arg Asp Arg
                5                   10

<210> SEQ ID NO 61
<211> LENGTH: 6
<212> TYPE: PRT
<213> ORGANISM: vaccinia virus
<220> FEATURE:
<223> OTHER INFORMATION: Motif I of RNA guanylyltransferase.

<400> SEQUENCE: 61

Lys Thr Asp Gly Ile Pro
                5

<210> SEQ ID NO 62
<211> LENGTH: 8
<212> TYPE: PRT
<213> ORGANISM: vaccinia virus
<220> FEATURE:
<223> OTHER INFORMATION: Motif III of RNA guanylyltransferase.

-continued

```
<400> SEQUENCE: 62

Val Val Val Phe Gly Glu Ala Val
                5

<210> SEQ ID NO 63
<211> LENGTH: 12
<212> TYPE: PRT
<213> ORGANISM: vaccinia virus
<220> FEATURE:
<223> OTHER INFORMATION: Motif IIIa of RNA guanylyltransferase.

<400> SEQUENCE: 63

Asn Trp Thr Val Tyr Leu Ile Lys Leu Ile Glu Pro
                5                   10

<210> SEQ ID NO 64
<211> LENGTH: 5
<212> TYPE: PRT
<213> ORGANISM: vaccinia virus
<220> FEATURE:
<223> OTHER INFORMATION: Motif IV of RNA guanylyltransferase.

<400> SEQUENCE: 64

Glu Gly Val Ile Leu
                5

<210> SEQ ID NO 65
<211> LENGTH: 11
<212> TYPE: PRT
<213> ORGANISM: vaccinia virus
<220> FEATURE:
<223> OTHER INFORMATION: Motif V of RNA guanylyltransferase.

<400> SEQUENCE: 65

Asp Phe Lys Ile Lys Lys Glu Asn Thr Ile Asp
                5                   10

<210> SEQ ID NO 66
<211> LENGTH: 10
<212> TYPE: PRT
<213> ORGANISM: vaccinia virus
<220> FEATURE:
<223> OTHER INFORMATION: Motif VI of RNA guanylyltransferase.

<400> SEQUENCE: 66

Gly Glu Ile Leu Lys Pro Arg Ile Asp Lys
                5                   10

<210> SEQ ID NO 67
<211> LENGTH: 6
<212> TYPE: PRT
<213> ORGANISM: Shope fibroma virus
<220> FEATURE:
<223> OTHER INFORMATION: Motif I of RNA guanylyltransferase.

<400> SEQUENCE: 67

Lys Thr Asp Gly Val Gly
                5

<210> SEQ ID NO 68
<211> LENGTH: 8
<212> TYPE: PRT
<213> ORGANISM: Shope fibroma virus
<220> FEATURE:
<223> OTHER INFORMATION: Motif III of RNA guanylyltransferase.

<400> SEQUENCE: 68
```

-continued

Val Thr Leu Tyr Gly Glu Ala Val
5

<210> SEQ ID NO 69
<211> LENGTH: 12
<212> TYPE: PRT
<213> ORGANISM: Shope fibroma virus
<220> FEATURE:
<223> OTHER INFORMATION: Motif IIIa of RNA guanylyltransferase.

<400> SEQUENCE: 69

Val Trp Gln Ile Tyr Leu Ile Lys Leu Ile Thr Pro
5 10

<210> SEQ ID NO 70
<211> LENGTH: 5
<212> TYPE: PRT
<213> ORGANISM: Shope fibroma virus
<220> FEATURE:
<223> OTHER INFORMATION: Motif IV of RNA guanylyltransferase.

<400> SEQUENCE: 70

Glu Gly Val Leu Leu
5

<210> SEQ ID NO 71
<211> LENGTH: 11
<212> TYPE: PRT
<213> ORGANISM: Shope fibroma virus
<220> FEATURE:
<223> OTHER INFORMATION: Motif V of RNA guanylyltransferase.

<400> SEQUENCE: 71

Asp Tyr Lys Ile Lys Leu Asp Asn Thr Asp Asp
5 10

<210> SEQ ID NO 72
<211> LENGTH: 10
<212> TYPE: PRT
<213> ORGANISM: Shope fibroma virus
<220> FEATURE:
<223> OTHER INFORMATION: Motif VI of RNA guanylyltransferase.

<400> SEQUENCE: 72

Gly Glu Ile Leu Asp Pro Arg Ile Asp Lys
5 10

<210> SEQ ID NO 73
<211> LENGTH: 6
<212> TYPE: PRT
<213> ORGANISM: molluscum contagiosum virus
<220> FEATURE:
<223> OTHER INFORMATION: Motif I of RNA guanylyltransferase.

<400> SEQUENCE: 73

Lys Thr Asp Gly Val Pro
5

<210> SEQ ID NO 74
<211> LENGTH: 8
<212> TYPE: PRT
<213> ORGANISM: molluscum contagiosum virus
<220> FEATURE:
<223> OTHER INFORMATION: Motif III of RNA guanylyltransferase.

<400> SEQUENCE: 74

Val Ala Leu Phe Gly Glu Ala Val
            5

<210> SEQ ID NO 75
<211> LENGTH: 12
<212> TYPE: PRT
<213> ORGANISM: molluscum contagiosum virus
<220> FEATURE:
<223> OTHER INFORMATION: Motif IIIa of RNA guanylyltransferase.

<400> SEQUENCE: 75

Gln Leu Thr Val Tyr Leu Ile Lys Leu Met Ala Pro
            5                   10

<210> SEQ ID NO 76
<211> LENGTH: 5
<212> TYPE: PRT
<213> ORGANISM: molluscum contagiosum virus
<220> FEATURE:
<223> OTHER INFORMATION: Motif IV of RNA guanylyltransferase.

<400> SEQUENCE: 76

Glu Gly Val Val Leu
            5

<210> SEQ ID NO 77
<211> LENGTH: 11
<212> TYPE: PRT
<213> ORGANISM: molluscum contagiosum virus
<220> FEATURE:
<223> OTHER INFORMATION: Motif V of RNA guanylyltransferase.

<400> SEQUENCE: 77

Asp Leu Lys Leu Lys Arg Asp Asn Thr Val Asp
            5                   10

<210> SEQ ID NO 78
<211> LENGTH: 10
<212> TYPE: PRT
<213> ORGANISM: molluscum contagiosum virus
<220> FEATURE:
<223> OTHER INFORMATION: Motif VI of RNA guanylyltransferase.

<400> SEQUENCE: 78

Gly Arg Leu Leu Arg Pro Arg Leu Ala Lys
            5                   10

<210> SEQ ID NO 79
<211> LENGTH: 357
<212> TYPE: PRT
<213> ORGANISM: Saccharomyces cerevisiae
<220> FEATURE:
<222> LOCATION: 43..399
<223> OTHER INFORMATION: Amino acid sequence of RNA guanylyltransferase.

<400> SEQUENCE: 79

Phe Pro Gly Ser Gln Pro Val Ser Phe Gln His Ser Asp Val Glu
            5                   10                  15

Glu Lys Leu Leu Ala His Asp Tyr Tyr Val Cys Glu Lys Thr Asp
            20                  25                  30

Gly Leu Arg Val Leu Met Phe Ile Val Ile Asn Pro Val Thr Gly
            35                  40                  45

Glu Gln Gly Cys Phe Met Ile Asp Arg Glu Asn Asn Tyr Tyr Leu
            50                  55                  60

Val Asn Gly Phe Arg Phe Pro Arg Leu Pro Gln Lys Lys Lys Glu

```
                      65                  70                  75
Glu Leu Leu Glu Thr Leu Gln Asp Gly Thr Leu Leu Asp Gly Glu
             80                  85                  90

Leu Val Ile Gln Thr Asn Pro Met Thr Lys Leu Gln Glu Leu Arg
             95                 100                 105

Tyr Leu Met Phe Asp Cys Leu Ala Ile Asn Gly Arg Cys Leu Thr
            110                 115                 120

Gln Ser Pro Thr Ser Ser Arg Leu Ala His Leu Gly Lys Glu Phe
            125                 130                 135

Phe Lys Pro Tyr Phe Asp Leu Arg Ala Ala Tyr Pro Asn Arg Cys
            140                 145                 150

Thr Thr Phe Pro Phe Lys Ile Ser Met Lys His Met Asp Phe Ser
            155                 160                 165

Tyr Gln Leu Val Lys Val Ala Lys Ser Leu Asp Lys Leu Pro His
            170                 175                 180

Leu Ser Asp Gly Leu Ile Phe Thr Pro Val Lys Ala Pro Tyr Thr
            185                 190                 195

Ala Gly Gly Lys Asp Ser Leu Leu Lys Trp Lys Pro Glu Gln
            200                 205                 210

Glu Asn Thr Val Asp Phe Lys Leu Ile Leu Asp Ile Pro Met Val
            215                 220                 225

Glu Asp Pro Ser Leu Pro Lys Asp Asp Arg Asn Arg Trp Tyr Tyr
            230                 235                 240

Asn Tyr Asp Val Lys Pro Val Phe Ser Leu Tyr Val Trp Gln Gly
            245                 250                 255

Gly Ala Asp Val Asn Ser Arg Leu Lys His Phe Asp Gln Pro Phe
            260                 265                 270

Lys Arg Lys Glu Phe Glu Ile Leu Glu Arg Thr Tyr Arg Lys Phe
            275                 280                 285

Ala Glu Leu Ser Val Ser Asp Glu Glu Trp Gln Asn Leu Lys Asn
            290                 295                 300

Leu Glu Gln Pro Leu Asn Gly Arg Ile Val Glu Cys Ala Lys Asn
            305                 310                 315

Gln Glu Thr Gly Ala Trp Glu Met Leu Arg Phe Arg Asp Asp Lys
            320                 325                 330

Leu Asn Gly Asn His Thr Ser Val Val Gln Lys Val Leu Glu Ser
            335                 340                 345

Ile Asn Asp Ser Val Ser Leu Glu Asp Leu Glu Glu
            350                 355

<210> SEQ ID NO 80
<211> LENGTH: 333
<212> TYPE: PRT
<213> ORGANISM: Candida albicans
<220> FEATURE:
<223> OTHER INFORMATION: Amino acid sequence of RNA guanylyltransferase.

<400> SEQUENCE: 80

Phe Pro Gly Ser Gln Pro Val Ser Phe Glu Arg Arg His Leu Glu
              5                  10                  15

Glu Thr Leu Met Gln Lys Asp Tyr Phe Val Cys Glu Lys Thr Asp
             20                  25                  30

Gly Leu Arg Cys Leu Leu Phe Leu Ile Asn Asp Pro Asp Lys Gly
             35                  40                  45

Glu Gly Val Phe Leu Val Thr Arg Glu Asn Asp Tyr Tyr Phe Ile
```

50                  55                  60
Pro Asn Ile His Phe Pro Leu Ser Val Asn Glu Thr Arg Glu Lys
                65                  70                  75
Pro Thr Tyr His His Gly Thr Leu Leu Asp Gly Glu Leu Val Leu
                80                  85                  90
Glu Asn Arg Asn Val Ser Glu Pro Val Leu Arg Tyr Val Ile Phe
                95                 100                 105
Asp Ala Leu Ala Ile His Gly Lys Cys Ile Ile Asp Arg Pro Leu
               110                 115                 120
Pro Lys Arg Leu Gly Tyr Ile Thr Glu Asn Val Met Lys Pro Phe
               125                 130                 135
Asp Asn Phe Lys Lys His Asn Pro Asp Ile Val Asn Ser Pro Glu
               140                 145                 150
Phe Pro Phe Lys Val Gly Phe Lys Thr Met Leu Thr Ser Tyr His
               155                 160                 165
Ala Asp Asp Val Leu Ser Lys Met Asp Lys Leu Phe His Ala Ser
               170                 175                 180
Asp Gly Leu Ile Tyr Thr Cys Ala Glu Thr Pro Tyr Val Phe Gly
               185                 190                 195
Thr Asp Gln Thr Leu Leu Lys Trp Lys Pro Ala Glu Glu Asn Thr
               200                 205                 210
Tyr Asp Phe Gln Leu Glu Phe Val Phe Asn Glu Val Gln Asp Pro
               215                 220                 225
Asp Leu Asp Glu Arg Asp Pro Thr Ser Thr Tyr Leu Asp Tyr Asp
               230                 235                 240
Ala Lys Pro Asn Leu Ile Lys Leu Arg Val Trp Gln Gly Ser Asn
               245                 250                 255
Val His Thr Asp Phe Ala Lys Leu Asp Leu Ser Asp Asp Asp Trp
               260                 265                 270
Glu Arg Leu Lys Ala Leu Glu Gln Pro Leu Gln Gly Arg Ile Ala
               275                 280                 285
Glu Cys Arg Gln Ser Thr Thr Lys Lys Gly Tyr Trp Glu Met Leu
               290                 295                 300
Arg Phe Arg Asn Asp Lys Ser Asn Gly Asn His Ile Ser Val Val
               305                 310                 315
Glu Lys Ile Leu Val Ser Ile Lys Asp Gly Val Lys Glu Lys Glu
               320                 325                 330
Val Ile Glu

<210> SEQ ID NO 81
<211> LENGTH: 318
<212> TYPE: PRT
<213> ORGANISM: Schizosaccharomyces pombe
<220> FEATURE:
<223> OTHER INFORMATION: Amino acid sequence of RNA guanylyltransferase.

<400> SEQUENCE: 81

Phe Pro Gly Ser Gln Glu Val Ser Phe Ser Lys Lys His Leu Gln
                 5                  10                  15
Ala Leu Lys Glu Lys Asn Tyr Phe Val Cys Glu Lys Ser Asp Gly
                20                  25                  30
Ile Arg Cys Leu Leu Tyr Met Thr Glu His Pro Arg Tyr Glu Asn
                35                  40                  45
Arg Pro Ser Val Tyr Leu Glu Asp Arg Lys Met Asn Phe Tyr His
                50                  55                  60

Val Glu Lys Ile Phe Tyr Pro Val Glu Asn Asp Lys Ser Gly Lys
                65                  70                  75

Lys Tyr His Val Asp Thr Leu Leu Asp Gly Glu Leu Val Leu Asp
                80                  85                  90

Ile Tyr Pro Gly Gly Lys Lys Gln Leu Arg Tyr Leu Val Phe Asp
                95                 100                 105

Cys Leu Ala Cys Asp Gly Ile Val Tyr Met Ser Arg Leu Leu Asp
               110                 115                 120

Lys Arg Leu Gly Ile Phe Ala Lys Ser Ile Gln Lys Pro Leu Asp
               125                 130                 135

Glu Tyr Thr Lys Thr His Met Arg Glu Thr Ala Ile Phe Pro Phe
               140                 145                 150

Leu Thr Ser Leu Lys Lys Met Glu Leu Gly His Gly Ile Leu Lys
               155                 160                 165

Leu Phe Asn Glu Val Ile Pro Arg Leu Arg His Gly Asn Asp Gly
               170                 175                 180

Leu Ile Phe Thr Cys Thr Glu Thr Pro Tyr Val Ser Gly Thr Asp
               185                 190                 195

Gln Ser Leu Leu Lys Trp Lys Pro Lys Glu Met Asn Thr Ile Asp
               200                 205                 210

Phe Met Leu Lys Leu Glu Phe Ala Gln Pro Glu Gly Asp Ile
               215                 220                 225

Asp Tyr Ser Ala Met Pro Glu Phe Gln Leu Gly Val Trp Glu Gly
               230                 235                 240

Arg Asn Met Tyr Ser Phe Phe Ala Phe Met Tyr Val Asp Glu Lys
               245                 250                 255

Glu Trp Glu Lys Leu Lys Ser Phe Asn Val Pro Leu Ser Glu Arg
               260                 265                 270

Ile Val Glu Cys Tyr Leu Asp Asp Glu Asn Arg Trp Arg Phe Leu
               275                 280                 285

Arg Phe Arg Asp Asp Lys Arg Asp Ala Asn His Ile Ser Thr Val
               290                 295                 300

Lys Ser Val Leu Gln Ser Ile Glu Asp Gly Val Ser Lys Glu Asp
               305                 310                 315

Leu Leu Lys

<210> SEQ ID NO 82
<211> LENGTH: 293
<212> TYPE: PRT
<213> ORGANISM: Mus
<220> FEATURE:
<223> OTHER INFORMATION: Amino acid sequence of RNA guanylyltransferase.

<400> SEQUENCE: 82

Phe Pro Gly Ala Gln Pro Val Ser Met Asp Lys Gln Asn Ile Arg
                 5                  10                  15

Leu Leu Glu Gln Lys Pro Tyr Val Ser Trp Lys Ala Asp Gly
                20                  25                  30

Thr Arg Tyr Met Met Leu Ile Asp Gly Thr Asn Glu Val Phe Met
                35                  40                  45

Ile Asp Arg Asp Asn Ser Val Phe His Val Ser Asn Leu Glu Phe
                50                  55                  60

Pro Phe Arg Lys Asp Leu Arg Met His Leu Ser Asn Thr Leu Leu
                65                  70                  75

-continued

```
Asp Gly Glu Met Ile Ile Asp Lys Val Asn Gly Gln Ala Val Pro
            80                  85                  90

Arg Tyr Leu Ile Tyr Asp Ile Ile Lys Phe Asn Ala Gln Pro Val
            95                 100                 105

Gly Asp Cys Asp Phe Asn Ile Arg Leu Gln Cys Ile Glu Arg Glu
           110                 115                 120

Ile Ile Ser Pro Arg His Glu Lys Met Lys Thr Gly Leu Ile Asp
           125                 130                 135

Lys Thr Gln Glu Pro Phe Ser Val Arg Arg Lys Gln Phe Phe Asp
           140                 145                 150

Ile Asn Ile Ser Arg Lys Leu Leu Glu Gly Asn Phe Ala Lys Glu
           155                 160                 165

Val Ser His Glu Met Asp Gly Leu Ile Phe Gln Pro Ile Gly Lys
           170                 175                 180

Tyr Lys Pro Gly Arg Cys Asp Asp Ile Leu Lys Trp Lys Pro Pro
           185                 190                 195

Ser Leu Asn Ser Val Asp Phe Arg Leu Lys Ile Thr Arg Met Gly
           200                 205                 210

Gly Glu Gly Leu Leu Pro Gln Asn Val Gly Leu Leu Tyr Val Gly
           215                 220                 225

Gly Tyr Glu Arg Pro Phe Ala Gln Ile Lys Val Thr Lys Glu Leu
           230                 235                 240

Lys Gln Tyr Asp Asn Lys Ile Ile Glu Cys Lys Phe Glu Asn Asn
           245                 250                 255

Ser Trp Val Phe Met Arg Gln Arg Ile Asp Lys Ser Phe Pro Asn
           260                 265                 270

Ala Tyr Asn Thr Ala Met Ala Val Cys Asn Ser Ile Ser Asn Pro
           275                 280                 285

Val Thr Lys Glu Met Leu Phe Glu
           290
```

<210> SEQ ID NO 83
<211> LENGTH: 254
<212> TYPE: PRT
<213> ORGANISM: Caenorhabditis elegans
<220> FEATURE:
<223> OTHER INFORMATION: Amino acid sequence of RNA guanylyltransferase.

<400> SEQUENCE: 83

```
Phe Pro Gly Leu Gln Pro Val Ser Leu Ser Arg Gly Asn Ile Asn
             5                  10                  15

Leu Leu Glu Gln Glu Ser Tyr Met Val Ser Trp Lys Ala Asp Gly
            20                  25                  30

Met Arg Tyr Ile Ile Tyr Ile Asn Asp Gly Asp Val Tyr Ala Phe
            35                  40                  45

Asp Arg Asp Asn Glu Val Phe Glu Ile Glu Asn Leu Asp Phe Val
            50                  55                  60

Thr Lys Asn Gly Ala Pro Leu Met Glu Thr Leu Val Asp Thr Glu
            65                  70                  75

Val Ile Ile Asp Lys Val Glu Ile Asn Gly Ala Met Cys Asp Gln
            80                  85                  90

Pro Arg Met Leu Ile Tyr Asp Ile Met Arg Phe Asn Ser Val Asn
            95                 100                 105

Val Met Lys Glu Pro Phe Tyr Lys Arg Phe Glu Ile Ile Lys Thr
           110                 115                 120
```

-continued

```
Glu Ile Ile Asp Met Arg Thr Ala Ala Phe Lys Thr Gly Arg Leu
            125                 130                 135

Lys His Glu Asn Gln Ile Met Ser Val Arg Arg Lys Asp Phe Tyr
            140                 145                 150

Asp Leu Glu Ala Thr Ala Lys Leu Phe Gly Pro Lys Phe Val Gln
            155                 160                 165

His Val Gly His Pro Glu Trp Ile Gly Tyr Leu Phe Val Gln Asn
            170                 175                 180

Leu Ser Asp Pro Phe Gly Thr Met Ala Lys Ala Thr Ala Thr Leu
            185                 190                 195

Lys Lys Tyr His Asn Lys Ile Ile Glu Cys Thr Leu Leu Val Asp
            200                 205                 210

Asn Gln Gly Arg Pro Lys Glu Trp Lys Phe Met Arg Glu Arg Thr
            215                 220                 225

Asp Lys Ser Leu Pro Asn Gly Leu Arg Thr Ala Glu Asn Val Val
            230                 235                 240

Glu Thr Met Val Asn Pro Val Thr Glu Thr Tyr Leu Ile Glu
            245                 250
```

<210> SEQ ID NO 84
<211> LENGTH: 270
<212> TYPE: PRT
<213> ORGANISM: Chlorella virus PBCV-1
<220> FEATURE:
<223> OTHER INFORMATION: Amino acid sequence of RNA guanylyltransferase.

<400> SEQUENCE: 84

```
Leu Pro Gly Pro Asn Pro Val Ser Ile Glu Arg Lys Asp Phe Glu
              5                  10                  15

Lys Leu Lys Gln Asn Lys Tyr Val Val Ser Glu Lys Thr Asp Gly
             20                  25                  30

Ile Arg Phe Met Met Phe Phe Thr Arg Val Phe Gly Phe Lys Val
             35                  40                  45

Cys Thr Ile Ile Asp Arg Ala Met Thr Val Tyr Leu Leu Pro Phe
             50                  55                  60

Lys Asn Ile Pro Arg Val Leu Phe Gln Gly Ser Ile Phe Asp Gly
             65                  70                  75

Glu Leu Cys Val Asp Ile Val Glu Lys Lys Phe Ala Phe Val Leu
             80                  85                  90

Phe Asp Ala Val Val Ser Gly Val Thr Val Ser Gln Met Asp
             95                 100                 105

Leu Ala Ser Arg Phe Phe Ala Met Lys Arg Ser Leu Lys Glu Phe
            110                 115                 120

Lys Asn Val Pro Glu Asp Pro Ala Ile Leu Arg Tyr Lys Glu Trp
            125                 130                 135

Ile Pro Leu Glu His Pro Thr Ile Ile Lys Asp His Leu Lys Lys
            140                 145                 150

Ala Asn Ala Ile Tyr His Thr Asp Gly Leu Ile Ile Met Ser Val
            155                 160                 165

Asp Glu Pro Val Ile Tyr Gly Arg Asn Phe Asn Leu Phe Lys Leu
            170                 175                 180

Lys Pro Gly Thr His His Thr Ile Asp Phe Ile Ile Met Ser Glu
            185                 190                 195

Asp Gly Thr Ile Gly Ile Phe Asp Pro Asn Leu Arg Lys Asn Val
            200                 205                 210
```

```
Pro Val Gly Lys Leu Asp Gly Tyr Tyr Asn Lys Gly Ser Ile Val
                215                 220                 225

Glu Cys Gly Phe Ala Asp Gly Thr Trp Lys Tyr Ile Gln Gly Arg
                230                 235                 240

Ser Asp Lys Asn Gln Ala Asn Asp Arg Leu Thr Tyr Glu Lys Thr
                245                 250                 255

Leu Leu Asn Ile Glu Glu Asn Ile Thr Ile Asp Glu Leu Leu Asp
                260                 265                 270

<210> SEQ ID NO 85
<211> LENGTH: 168
<212> TYPE: PRT
<213> ORGANISM: baculovirus
<220> FEATURE:
<223> OTHER INFORMATION: Amino acid sequence of RNA baculovirus
      phosphatase BVP.

<400> SEQUENCE: 85

Met Phe Pro Ala Arg Trp His Asn Tyr Leu Gln Cys Gly Gln Val
                  5                  10                  15

Ile Lys Asp Ser Asn Leu Ile Cys Phe Lys Thr Pro Leu Arg Pro
                 20                  25                  30

Glu Leu Phe Ala Tyr Val Thr Ser Glu Glu Asp Val Trp Thr Ala
                 35                  40                  45

Glu Gln Ile Val Lys Gln Asn Pro Ser Ile Gly Ala Ile Ile Asp
                 50                  55                  60

Leu Thr Asn Thr Ser Lys Tyr Tyr Asp Gly Val His Phe Leu Arg
                 65                  70                  75

Ala Gly Leu Leu Tyr Lys Lys Ile Gln Val Pro Gly Gln Thr Leu
                 80                  85                  90

Pro Pro Glu Ser Ile Val Gln Glu Phe Ile Asp Thr Val Lys Glu
                 95                 100                 105

Phe Thr Glu Lys Cys Pro Gly Met Leu Val Gly Val His Cys Thr
                110                 115                 120

His Gly Ile Asn Arg Thr Gly Tyr Met Val Cys Arg Tyr Leu Met
                125                 130                 135

His Thr Leu Gly Ile Ala Pro Gln Glu Ala Ile Asp Arg Phe Glu
                140                 145                 150

Lys Ala Arg Gly His Lys Ile Glu Arg Gln Asn Tyr Val Gln Asp
                155                 160                 165

Leu Leu Ile

<210> SEQ ID NO 86
<211> LENGTH: 175
<212> TYPE: PRT
<213> ORGANISM: Mus
<220> FEATURE:
<223> OTHER INFORMATION: Amino acid sequence of N-terminal RNA
      triphosphatase domain of the capping enzyme.

<400> SEQUENCE: 86

Met Ala Tyr Asn Lys Ile Pro Pro Arg Trp Leu Asn Cys Pro Arg
                  5                  10                  15

Arg Gly Gln Pro Val Ala Gly Arg Phe Leu Pro Leu Lys Thr Met
                 20                  25                  30

Leu Gly Pro Arg Tyr Asp Ser Gln Val Ala Glu Glu Asn Arg Phe
                 35                  40                  45

His Pro Ser Met Leu Ser Asn Tyr Leu Lys Ser Leu Lys Val Lys
```

```
                    50                  55                  60
Met Ser Leu Leu Val Asp Leu Thr Asn Thr Ser Arg Phe Tyr Asp
                65                  70                  75

Arg Asn Asp Ile Glu Lys Glu Gly Ile Lys Tyr Ile Lys Leu Gln
                80                  85                  90

Cys Lys Gly His Gly Glu Cys Pro Thr Thr Glu Asn Thr Glu Thr
                95                  100                 105

Phe Ile Arg Leu Cys Glu Arg Phe Asn Glu Arg Ser Pro Pro Glu
                110                 115                 120

Leu Ile Gly Val His Cys Thr His Cys Phe Asn Arg Thr Gly Phe
                125                 130                 135

Leu Ile Cys Ala Phe Leu Val Glu Lys Met Asp Trp Ser Ile Glu
                140                 145                 150

Ala Ala Val Ala Thr Phe Ala Gln Ala Arg Pro Pro Gly Ile Tyr
                155                 160                 165

Lys Gly Asp Tyr Leu Lys Glu Leu Phe Arg
                170                 175

<210> SEQ ID NO 87
<211> LENGTH: 173
<212> TYPE: PRT
<213> ORGANISM: Candida albicans
<220> FEATURE:
<223> OTHER INFORMATION: Amino acid sequence of N-terminal RNA
      triphosphatase domain of the capping enzyme.

<400> SEQUENCE: 87

Met Gly Leu Pro Asp Arg Trp Leu His Cys Pro Lys Thr Gly Thr
                5                   10                  15

Leu Ile Asn Asn Leu Phe Phe Pro Phe Lys Thr Pro Leu Cys Lys
                20                  25                  30

Met Tyr Asp Asn Gln Ile Ala Glu Arg Arg Tyr Gln Arg His Pro
                35                  40                  45

Ala Glu Val Phe Ser His Pro His Leu His Gly Lys Lys Ile Gly
                50                  55                  60

Leu Trp Ile Asp Leu Thr Asn Thr Asp Arg Tyr Tyr Phe Arg Glu
                65                  70                  75

Glu Val Thr Glu His Glu Cys Ile Tyr His Lys Met Lys Met Ala
                80                  85                  90

Gly Arg Gly Val Ser Pro Thr Gln Glu Asp Thr Asp Asn Phe Ile
                95                  100                 105

Lys Leu Val Gln Glu Phe His Lys Lys Tyr Pro Asp Arg Val Val
                110                 115                 120

Gly Val His Cys Thr His Gly Phe Asn Arg Thr Gly Phe Leu Ile
                125                 130                 135

Ala Ala Tyr Leu Phe Gln Val Glu Glu Tyr Gly Leu Asp Ala Ala
                140                 145                 150

Ile Gly Glu Phe Ala Glu Asn Arg Gln Lys Gly Ile Tyr Lys Gln
                155                 160                 165

Asp Tyr Ile Asp Asp Leu Phe Ala
                170

<210> SEQ ID NO 88
<211> LENGTH: 9
<212> TYPE: PRT
<213> ORGANISM: Saccharomyces cerevisiae
<220> FEATURE:
```

```
<223> OTHER INFORMATION: Motif A of RNA triphosphatase.

<400> SEQUENCE: 88

Ser Phe Ile Glu Leu Glu Met Lys Phe
                5

<210> SEQ ID NO 89
<211> LENGTH: 14
<212> TYPE: PRT
<213> ORGANISM: Saccharomyces cerevisiae
<220> FEATURE:
<223> OTHER INFORMATION: Motif B of RNA triphosphatase.

<400> SEQUENCE: 89

Ile Ser Glu Arg Thr Lys Asp Arg Val Ser Tyr Ile His Asn
                5                   10

<210> SEQ ID NO 90
<211> LENGTH: 7
<212> TYPE: PRT
<213> ORGANISM: Saccharomyces cerevisiae
<220> FEATURE:
<223> OTHER INFORMATION: Motif C of RNA triphosphatase.

<400> SEQUENCE: 90

Thr His Glu Val Glu Leu Glu
                5

<210> SEQ ID NO 91
<211> LENGTH: 9
<212> TYPE: PRT
<213> ORGANISM: vaccinia virus
<220> FEATURE:
<223> OTHER INFORMATION: Motif A of RNA triphosphatase.

<400> SEQUENCE: 91

Ile Asn Asn Glu Leu Glu Leu Val Phe
                5

<210> SEQ ID NO 92
<211> LENGTH: 14
<212> TYPE: PRT
<213> ORGANISM: vaccinia virus
<220> FEATURE:
<223> OTHER INFORMATION: Motif B of RNA triphosphatase.

<400> SEQUENCE: 92

Val Lys Ile Arg Thr Lys Ile Pro Leu Ser Lys Val His Gly
                5                   10

<210> SEQ ID NO 93
<211> LENGTH: 7
<212> TYPE: PRT
<213> ORGANISM: vaccinia virus
<220> FEATURE:
<223> OTHER INFORMATION: Motif C of RNA triphosphatase.

<400> SEQUENCE: 93

Ser Leu Glu Ile Glu Phe Thr
                5

<210> SEQ ID NO 94
<211> LENGTH: 9
<212> TYPE: PRT
<213> ORGANISM: Shope fibroma virus
<220> FEATURE:
<223> OTHER INFORMATION: Motif A of RNA triphosphatase.
```

<400> SEQUENCE: 94

Met Asn His Glu Val Glu Leu Thr Phe
                5

<210> SEQ ID NO 95
<211> LENGTH: 14
<212> TYPE: PRT
<213> ORGANISM: Shope fibroma virus
<220> FEATURE:
<223> OTHER INFORMATION: Motif B of RNA triphosphatase.

<400> SEQUENCE: 95

Val Lys Ile Arg Asn Arg Ile Asn Leu Ser Lys Ile His Gly
                5                   10

<210> SEQ ID NO 96
<211> LENGTH: 7
<212> TYPE: PRT
<213> ORGANISM: Shope fibroma virus
<220> FEATURE:
<223> OTHER INFORMATION: Motif C of RNA triphosphatase.

<400> SEQUENCE: 96

Ser Leu Glu Phe Glu Ile Ile
                5

<210> SEQ ID NO 97
<211> LENGTH: 9
<212> TYPE: PRT
<213> ORGANISM: molluscum contagiosum virus
<220> FEATURE:
<223> OTHER INFORMATION: Motif A of RNA triphosphatase.

<400> SEQUENCE: 97

Val His His Glu Val Glu Leu Ile Phe
                5

<210> SEQ ID NO 98
<211> LENGTH: 14
<212> TYPE: PRT
<213> ORGANISM: molluscum contagiosum virus
<220> FEATURE:
<223> OTHER INFORMATION: Motif B of RNA triphosphatase.

<400> SEQUENCE: 98

Val Lys Leu Arg Thr Arg Leu Pro Leu Ala Thr Val His Gly
                5                   10

<210> SEQ ID NO 99
<211> LENGTH: 7
<212> TYPE: PRT
<213> ORGANISM: molluscum contagiosum virus
<220> FEATURE:
<223> OTHER INFORMATION: Motif C of RNA triphosphatase.

<400> SEQUENCE: 99

Thr Leu Glu Phe Glu Val Leu
                5

<210> SEQ ID NO 100
<211> LENGTH: 9
<212> TYPE: PRT
<213> ORGANISM: African swine fever virus
<220> FEATURE:
<223> OTHER INFORMATION: Motif A of RNA triphosphatase.

```
<400> SEQUENCE: 100

Ser Thr Ile Glu Leu Glu Ile Arg Phe
                5

<210> SEQ ID NO 101
<211> LENGTH: 14
<212> TYPE: PRT
<213> ORGANISM: African swine fever virus
<220> FEATURE:
<223> OTHER INFORMATION: Motif B of RNA triphosphatase.

<400> SEQUENCE: 101

Asn His Cys Arg Glu Lys Ile Leu Pro Ser Glu Asn Leu Tyr
                5                  10

<210> SEQ ID NO 102
<211> LENGTH: 7
<212> TYPE: PRT
<213> ORGANISM: molluscum contagiosum virus
<220> FEATURE:
<223> OTHER INFORMATION: African swine fever virus.

<400> SEQUENCE: 102

Leu Tyr Glu Ile Glu Ile Glu
                5

<210> SEQ ID NO 103
<211> LENGTH: 9
<212> TYPE: PRT
<213> ORGANISM: baculovirus
<220> FEATURE:
<223> OTHER INFORMATION: Motif A of RNA triphosphatase.

<400> SEQUENCE: 103

Phe Val Ile Glu Lys Glu Ile Ser Tyr
                5

<210> SEQ ID NO 104
<211> LENGTH: 14
<212> TYPE: PRT
<213> ORGANISM: baculovirus
<220> FEATURE:
<223> OTHER INFORMATION: Motif B of RNA triphosphatase.

<400> SEQUENCE: 104

Asn Gly Phe Arg Thr Arg Ile Pro Ile Gln Ser Ala Cys Asn
                5                  10

<210> SEQ ID NO 105
<211> LENGTH: 7
<212> TYPE: PRT
<213> ORGANISM: baculovirus
<220> FEATURE:
<223> OTHER INFORMATION: Motif C of RNA triphosphatase.

<400> SEQUENCE: 105

Arg Leu Glu Tyr Glu Phe Asp
                5

<210> SEQ ID NO 106
<211> LENGTH: 9
<212> TYPE: PRT
<213> ORGANISM: Saccharomyces cerevisiae
<220> FEATURE:
<223> OTHER INFORMATION: Motif A of RNA triphosphatase.

<400> SEQUENCE: 106
```

```
Ser His Ile Glu Ile Glu Met Lys Phe
                5

<210> SEQ ID NO 107
<211> LENGTH: 14
<212> TYPE: PRT
<213> ORGANISM: Saccharomyces cerevisiae
<220> FEATURE:
<223> OTHER INFORMATION: Motif B of RNA triphosphatase.

<400> SEQUENCE: 107

Ile Leu Gln Arg Thr Lys Ser Arg Ser Thr Tyr Thr Phe Asn
                5                   10

<210> SEQ ID NO 108
<211> LENGTH: 7
<212> TYPE: PRT
<213> ORGANISM: Saccharomyces cerevisiae
<220> FEATURE:
<223> OTHER INFORMATION: Motif C of RNA triphosphatase.

<400> SEQUENCE: 108

Ser His Glu Val Glu Val Glu
                5

<210> SEQ ID NO 109
<211> LENGTH: 9
<212> TYPE: PRT
<213> ORGANISM: Candida albicans
<220> FEATURE:
<223> OTHER INFORMATION: Motif A of RNA triphosphatase.

<400> SEQUENCE: 109

Arg Asn Val Glu Leu Glu Leu Lys Phe
                5

<210> SEQ ID NO 110
<211> LENGTH: 14
<212> TYPE: PRT
<213> ORGANISM: Candida albicans
<220> FEATURE:
<223> OTHER INFORMATION: Motif B of RNA triphosphatase.

<400> SEQUENCE: 110

Glu Met Val Arg Glu Lys Lys Arg Ile Ser Tyr Thr His Pro
                5                   10

<210> SEQ ID NO 111
<211> LENGTH: 7
<212> TYPE: PRT
<213> ORGANISM: Candida albicans
<220> FEATURE:
<223> OTHER INFORMATION: Motif C of RNA triphosphatase.

<400> SEQUENCE: 111

Lys Tyr Glu Val Glu Leu Glu
                5

<210> SEQ ID NO 112
<211> LENGTH: 436
<212> TYPE: PRT
<213> ORGANISM: Saccharomyces cerevisiae
<220> FEATURE:
<223> OTHER INFORMATION: Amino acid sequence of yeast cap
      methyltransferase.

<400> SEQUENCE: 112
```

-continued

```
Met Ser Thr Lys Pro Glu Lys Pro Ile Trp Met Ser Gln Glu Asp
              5                  10                  15

Tyr Asp Arg Gln Tyr Gly Ser Ile Thr Gly Asp Glu Ser Ser Thr
             20                  25                  30

Val Ser Lys Lys Asp Ser Lys Val Thr Ala Asn Ala Pro Gly Asp
             35                  40                  45

Gly Asn Gly Ser Leu Pro Val Leu Gln Ser Ser Ile Leu Thr
             50                  55                  60

Ser Lys Val Ser Asp Leu Pro Ile Glu Ala Glu Ser Gly Phe Lys
             65                  70                  75

Ile Gln Lys Arg Arg His Glu Arg Tyr Asp Gln Glu Glu Arg Leu
             80                  85                  90

Arg Lys Gln Arg Ala Gln Lys Leu Arg Glu Glu Gln Leu Asp Arg
             95                 100                 105

His Glu Ile Glu Met Thr Ala Asn Arg Ser Ile Asn Val Asp Gln
            110                 115                 120

Ile Val Arg Glu His Tyr Asn Glu Arg Thr Ile Ile Ala Asn Arg
            125                 130                 135

Ala Lys Arg Asn Leu Ser Pro Ile Ile Lys Leu Arg Asn Phe Asn
            140                 145                 150

Asn Ala Ile Lys Tyr Met Leu Ile Asp Lys Tyr Thr Lys Pro Gly
            155                 160                 165

Asp Val Val Leu Glu Leu Gly Cys Gly Lys Gly Gly Asp Leu Arg
            170                 175                 180

Lys Tyr Gly Ala Ala Gly Ile Ser Gln Phe Ile Gly Ile Asp Ile
            185                 190                 195

Ser Asn Ala Ser Ile Gln Glu Ala His Lys Arg Tyr Arg Ser Met
            200                 205                 210

Arg Asn Leu Asp Tyr Gln Val Val Leu Ile Thr Gly Asp Cys Phe
            215                 220                 225

Gly Glu Ser Leu Gly Val Ala Val Glu Pro Phe Pro Asp Cys Arg
            230                 235                 240

Phe Pro Cys Asp Ile Val Ser Thr Gln Phe Cys Leu His Tyr Ala
            245                 250                 255

Phe Glu Thr Glu Glu Lys Ala Arg Arg Ala Leu Leu Asn Val Ala
            260                 265                 270

Lys Ser Leu Lys Ile Gly Gly His Phe Phe Gly Thr Ile Pro Asp
            275                 280                 285

Ser Glu Phe Ile Arg Tyr Lys Leu Asn Lys Phe Pro Lys Glu Val
            290                 295                 300

Glu Lys Pro Ser Trp Gly Asn Ser Ile Tyr Lys Val Thr Phe Glu
            305                 310                 315

Asn Asn Ser Tyr Gln Lys Asn Asp Tyr Glu Phe Thr Ser Pro Tyr
            320                 325                 330

Gly Met Tyr Thr Tyr Trp Leu Glu Ala Asp Ala Ile Asp Asn Val
            335                 340                 345

Pro Glu Tyr Val Val Pro Phe Glu Thr Leu Arg Ser Leu Ala Asp
            350                 355                 360

Glu Tyr Gly Leu Glu Leu Val Ser Gln Met Pro Phe Asn Lys Phe
            365                 370                 375

Phe Val Gln Glu Ile Pro Lys Trp Ile Glu Arg Phe Ser Pro Lys
            380                 385                 390
```

-continued

```
Met Arg Glu Gly Leu Gln Arg Ser Asp Gly Arg Tyr Gly Val Glu
                395                 400                 405

Gly Asp Glu Lys Glu Ala Ala Ser Tyr Phe Tyr Thr Met Phe Ala
                410                 415                 420

Arg Arg Lys Val Lys Gln Tyr Ile Glu Pro Glu Ser Val Lys Pro
                425                 430                 435

Asn
```

<210> SEQ ID NO 113
<211> LENGTH: 373
<212> TYPE: PRT
<213> ORGANISM: Candida albicans
<220> FEATURE:
<223> OTHER INFORMATION: Predicted sequence of cap methyltransferase;
      Genbank accession Z81038.

<400> SEQUENCE: 113

```
Met Met Lys Glu Val Leu Asp Ala Phe Arg Lys Ser Gly Glu Ala
                 5                  10                  15

Glu Gly Phe Gly His Asn Lys Met Ser Ser Ser Glu Val Ala Ser
                20                  25                  30

His Tyr Asn Lys Val Leu Gln Val Gly Ile Glu Gly Arg Lys Glu
                35                  40                  45

Ser Arg Ile Phe Phe Met Arg Asn Met Asn Asn Trp Val Lys Ser
                50                  55                  60

Gln Leu Ile Asn Asp Ala Lys Gln Arg Val Asn Asp Asn Gly Val
                65                  70                  75

Asn Asn Pro Arg Val Leu Asp Leu Ala Cys Gly Lys Gly Gly Asp
                80                  85                  90

Leu Lys Lys Trp Asp Ile Ala Gly Ala Lys Asp Val Val Met Ala
                95                  100                 105

Asp Val Ala Asp Val Ser Ile Gln Gln Ala Glu Arg Tyr Lys
                110                 115                 120

Gln Met Phe Gly Tyr Lys Lys Asn Asn Ile Phe Thr Val Gln Phe
                125                 130                 135

Ile Val Ala Asp Cys Thr Lys Glu Asn Leu Glu Asp Arg Ile Glu
                140                 145                 150

Asn Lys Asp Pro Phe Asp Leu Val Ser Cys Gln Phe Ala Leu His
                155                 160                 165

Tyr Ser Phe Val Asp Glu Ala Ser Ala Arg Ile Phe Leu Lys Asn
                170                 175                 180

Ala Val Gly Met Leu Lys Pro Gly Gly Val Phe Ile Gly Thr Leu
                185                 190                 195

Pro Asp Ala Asp Arg Ile Val Trp Ser Met Arg Asn Gly Glu Asn
                200                 205                 210

Gly Gln Phe Ala Asn Glu Val Cys Lys Ile Thr Tyr Glu Asn Val
                215                 220                 225

Glu Glu Leu Ala Glu Gly Lys Val Pro Leu Phe Gly Ala Lys Phe
                230                 235                 240

His Phe Ser Leu Asp Glu Gln Val Asn Cys Pro Glu Phe Leu Ala
                245                 250                 255

Tyr Phe Pro Leu Val Lys His Leu Leu Glu Glu Leu Asp Met Glu
                260                 265                 270

Leu Leu Phe Val His Asn Phe Ala Glu Ala Ile Asn Lys Trp Leu
                275                 280                 285
```

```
Glu Pro Gly Arg Arg Leu Leu Glu Ser Met Thr Gly Leu Glu Thr
                290                 295                 300

Tyr Pro Asn Glu Lys Leu Ser Gly Lys Ser Asp Asp Glu Tyr Leu
                305                 310                 315

Glu Ala Lys Ala Lys Leu Asp Ala Phe Pro Glu Asp Glu Arg Ile
                320                 325                 330

Lys Thr Met Gly Thr Leu Ser Lys Ser Glu Trp Glu Ala Ile Cys
                335                 340                 345

Met Tyr Leu Val Phe Gly Phe Arg Lys Lys Ser Glu Ala Glu
                350                 355                 360

Lys Thr Glu Glu Glu Pro Ala Thr Thr Lys Pro Val Ala
                365                 370

<210> SEQ ID NO 114
<211> LENGTH: 476
<212> TYPE: PRT
<213> ORGANISM: Homo sapiens
<220> FEATURE:
<223> OTHER INFORMATION: Amino acid sequence of human cap
      methyltransferase.

<400> SEQUENCE: 114

Met Ala Asn Ser Ala Lys Ala Glu Glu Tyr Glu Lys Met Ser Leu
                  5                  10                  15

Glu Ala Gln Ala Lys Ala Ser Val Asn Ser Glu Thr Glu Ser Ser
                 20                  25                  30

Phe Asn Ile Asn Glu Asn Thr Thr Ala Ser Gly Thr Gly Leu Ser
                 35                  40                  45

Glu Lys Thr Ser Val Cys Arg Gln Val Asp Ile Ala Arg Lys Arg
                 50                  55                  60

Lys Glu Phe Glu Asp Asp Leu Val Lys Glu Ser Ser Cys Gly
                 65                  70                  75

Lys Asp Thr Pro Ser Lys Lys Arg Lys Leu Asp Pro Glu Ile Val
                 80                  85                  90

Pro Glu Glu Lys Asp Cys Gly Asp Ala Glu Gly Asn Ser Lys Lys
                 95                 100                 105

Arg Lys Arg Glu Thr Glu Asp Val Pro Lys Asp Lys Ser Ser Thr
                110                 115                 120

Gly Asp Gly Thr Gly Asn Lys Arg Lys Ile Ala Leu Glu Asp Val
                125                 130                 135

Pro Glu Lys Gln Lys Asn Leu Glu Glu Gly His Ser Ser Thr Val
                140                 145                 150

Ala Ala His Tyr Asn Glu Leu Gln Glu Val Gly Leu Glu Lys Arg
                155                 160                 165

Ser Gln Ser Arg Ile Phe Tyr Leu Arg Asn Phe Asn Asn Trp Met
                170                 175                 180

Lys Ser Val Leu Ile Gly Glu Phe Leu Glu Lys Val Arg Gln Lys
                185                 190                 195

Lys Lys Arg Asp Ile Thr Val Leu Asp Leu Gly Cys Gly Lys Gly
                200                 205                 210

Gly Asp Leu Leu Lys Trp Lys Lys Gly Arg Ile Asn Lys Leu Val
                215                 220                 225

Cys Thr Asp Ile Ala Asp Val Ser Val Lys Gln Cys Gln Gln Arg
                230                 235                 240

Tyr Glu Asp Met Lys Asn Arg Arg Asp Ser Glu Tyr Ile Phe Ser
                245                 250                 255
```

```
Ala Glu Phe Ile Thr Ala Asp Ser Ser Lys Glu Leu Leu Ile Asp
            260                 265                 270

Lys Phe Arg Asp Pro Gln Met Cys Phe Asp Ile Cys Ser Cys Gln
        275                 280                 285

Phe Val Cys His Tyr Ser Phe Glu Ser Tyr Glu Gln Ala Asp Met
        290                 295                 300

Met Leu Arg Asn Ala Cys Glu Arg Leu Ser Pro Gly Gly Tyr Phe
        305                 310                 315

Ile Gly Thr Thr Pro Asn Ser Phe Glu Leu Ile Arg Arg Leu Glu
        320                 325                 330

Ala Ser Glu Thr Glu Ser Phe Gly Asn Glu Ile Tyr Thr Val Lys
        335                 340                 345

Phe Gln Lys Lys Gly Asp Tyr Pro Leu Phe Gly Cys Lys Tyr Asp
        350                 355                 360

Phe Asn Leu Glu Gly Val Val Asp Val Pro Glu Phe Leu Val Tyr
        365                 370                 375

Phe Pro Leu Leu Asn Glu Met Ala Lys Lys Tyr Asn Met Lys Leu
        380                 385                 390

Val Tyr Lys Lys Thr Phe Leu Glu Phe Tyr Glu Glu Lys Ile Asn
        395                 400                 405

Asn Glu Asn Lys Met Leu Leu Lys Arg Pro Gln Ala Leu Glu Pro
        410                 415                 420

Tyr Pro Ala Asn Glu Ser Ser Lys Leu Val Ser Glu Lys Val Asp
        425                 430                 435

Asp Tyr Glu His Ala Ala Lys Tyr Met Lys Asn Ser Gln Val Arg
        440                 445                 450

Leu Pro Leu Gly Thr Leu Ser Lys Ser Glu Trp Glu Ala Thr Ser
        455                 460                 465

Ile Tyr Leu Val Phe Ala Phe Glu Lys Gln Gln
        470                 475

<210> SEQ ID NO 115
<211> LENGTH: 1952
<212> TYPE: DNA
<213> ORGANISM: Candida albacans
<220> FEATURE:
<223> OTHER INFORMATION: Nucleotide sequence of cap methyltransferase
      gene.

<400> SEQUENCE: 115
gatctaaata cgcatcaaca ttttacaagt cggtccacat gtttccccat           50
gagggagctc attatgttcc taacaaaaaa gactttcttg aaccaattgt          100
aaagttattt gacaaaacgt tgaatgaaaa gccaatgtta tagatgattt          150
tatagagtaa aatagataaa ttgttatgtt gtaaggaaaa aaaaaaagcg          200
agcaaaaaaa aaaattgagt tgaaacatga atcattagtt tctacaccac          250
tagcatgtct accgattcgt acactccctc acaagagcct ggttcaaagc          300
gtttaaagac gggcgaatct gtatttgcaa gaagaggagt atcgccaagt          350
actggtggag tggcatcagc ctacggtaat gagagtgaga aaaagccatc          400
gtggttacaa accaacaaaa gtgatattga tgggaagtac gataaatatg          450
gagagagaag aaatgcccat actacaacaa gagactcaag acttgatagg          500
ttaaagcgag ttcgtcaaaa gctggctgag cgggaagatg ttggtcatga          550
```

-continued

| | |
|---|---|
| aggagacgaa ggagacgagg atgagggtat attaccttat attcatttac | 600 |
| aagcggccaa ccctgccatc attcacaacg agaaacagga aaactatcgt | 650 |
| aagtttcaga gtaggatatc gaatagagag aatagagaca tcaatagtat | 700 |
| tgtgagggca cactataatc agcgaacaca acaagcaaaa cagcaaggat | 750 |
| cccgagtcaa ttcgccaatt tacaaaatga ggaatttcaa caatgccatt | 800 |
| aaatacatat tgttgggtaa ttgggccaaa cataatccag aggaattgga | 850 |
| tttgttttct tttttggatt tatgttgtgg caaaggtggg gatttgaaca | 900 |
| aatgccaatt tattggcatt gatcaatata ttggcattga cattgctgat | 950 |
| ttatcggtca aagaagcatt tgaacggtac acaaaacaaa aggcgaggtt | 1000 |
| cagacactct aatcagaatt ctaatcggta tacttttgag gcgtgttttg | 1050 |
| ccacagggga ttgtttcacc caatttgtgc ctgatatcct agagccaaat | 1100 |
| ttccctggaa ttatagaacg tgcatttccc gtggatattg tttccgccca | 1150 |
| gttttcgttg cattattctt ttgaaagtga agaaaaggta cgtacattgt | 1200 |
| tgaccaacgt cacaaggtcg ttgcgttcag gaggcacttt tattggcaca | 1250 |
| attccttcct ctgatttcat aaaggcaaaa atagttgaca acatttgca | 1300 |
| acgagatgaa aaggggaaag cgaagtttgg taatagtttg tattcggtga | 1350 |
| cgtttgaaaa agatcctcca gaagatggcg tattccgtcc tgcgtttggg | 1400 |
| aacaagtaca attattggtt gaaagatgcc gttgacaatg ttcctgagta | 1450 |
| tgtggttccg tttgaaacat tgagatcatt gtgtgaagag tacgatttgg | 1500 |
| ttttgaagta taaaaagagt tttacagata tattcaacca ggagattcca | 1550 |
| aagtatttta gtaaattgaa taaaaatcta attgatggaa tgaaacgaag | 1600 |
| tgatggcaag tacggtgctg aaggtgacga aaaggaagca gtggcatttt | 1650 |
| acataggatt tgtatttgag aaggtatagg atatgtctgg gtagtgtgta | 1700 |
| gcattttttg ggtcaaggat ctttacgaaa aaattaagaa aagtaaacaa | 1750 |
| cagaggactt tttccgatcc gttttagtca atgactcgct gtacataaaa | 1800 |
| ccaatctaaa tggttaagta ccactaaaaa aaaaaaaaa actccatcta | 1850 |
| tatttatttt cagaacaatt acttataact aaaagtaatc ggactatata | 1900 |
| agtcgaggca acacaaagtt taggcgtgat agtagttcga ctagatactc | 1950 |
| ta | 1952 |

<210> SEQ ID NO 116
<211> LENGTH: 474
<212> TYPE: PRT
<213> ORGANISM: Candida albacans
<220> FEATURE:
<223> OTHER INFORMATION: Amino acid sequence of cap methyltransferase
      gene

<400> SEQUENCE: 116

Met Ser Thr Asp Ser Tyr Thr Pro Ser Gln Glu Pro Gly Ser Lys
                  5                  10                  15

Arg Leu Lys Thr Gly Glu Ser Val Phe Ala Arg Arg Gly Val Ser
                 20                  25                  30

Pro Ser Thr Gly Gly Val Ala Ser Ala Tyr Gly Asn Glu Ser Glu
                 35                  40                  45

Lys Lys Pro Ser Trp Leu Gln Thr Asn Lys Ser Asp Ile Asp Gly

-continued

```
                50                  55                  60
Lys Tyr Asp Lys Tyr Gly Glu Arg Arg Asn Ala His Thr Thr Thr
                65                  70                  75
Arg Asp Ser Arg Leu Asp Arg Leu Lys Arg Val Arg Gln Lys Ser
                80                  85                  90
Ala Glu Arg Glu Asp Val Gly His Glu Gly Asp Glu Gly Asp Glu
                95                 100                 105
Asp Glu Gly Ile Leu Pro Tyr Ile His Leu Gln Ala Ala Asn Pro
               110                 115                 120
Ala Ile Ile His Asn Glu Lys Gln Glu Asn Tyr Arg Lys Phe Gln
               125                 130                 135
Ser Arg Ile Ser Asn Arg Glu Asn Arg Asp Ile Asn Ser Ile Val
               140                 145                 150
Arg Ala His Tyr Asn Gln Arg Thr Gln Gln Ala Lys Gln Gln Gly
               155                 160                 165
Ser Arg Val Asn Ser Pro Ile Tyr Lys Met Arg Asn Phe Asn Asn
               170                 175                 180
Ala Ile Lys Tyr Ile Leu Leu Gly Asn Trp Ala Lys His Asn Pro
               185                 190                 195
Glu Glu Leu Asp Leu Phe Ser Phe Leu Asp Leu Cys Cys Gly Lys
               200                 205                 210
Gly Gly Asp Leu Asn Lys Cys Gln Phe Ile Gly Ile Asp Gln Tyr
               215                 220                 225
Ile Gly Ile Asp Ile Ala Asp Leu Ser Val Lys Glu Ala Phe Glu
               230                 235                 240
Arg Tyr Thr Lys Gln Lys Ala Arg Phe Arg His Ser Asn Gln Asn
               245                 250                 255
Ser Asn Arg Tyr Thr Phe Glu Ala Cys Phe Ala Thr Gly Asp Cys
               260                 265                 270
Phe Thr Gln Phe Val Pro Asp Ile Leu Glu Pro Asn Phe Pro Gly
               275                 280                 285
Ile Ile Glu Arg Ala Phe Pro Val Asp Ile Val Ser Ala Gln Phe
               290                 295                 300
Ser Leu His Tyr Ser Phe Glu Ser Glu Lys Val Arg Thr Leu
               305                 310                 315
Leu Thr Asn Val Thr Arg Ser Leu Arg Ser Gly Gly Thr Phe Ile
               320                 325                 330
Gly Thr Ile Pro Ser Ser Asp Phe Ile Lys Ala Lys Ile Val Asp
               335                 340                 345
Lys His Leu Gln Arg Asp Glu Lys Gly Lys Ala Lys Phe Gly Asn
               350                 355                 360
Ser Leu Tyr Ser Val Thr Phe Glu Lys Asp Pro Pro Glu Asp Gly
               365                 370                 375
Val Phe Arg Pro Ala Phe Gly Asn Lys Tyr Asn Tyr Trp Leu Lys
               380                 385                 390
Asp Ala Val Asp Asn Val Pro Glu Tyr Val Val Pro Phe Glu Thr
               395                 400                 405
Leu Arg Ser Leu Cys Glu Glu Tyr Asp Leu Val Leu Lys Tyr Lys
               410                 415                 420
Lys Ser Phe Thr Asp Ile Phe Asn Gln Glu Ile Pro Lys Tyr Phe
               425                 430                 435
Ser Lys Leu Asn Lys Asn Leu Ile Asp Gly Met Lys Arg Ser Asp
               440                 445                 450
```

-continued

```
Gly Lys Tyr Gly Ala Glu Gly Asp Glu Lys Glu Ala Val Ala Phe
            455                 460                 465

Tyr Ile Gly Phe Val Phe Glu Lys Val
            470
```